(12) United States Patent
Pierre et al.

(10) Patent No.: US 10,969,387 B2
(45) Date of Patent: Apr. 6, 2021

(54) COMPOUNDS, COMPLEXES, AND METHODS USEFUL FOR DETECTING AND/OR TREATING BACTERIAL PATHOGENS

(71) Applicants: REGENTS OF THE UNIVERSITY OF MINNESOTA, Minneapolis, MN (US); Valerie Christine Pierre, Vadnais Heights, MN (US); Sylvie Pailloux, Minneapolis, MN (US)

(72) Inventors: Valerie Christine Pierre, Vadnais Heights, MN (US); Sylvie Pailloux, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 290 days.

(21) Appl. No.: 16/062,806

(22) PCT Filed: Dec. 15, 2016

(86) PCT No.: PCT/US2016/066790
§ 371 (c)(1),
(2) Date: Jun. 15, 2018

(87) PCT Pub. No.: WO2017/106425
PCT Pub. Date: Jun. 22, 2017

(65) Prior Publication Data
US 2020/0264174 A1    Aug. 20, 2020

Related U.S. Application Data

(60) Provisional application No. 62/267,559, filed on Dec. 15, 2015.

(51) Int. Cl.
| | |
|---|---|
| *G01N 33/569* | (2006.01) |
| *C07F 5/00* | (2006.01) |
| *C07F 15/02* | (2006.01) |
| *C12Q 1/18* | (2006.01) |

(52) U.S. Cl.
CPC ........ *G01N 33/56911* (2013.01); *C07F 5/003* (2013.01); *C07F 15/025* (2013.01); *C12Q 1/18* (2013.01)

(58) Field of Classification Search
None
See application file for complete search history.

(56) References Cited

U.S. PATENT DOCUMENTS

| | | | |
|---|---|---|---|
| 4,652,521 A | 3/1987 | Confer et al. | |
| 4,880,008 A * | 11/1989 | Lauffer | A61K 49/06 424/9.363 |
| 2004/0137430 A1 | 7/2004 | Anderson et al. | |
| 2013/0309687 A1 | 11/2013 | Henderson | |

OTHER PUBLICATIONS

Dertz et al. Inorganic Chem. (2006) 45: 5465-5478 (Year: 2006).*
Barbeau et al. (inmol. Oceanogr. (2003) 48(3): 1069-1078 (Year: 2003).*
"Report to the President on Combating Antibiotic Resistance", Executive Office of the President of the United States, President's Council of Advisors on Science and Technology, 78 pages (Sep. 2014).
Heinisch, L , et al., "New synthetic catecholate-type siderophores with triamine backbone", Biometals 15(2), 133-144 (2002).
Patent Cooperation Treaty, International Searching Authority, Search Report and Written Opinion for PCT/US2016/066790, 9 pages, dated May 8, 2017.

* cited by examiner

*Primary Examiner* — Susan M Hanley
(74) *Attorney, Agent, or Firm* — Viksnins Harris Padys Malen LLP

(57) ABSTRACT

Compounds and complexes that can be useful as enterobactin probes not necessary are disclosed herein. Methods of detecting bacteria and/or methods of determining susceptibility of bacteria to an antibiotic using such compounds and complexes are also disclosed herein.

17 Claims, 22 Drawing Sheets

COMPOUNDS, COMPLEXES, AND METHODS USEFUL FOR DETECTING AND/OR TREATING BACTERIAL PATHOGENS

This application is the § 371 U.S. National Stage of International Application No. PCT/US2016/066790, filed 15 Dec. 2016, which claims the benefit of U.S. Provisional Application No. 62/267,559, filed Dec. 15, 2015, the disclosures of which are incorporated herein by reference in their entireties its entirety.

GOVERNMENT SUPPORT

This invention was made with government support under RR033183 awarded by the National Institutes of Health. The government has certain rights in the invention.

BACKGROUND

The prevalence of bacterial pathogens and the increase in antibiotic-resistant strains is in part due to the difficulty of rapidly detecting the bacterial pathogens at the point of care, which in turn, can lead to over-prescription of antibiotics, and breeding further selection of antimicrobial resistance. Rapid and accurate diagnosis of bacterial infections can promote optimal patient outcomes such as lower adverse events, shorter hospital stays, and better long-term prognoses, and can reduce selection of antibiotic-resistant organisms. Unfortunately, the results of today's diagnostics tests are often not available in sufficient time to inform treatment decisions in outpatient settings, where most antibiotics are prescribed. In addition, an acute illness presented in a hospital setting commonly requires empiric antimicrobial treatment before relevant antimicrobial susceptibility information is available.

Patient care and antibiotic stewardship would be advanced by development and application of rapid diagnostics that provide accurate and timely information as to the nature of the infecting pathogen, including whether it is bacterial, and its resistance profile. Ideally, diagnostics should accurately predict the need or lack thereof for specific antibiotics. This need for improved diagnostics is emphasized in the recent "Report to the President on Combating Antibiotic Resistance" (2014). Among the recommendations in this report is the recommendation that the government take steps to accelerate development and adoption of rapid diagnostics for bacterial infections.

Of the bacterial pathogens that are preponderant in the US and the world, the CDC has placed special emphasis on the Enterobacteriaceae (including *E. coli, Klebsiella* spp., *Enterobacter* spp., and *Salmonella* spp.), *Acinetobacter baumannii*, and *Pseudomonas aeruginosa*. (ANTIBIOTIC RESISTANCE THREATS in the United States, 2013 CDC antibiotic resistance threats in the United States).

Current FDA-approved technologies for the detection of bacteria are labor-intensive. Those that are sensitive rely primarily on bacterial cultures that are lengthy. The time-to-results for these assays, typically longer than 48 hours, are too long for infectious diseases that require immediate treatment. The FDA-approved technologies that do not rely on bacterial cultures are based on gene detection. When tested with clinical samples, these gene-detection technologies have insufficient sensitivity to detect most bacterial infections. Recent technologies developed for bacterial detection are based either on nucleic acid detection or the use of antibodies.

There is a continuing need for compounds and methods for use in detecting bacterial pathogens.

SUMMARY

In one aspect, the present disclosure provides compounds, complexes, and methods useful for detecting and/or treating bacterial pathogens.

In one embodiment, the present disclosure provides a compound of the formula:

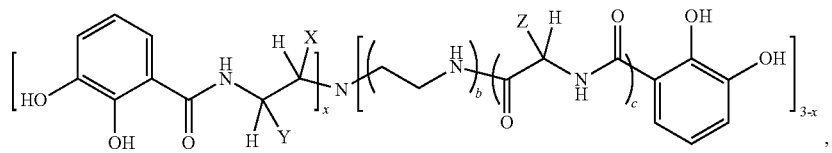

Formula I wherein: each X independently represents H and the vicinal Y represents H or -L-B; or each Y independently represents H and the vicinal X represents H or -L-B; each Z independently represents H or -L-B; each L independently represents an organic linking group; each B independently represents —OR, —NR$_2$, —SR, —C(O)OR, —C(O)NR$_2$, —S(O)R, or —SO$_2$R; each R independently represents H or an organic group; each b is independently 0 or 1; each c is independently 0 or 1; and x=0 to 3; with the proviso that at least one of X, Y, or Z is present and represents -L-B.

In another embodiment, the present disclosure provides a compound of the formula:

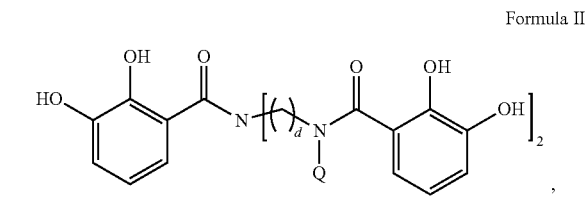

Formula II wherein: each Q independently represents H or —(CH$_2$)$_n$-D; each D independently represents —OR, —NR$_2$, —SR, or —C(O)OR; each R independently represents H or an organic group; and each d is independently 2 to 5; with the proviso that at least one Q represents —(CH$_2$)$_n$-D.

In another embodiment, the present disclosure provides a compound of the formula:

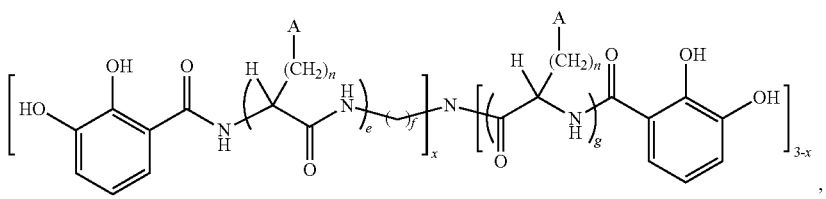

Formula III wherein: each A independently represents —OR, —NR₂, —SR, or —C(O)OR; each R independently represents H or an organic group; each n is independently 2 to 5; each e is independently 0 or 1; each f is independently 2 to 3; each g is independently 0 or 1; and x=0 to 3; with the proviso that at least one A is present.

In another aspect, the present disclosure provides a complex of a compound of Formula I, Formula II, and/or Formula III selected from the group consisting of a Ga(III) complex, an Fe(III) complex, an Al(III) complex, a V(IV) complex, a Zn(II) complex, an Y(III) complex, a Zr(VI) complex, a Cu(II) complex, and combinations thereof.

In another aspect, the present disclosure provides a method of detecting bacteria including: contacting a probe including a compound or complex of Formula I, Formula II, and/or Formula III as disclosed herein with a sample including a component selected from the group consisting of a bodily fluid, an isolated colony, a culture, and combinations thereof, under conditions effective for the probe to complex Fe(III), Al(III), V(IV), Zn(II), Y(III), Zr(IV), and/or Cu(II) present in the bodily fluid, the isolated colony, and/or the culture; and detecting the presence of Fe(III), Al(III), V(IV), Zn(II), Y(III), Zr(IV), and/or Cu(II)-probe complex to indicate the presence of bacteria in the bodily fluid, the isolated colony, and/or the culture.

In another aspect, the present disclosure provides a method of determining susceptibility of bacteria to an antibiotic including: treating a sample including a component selected from the group consisting of a bodily fluid, a bacteria culture, a single colony reconstituted in media with an antibiotic, and combinations thereof; contacting a probe including a compound or complex Formula I, Formula II, and/or Formula III with the sample including a component selected from the group consisting of the bodily fluid, the isolated colony, the culture, and combinations thereof, under conditions effective for the probe to complex Fe(III); and determining the change in concentration of the compound or complex to indicate the concentration of bacteria in the bodily fluid, the bacteria culture, or the isolated colony after treatment with the antibiotic, wherein the difference between the initial concentration of bacteria and the concentration of bacteria in the bodily fluid, the bacteria culture, or the isolated colony after treatment with the antibiotic is an indication of the susceptibility of the bacteria to the antibiotic.

In another aspect, the present disclosure provides a method of treating a patient having a disease caused by bacteria comprising: administering to the patient under conditions effective to treat the disease a probe comprising a compound or complex as described herein, wherein at least one R represents an organic group comprising an antiobiotic.

As opposed to recently FDA-approved technologies, methods using the compounds and/or complexes disclosed herein advantageously do not target genes; nor do they require cultures, polymerase charin reaction (PCR) techniques, or other techniques that are lengthy, expensive, have limited sensitivity, and/or are labor-intensive. Methods using the compounds and/or complexes disclosed herein make use of chemical probes that, unlike antibodies and gene-based assays, can be readily stored at room temperature for extended periods of time, and can be easily scaled up for manufacturing.

Definitions

As used herein, the term "vicinal" is used to refer to substituents attached to adjacent carbon atoms.

As used herein, the term "TREN" is used to refer to the chelator tris(2-aminoethyl)amine.

As used herein, the term "DOTA" is used to refer to the chelator 1,4,7,10-tetraazacyclododecane-1,4,7,10-tetraacetic acid.

As used herein, the term "DO3A" is used to refer to the chelator tris(carboxymethyl)-1,4,7,10-tetraazacyclododecane.

As used herein, the term "CAM" is used to refer to 2,3-dihydroxybenzamide.

As used herein, the term "NP" is used to refer to nanoparticles.

As used herein, the term "DCM" is used to refer to dichloromethane, $CH_2Cl_2$.

As used herein, the term "DMF" is used to refer to N,N-dimethylformamide, $(CH_3)_2NC(O)H$.

As used herein, the term "DIPEA" is used to refer to N,N-diisopropylethylamine, $((CH_3)_2CH)_2NC_2H_5$.

As used herein, the term "AcOH" is used to refer to acetic acid, $CH_3CO_2H$.

As used herein, the term "Bn" is used to refer to a benzyl group, $C_6H_5CH_2$—.

As used herein, the term "NHS" is used to refer to N-hydroxysuccinimide.

As used herein, the term "acac" is used to refer to the ligand acetylacetonate.

As used herein, the term "DMAP" is used to refer to 4-dimethylaminopyridine.

As used herein, the term "ACN" is used to refer to acetonitrile, $CH_3CN$.

As used herein, the term "organic group" is used for the purpose of this disclosure to mean a hydrocarbon group that is classified as an aliphatic group, cyclic group, or combination of aliphatic and cyclic groups (e.g., alkaryl and aralkyl groups). In the context of the present disclosure, suitable organic groups for compounds of this disclosure are those that do not interfere with methods of detecting bacteria, determining susceptibility of bacteria to an antibiotic, and/or treating a patient having a disease caused by bacteria, using a compound and/or complex as disclosed herein. In the context of the present disclosure, the term "aliphatic group"

means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above brief description of various embodiments of the present disclosure is not intended to describe each embodiment or every implementation of the present disclosure. Rather, a more complete understanding of the disclosure will become apparent and appreciated by reference to the following description and claims in view of the accompanying drawings. Further, it is to be understood that other embodiments may be utilized and structural changes may be made without departing from the scope of the present disclosure.

DETAILED DESCRIPTION OF ILLUSTRATIVE EMBODIMENTS

Siderophores as Markers of Bacterial Virulence

Iron is an essential element for all but one known organism, including pathogenic bacteria. The oxidized form is insoluble, while the reduced form is highly toxic, and the human body efficiently chelates both forms by iron and heme-carrier proteins. Consequently, the free ferric ion concentration available to bacteria in serum is maintained at approximately $10^{-24}$M (Raymond et al., *Proceedings of the National Academy of Sciences.* 2003; 100(7):3584-8). In response to the paradox of approximately $10^{-6}$ M concentration required for microbial growth (Braun et al., *Trends in Biochemical Sciences.* 1999; 24(3):104-9), and the negligible amount of free iron available in vivo, bacteria have developed intricate systems to sequester iron from their environment. Of these, during infection, Gram-negative pathogens rely primarily on siderophores to acquire their iron. Siderophores are small molecule iron chelators excreted by microorganisms to sequester iron from their environment and bring it into bacteria. Siderophores have been identified as important virulence factors for every type of pathogenic Gram-negative bacteria (Caza et al., *Frontiers in Cellular and Infection Microbiology.* 2013; 3. doi: 10.3389/fcimb.2013.00080; Beceiro et al., *Clinical Microbiology Reviews.* 2013; 26(2):185-230). As discussed herein, siderophores may have great potential for the development of novel technology for bacterial detection, a potential that is yet untapped.

Figure 1:
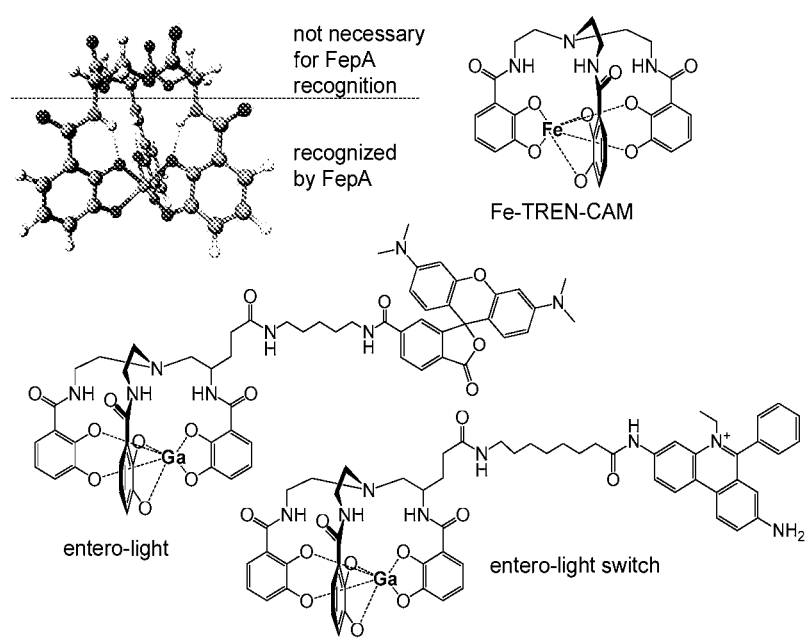
FIG. 1 is a schematic illustration of the chemical structure of an exemplary embodiment of an enterobactin, Fe-TREN-CAM—an enterobactin mimic recognized and taken up by E. coli, and the fluorescent probes entero-light and entero-light switch.

All clinical isolates of the Enterobacteriaceae, including E. coli (Raymond et al., *Proceedings of the National Academy of Sciences.* 2003; 100(7):3584-8, Watts et al., *Infect Immun.* 2012; 80(1):333-44), Klebsiella (El Fertas-Aissani et al., Pathol Biol. 2013; 61(5):209-16), and Enterobacter species (Mokracka et al., *FEMS Immunol Med Microbiol.* 2004; 40(1):51-5), the microorganisms that cause greater than 90% of cases of urinary tract infection (UTI), synthesize and take up the catechol-based siderophore enterobactin (FIG. 1). The other bacterial pathogens that can cause UTI—Proteus (Rutz et al., *J Bacteriol.* 1991; 173(19):5964-74; Ritter et al., *Mol Microbiol.* 1995; 17(1):109-21), Pseudomonas (Ji et al., *Journal of the American Chemical Society.* 2012; 134(24):9898-901), Serratia (Rutz et al., *J Bacteriol.* 1991; 173(19):5964-74), Staphylococcus (Clancy et al., *Mol Microbiol.* 2006; 59(2):707-21), and Enterococcus (Clancy et al., *Mol Microbiol.* 2006; 59(2):707-21)—do not synthesize enterobactin but are well known to take it up. Since enterobactin is taken up by all known bacterial pathogens causing UTI, an enterobactin-based fluorescent probe could enable rapid detection of all known bacteria causing UTI, and thus, diagnosis of UTI could be done with a single, simple test. Moreover, siderophores are not recognized or taken up by mammalian cells. Assays that make use of siderophore-based probes may not be affected by any mammalian cells (i.e. white and red blood cells) present in the sample, as confirmed by preliminary results disclosed herein.

Importantly, urine samples are not completely sterile. Low concentration of bacteria present in the sample is not indicative of UTI. The most commonly used criterion for defining significant bacteriuria is the presence of $\geq 10^5$ cfu per mL of urine (Stamm et al., *N Engl J Med.* 1982; 307(8):463-8; Wilson et al., *Clinical Infectious Diseases.* 2004; 38(8):1150-8). For practical diagnosis of UTI, it is therefore important not only to be able to detect the presence of bacteria, but also to be able to determine the concentration of the bacteria. This is a distinct advantage of fluorescence assays over gene-based assays: not only can they indicate the concentration of the bacteria, but they can also be tuned to determine the concentration of bacteria between $10^3$ and $10^7$ CFU/mL, as needed for the accurate diagnosis of UTI.

Detection of E. coli with a Fluorescent Siderophore Probe

The structural parameters of enterobactin necessary for its recognition by the outer-membrane receptor FepA and ATP-dependent uptake by E. coli and other bacteria are known. While modification of the trilactone backbone does not inhibit uptake of the siderophore, modification of the catecholamide moieties does (Raymond et al., *Proceedings of the National Academy of Sciences.* 2003; 100(7):3584-8). Among the derivatives studied, TREN-CAM is recognized by FepA and actively taken up by E. coli. (Thulasiraman et al., *J Bacteriol.* 1998; 180(24):6689-96). Herein we have investigated modifying the natural product further by incorporating a chemical handle, such as a carboxylic acid, on the TREN backbone, an dextended TREN backbone, or a linear cap. The carboxylic acid would in turn enable further conjugation of a detection group or a drug, effectively changing the siderophore into an effective vector. This strategy exploits the siderophore uptake system of bacteria, which are key to their virulence, as a gate into the bacterial envelope. With this in mind, we designed and synthesized entero-light (FIG. 1), a fluorescent enterobactin probe incorporating the bright luminescent dye available under the trade designation OREGON GREEN CADAVERINE from Thermo Fisher Scientific.

Following the protocol detailed below (Sample Processing for bacteria detection by fluorescence in T media), we determined that our class of probes can detect pathogenic Gram-negative bacteria such as E. coli, K pneumoniae, Salmonella, A. baumannii, B. subtilus, and S. aureus with substantial turn-on. In each case, at least a four-fold increase in fluorescence intensity was observed in the presence of bacteria. This protocol required little steps: a short incubation followed by a simple centrifugal wash. (Importantly, this washing step can be eliminated with turn-on probes such as Ga-2,2-LiCAM-GluCAM-light switch—example 6 below). Comparison of the different examples of probes indicate that Ga-3,3-LiCAM-GluCAM gives a higher turn-on. Notably, when not conjugated to an enterobactin analogue, the OREGON GREEN fluorescent dye does not accumulate in bacteria. This control experiment highlights the benefits of incorporating our enterobactin targeting vectors in the design of probes for bacteria imaging.

Further comparison of the Ga(III), Fe(III) and apo (non-metallated) probe indicate that, although not necessary, the gallium(III) and iron(III) probes yield greater response. It is known that only metal complexes of siderophore are recognized by the enterobactin receptor FepA. Although the incubation media, T-media, is deprived of iron, it is not absolutely iron-free. The apo probe efficientlchelates out any residual iron from the media, and it is this iron complex that is taken up by the bacteria. Moreover, the iron probe exhibits a lower response than the gallium probe. This observation is likely due either to partial quenching of the fluorescence of the OREGON GREEN dye by the iron(III) ion, or by lower uptake of the Fe(III) probe than the Ga(III) one. This is predicted on the basis that, as opposed to the Fe(III) probe, uptake of the Ga(III) complex would not trigger the Fur (ferric iron uptake regulator) receptor. In any case, this result confirms that the gallium complexes presented are recognized by the FepA receptor. This conclusion is further supported by the observation that the uptake of the Ga(III), Fe(III), and unmetallated 3,3-LiCAM-GluCAM-OG probe decreases substantially if the media is supplemented by iron. Importantly, varying the incubation time indicates that the probes are taken up rapidly and efficiently in as little as 10 minutes. The protocol can thus be shortened to include a brief 10 minute incubation time (as opposed to a 20 minute incubation time).

Figure 34:
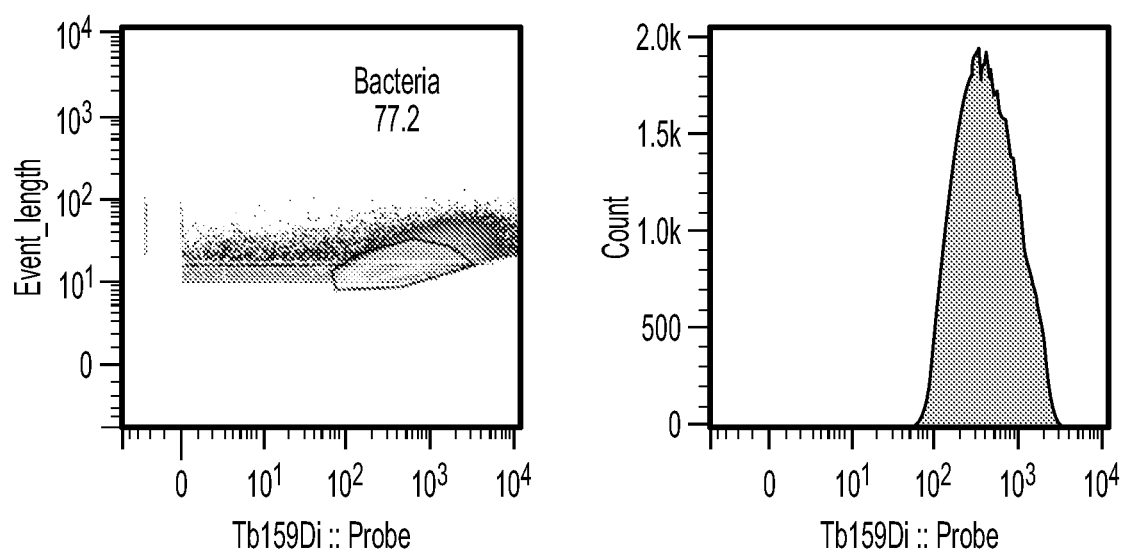
FIG. 34 is an illustration of cytomas data. Left: biaxial dot plot where each dot is an individually detected event. The number of mass spectra integrated to give a single "event" on the y-axis of the probe intensity in each event, on the x-axis. Right: histogram of the gated most intense part of the dot cloud indicating the number of terbium ion per event counted (bacteria). For reference, the events shown on the right hand side represent approximately 100,000 "bacterial events."

Importantly, this class of probe is not limited to the detection of bacteria by fluorescence. As shown in FIG. 34, a mass cytometry probe bearing a terbium complex as opposed to a fluorescent probe, Fe-3,3-LiCAM-GluCAM-Tb (example 7) also enables rapid detection of E. coli by cytomass.

Compounds and Complexes

In one embodiment, the present disclosure provides a compound of the formula:

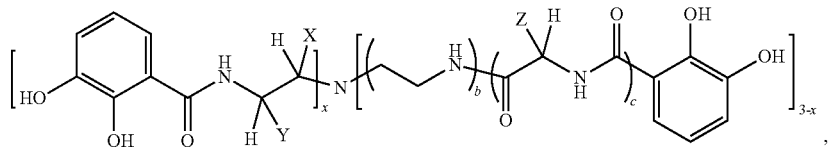

Formula I wherein: each X independently represents H and the vicinal Y represents H or -L-B; or each Y independently represents H and the vicinal X represents H or -L-B; each Z independently represents H or -L-B; each L independently represents an organic linking group; each B independently represents —OR, —NR$_2$, —SR, —C(O)OR, —C(O)NR$_2$, —S(O)R, or —SO$_2$R; each R independently represents H or an organic group; each b is independently 0 or 1; each c is independently 0 or 1; and x=0 to 3; with the proviso that at least one of X, Y, or Z is present and represents -L-B. In some embodiments, each R can independently represent an organic moiety.

In some embodiments, each organic linking group L can independently represent a straight-chain group of the formula —(CH$_2$)$_n$— or —(CH$_2$—CH$_2$—O)$_n$—, wherein n is 1 to 8. In certain embodiments, each organic linking group L can independently represent a branched chain dendrimer that contains one or more of C, N, S, and O. In some certain embodiments, each organic linking group L can independently represent an organic moiety.

In another embodiment, the present disclosure provides a compound of the formula:

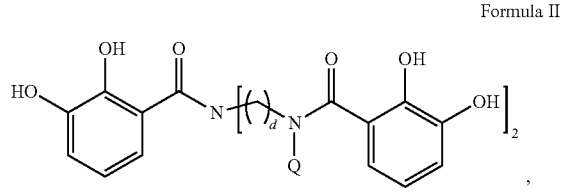

Formula II wherein: each Q independently represents H or —(CH$_2$)$_n$-D; each D independently represents —OR, —NR$_2$, —SR, or —C(O)OR; each R independently represents H or an organic group; and each d is independently 2 to 5; with the proviso that at least one Q represents —(CH$_2$)$_n$-D. In some embodiments, each R can independently represent an organic moiety.

In another embodiment, the present disclosure provides a compound of the formula:

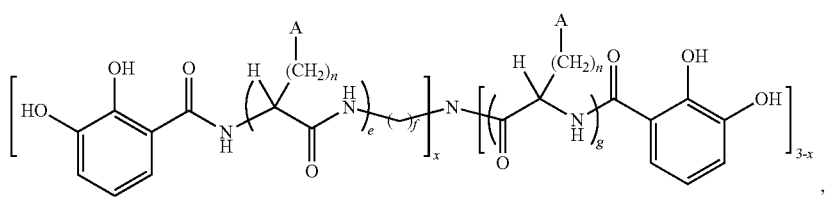

Formula III wherein: each A independently represents —OR, —NR$_2$, —SR, or —C(O)OR; each R independently represents H or an organic group; each n is independently 2 to 5; each e is independently 0 or 1; each f is independently 2 to 3; each g is independently 0 or 1; and x=0 to 3; with the proviso that at least one A is present. In some embodiments, each R can independently represent an organic moiety.

In some embodiments of compounds of Formula I, Formula II, and/or Formula III, R can be an organic group including a group selected from the group consisting of a dye, a Lanthanide complex, a magnetic resonance imaging (MRI) contrast agent, a positron emission tomography (PET) agent, a gold nanoparticle, a silver nanoparticle, a quantum dot, an antibiotic or an antibacterial drug, an antimicrobial peptide, a polymer, a dendrimer, an ionophore, and combinations thereof.

For embodiments in which for compounds of Formula I, Formula II, and/or Formula III R represents an organic group including a dye, a wide variety of dyes can be used including, for example, fluorescent dyes such as fluorescein dyes, rhodamine dyes, thiozole orange, ethidium dyes, Alexa fluor dyes, coumarin dyes, cyanine dyes, SYBR dyes, SYTO dyes, acridine dyes, propidium dyes, TOPRO, TOTO, YOYO, YOPRO, BOBO, and BODIPY dyes. Exemplary dyes include, but are not limited to, dyes available under the trade designation ALEXA FLUOR from Thermo Fisher Scientific, dyes available under the trade designation TAMRA from Thermo Fisher Scientific, dyes available under the trade designation OREGON GREEN from Thermo Fisher Scientific, dyes available under the trade designation SYBR from Thermo Fisher Scientific, dyes available under the trade designation CY from Thermo Fisher Scientific, dyes available under the trade designation BODIPY from Thermo Fisher Scientific, dyes available under the trade designation PACIFIC from Thermo Fisher Scientific (e.g., PACIFIC GREEN, PACIFIC BLUE, AND PACIFIC ORANGE), coumarin dyes, DNA stain, and quantum dots available under the trade designation Qdot from Thermo Fisher Scientific.

For embodiments in which for compounds of Formula I, Formula II, and/or Formula III R represents an organic group including a positron emission tomography (PET) agent, a wide variety of PET agents can be used. Exemplary PET agents include, but are not limited to, $^{18}$F probes such as charged chelated aluminum fluoride complexes; $^{18}$F probes such as conjugated $^{18}$FDG, $^{64}$Cu probes such as charged chelated copper complexes; $^{67}$Ga and $^{68}$Ga probes such as conjugated chelated gallium complexes; $^{94m}$Tc probes such as chelated technetium complexes, and $^{89}$Zr probes such as chelated zirconium complexes.

For embodiments in which for compounds of Formula I, Formula II, and/or Formula III R represents an organic group including an antiobiotic or an antibacterial drug, a wide variety of antibiotics and/or antibacterial drugs can be used. Exemplary antibiotics and/or antibacterial drugs include, but are not limited to, polyether antibiotics such as monensin; β-lactam antibiotics such as penicillins, amoxicillin, cephalosporins, and cephalexin; antibacterial drugs such as salinomycin; gramicidin; ciprofloxacin; metronidazole; sulfamethoxazole; trimethopin; levoflaxin; polymyxins; rifamycins; lipiarmycins; quinolones; sulfonamides; macrolide antibiotics such as azithromycin; lincosamides such as clindamycin; tetracyclines such as doxycycline and tigecycline; daptomycin; oxazolidinone antibiotics; and coumarin antibiotics such as aminocoumarin.

For embodiments in which for compounds of Formula I, Formula II, and/or Formula III R represents an organic group including an ionophore, a wide variety of ionophores can be used. Exemplary ionophores include, but are not limited to, channel compounds, modified hydraphiles, and modified calixarenes such as ionomycin and A23187; and crown ethers.

In another aspect, the present disclosure provides a complex of a compound of Formula I, Formula II, and/or Formula III selected from the group consisting of a Ga(III) complex, an Fe(III) complex, an ARM) complex, a V(IV) complex, a Zn(II) complex, an Y(III) complex, a Zr(VI) complex, a Cu(II), and combinations thereof.

Methods of Detecting Bacteria

In another aspect, the present disclosure provides a method of detecting bacteria including: contacting a probe including a compound or complex as disclosed herein with a sample including a component selected from the group consisting of a bodily fluid, an isolated colony, a culture, and combinations thereof, under conditions effective for the probe to complex Fe(III), Al(III), V(IV), Zn(II), Y(III), Zr(IV), and/or Cu(II) present in the bodily fluid, the isolated colony, and/or the culture; and detecting the presence of Fe(III), ARM), V(IV), Zn(II), Y(III), Zr(IV), and/or Cu(II)-probe complex to indicate the presence of bacteria in the bodily fluid, the isolated colony, and/or the culture.

In some embodiments, the presence of the Fe(III), Al(III), V(IV), Zn(II), Y(III), Zr(IV), and/or Cu(II)-probe complex is detected by a technique selected from the group consisting of fluorescence, positron emission tomography (PET), magnetic resonance imaging (MM), field microscopy, colorimetry, electrochemistry, mass spectrometry (MS), fluorescence spectroscopy, and combinations thereof.

In certain embodiments, the method further includes determining the concentration of the Fe(III), ARM), V(IV), Zn(II), Y(III), Zr(IV), and/or Cu(II)-probe complex to indicate the concentration of bacteria in the bodily fluid, the isolated colony, and/or the culture. For example, the concentration of the Fe(III), Al(III), V(IV), Zn(II), Y(III), Zr(IV), and/or Cu(II)-probe complex can be determined by a technique selected from the group consisting of fluorescence, positron emission tomography (PET), magnetic resonance imaging (MM), field microscopy, colorimetry, electrochemistry, mass spectrometry (MS), fluorescence spectroscopy, and combinations thereof.

Exemplary conditions for the probes and/or metal-probe complexes to be recognized by bacteria include contacting the probe and the sample for 1 minute to 1 hour at 10° C. to 40° C.

A wide variety of bodily fluids can be used with the methods for detecting bacteria disclosed herein. Exemplary bodily fluids include, but are not limited to, urine, blood, cerebrospinal fluid (CSF), pleural fluid, a bacteria culture, an isolated colony reconstituted in media, and combinations thereof.

In some embodiments, the methods disclosed herein can detect Gram-negative or Gram-positive bacteria.

A wide variety of Gram-negative bacteria can be detected by the methods disclosed herein. Exemplary Gram-negative bacteria that can be detected by the methods disclosed herein include, but are not limited to, *Enterobacteriaceae, Mycobacteria tuberculosis, Acinetobacter baumannii, Pseudomonas aeruginosa, Salmonella* sp., *Escherichia coli, Yersinia pestis, Yersinia enterocolotica, Shigella* sp., *Proteus mirabilis, Klebsiella oxytoca, Klebsiella pseumoniae Enterobacter, Neisseria meningitidis, Neisseria gonorrhea, Serratia marcescens*, and combinations thereof.

A wide variety of Gram-positive bacteria can be detected by the methods disclosed herein. Exemplary Gram-positive bacteria that can be detected by the methods disclosed herein include, but are not limited to, Gram positive *Staphylococcus aureus, Enterococcus* sp, *Streptococcus* sp, or a combination thereof.

Methods of Determining the Susceptibility of Bacteria to an Antibiotic

In another aspect, the present disclosure provides a method of determining susceptibility of bacteria to an antibiotic including: treating a sample including a component selected from the group consisting of a bodily fluid, a bacteria culture, a single colony reconstituted in media with an antibiotic, and combinations thereof contacting a probe including a compound or complex of Formula I, Formula II, and/or Formula III with the sample including the bodily fluid, the isolated colony, and/or the culture under conditions effective for the probe to complex Fe(III); and determining the change in concentration of the compound or complex to indicate the concentration of bacteria in the bodily fluid, the bacteria culture, or the isolated colony after treatment with the antibiotic, wherein the difference between the initial concentration of bacteria and the concentration of bacteria in the bodily fluid, the bacteria culture, or the isolated colony after treatment with the antibiotic is an indication of the susceptibility of the bacteria to the antibiotic.

In some embodiments, the method can further include determining the initial concentration of the bacteria in the bodily fluid, the bacteria culture, or the single colony by a method disclosed herein above. In certain embodiments, the concentration of the Fe(III), ARM), V(IV), Zn(II), Y(III), Zr(IV), and/or Cu(II)-probe complex can be determined by a technique selected from the group consisting of fluorescence, positron emission tomography (PET), magnetic resonance imaging (MRI), field microscopy, colorimetry, electrochemistry, mass spectrometry (MS), fluorescence spectroscopy, and combinations thereof.

Exemplary conditions for the probes and/or metal-probe complexes to be recognized by bacteria include contacting the probe and the sample for 1 minute to 1 hour at 10° C. to 40° C.

A wide variety of bodily fluids can be used with the methods for detecting bacteria disclosed herein. Exemplary bodily fluids include, but are not limited to, urine, blood, cerebrospinal fluid (CSF), pleural fluid, a bacteria culture, an isolated colony reconstituted in media, and combinations thereof.

In some embodiments, the methods disclosed herein can detect Gram-negative or Gram-positive bacteria.

A wide variety of Gram-negative bacteria can be detected by the methods disclosed herein. Exemplary Gram-negative bacteria that can be detected by the methods disclosed herein include, but are not limited to, *Enterobacteriaceae, Mycobacteria tuberculosis, Acinetobacter baumannii, Pseudomonas aeruginosa, Salmonella* sp., *Escherichia coli, Yersinia pestis, Yersinia enterocolotica, Shigella* sp., *Proteus mirabilis, Klebsiella oxytoca, Klebsiella pseumoniae Enterobacter, Neisseria meningitidis, Neisseria gonorrhea, Serratia marcescens*, and combinations thereof.

A wide variety of Gram-positive bacteria can be detected by the methods disclosed herein. Exemplary Gram-positive bacteria that can be detected by the methods disclosed herein include, but are not limited to, Gram positive *Staphylococcus aureus, Enterococcus* sp, *Streptococcus* sp, or a combination thereof.

Methods of Treating a Disease Caused by Bacteria

In another aspect, the present disclosure provides a method of treating a patient having a disease caused by bacteria comprising: administering to the patient under conditions effective to treat the disease a probe comprising a compound or complex as described herein, wherein at least one R represents an organic group comprising an antiobiotic.

Additional Illustrative Embodiments

Embodiment A: Ligand 1 and its Complexes with Ga and Fe Structure of Ligand

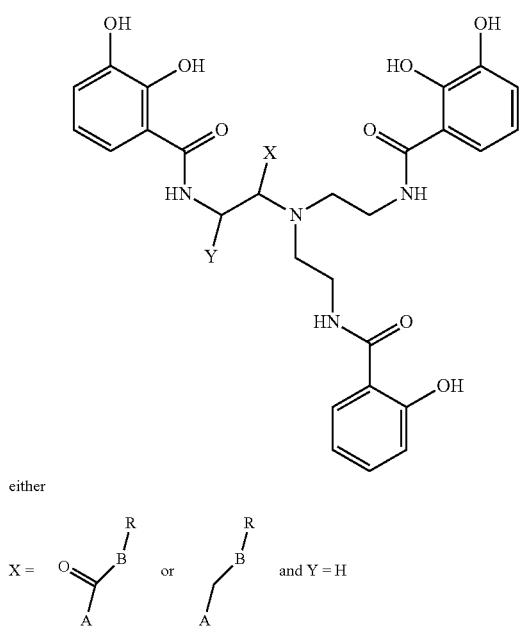

or

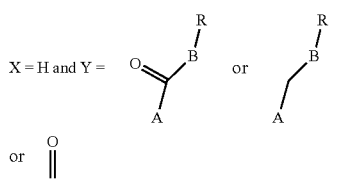

wherein A can be linear or branched, with linear including alkane or PEG chains with or without the presence of N (nitrogen), with alkane defined as a succession of methylenes $(CH_2)_n$ where n=1,2,3,4,5,6,7,8; with PEG defined as a succession of $(CH_2—CH_2—O)_n$ where n=1,2,3,4,5,6,7,8; wherein branched is defined as a dendrimer that contains one or more of C, N, and O; wherein B is N, O or S; wherein R is selected from the group consisting of H, an organic group; a dye (e.g., ALEXA FLUOR dyes, TAMRA dyes, OREGON GREEN dyes), Lanthanide complexes, Mill contrast agents (Gd-DTPA, Gd-DOTA, Gd-DO3A); PET agents; gold nanoparticles; silver nanoparticles; quantum dots; antibiotics, antimicrobial peptides; polymers, dendrimers, and ionophores.

Figure 2:
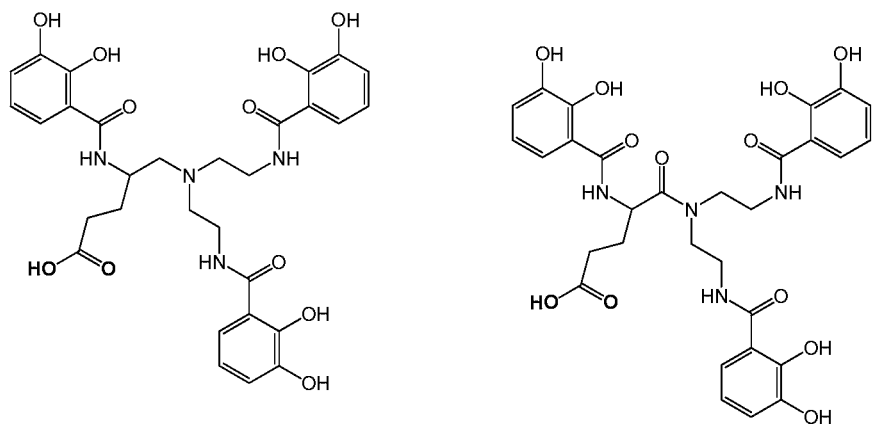
FIGS. 2 and 3 are schematic illustrations of the chemical structures of exemplary compounds and complexes as disclosed herein.
Figure 2:
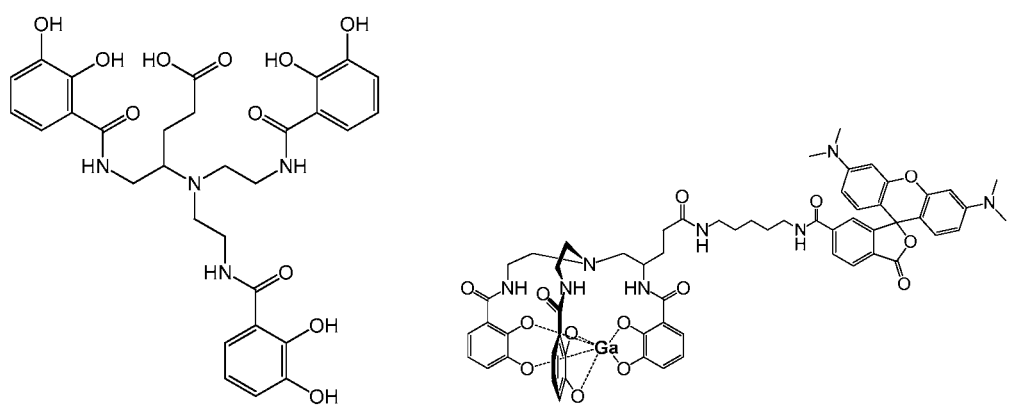
Figure 2:
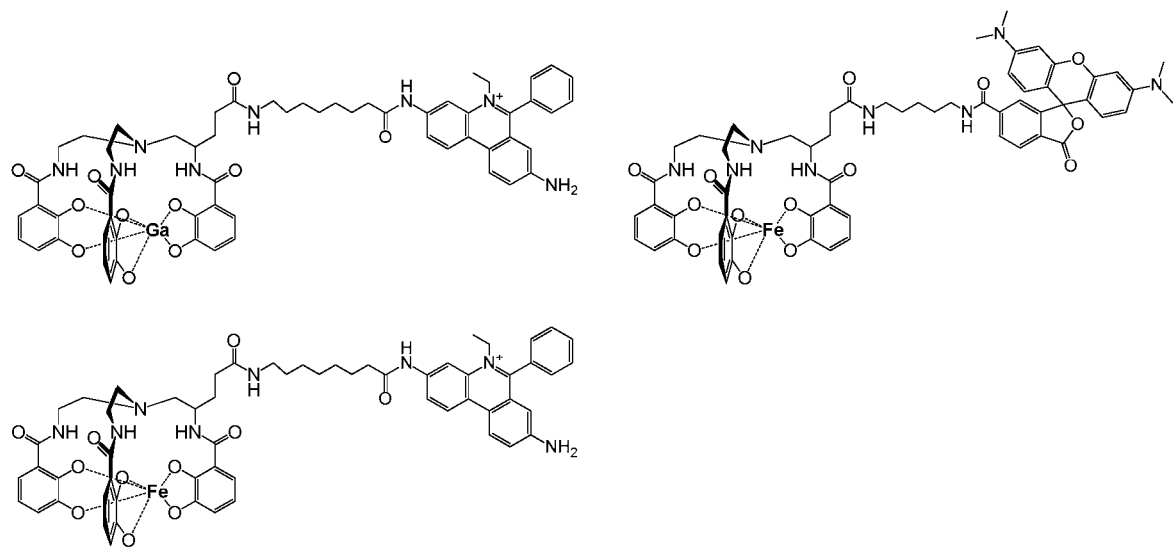

Exemplary species of Embodiment A include ligands and complexes of the formulas illustrated in FIG. 2.

Embodiment B

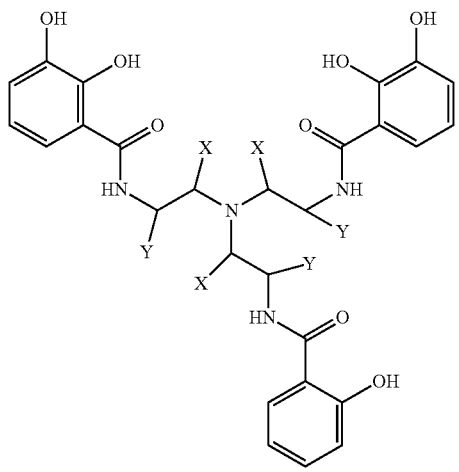

either

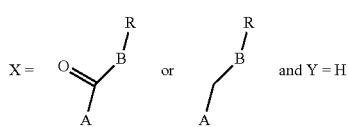

or

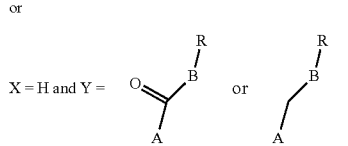

wherein A can be linear or branched, with linear including alkane or PEG chains with or without the presence of N (nitrogen), with alkane defined as a succession of methylenes $(CH2)_n$ where n=1,2,3,4,5,6,7,8; with PEG defined as a succession of $(CH_2—CH_2—O)_n$ where n=1,2,3,4,5,6,7,8; wherein branched is defined as a dendrimer that contains one or more of C, N, and O; wherein B is N, O or S; wherein R is selected from the group consisting of H, an organic group; a dye (e.g., ALEXA FLUOR dyes, TAMRA dyes, OREGON GREEN dyes), Lanthanide complexes, MRI contrast agents (Gd-DTPA, Gd-DOTA, Gd-DO3A); PET agents; gold nanoparticles; silver nanoparticles; quantum dots; antibiotics, antimicrobial peptides; polymers, dendrimers, and ionophores.

Figure 3:
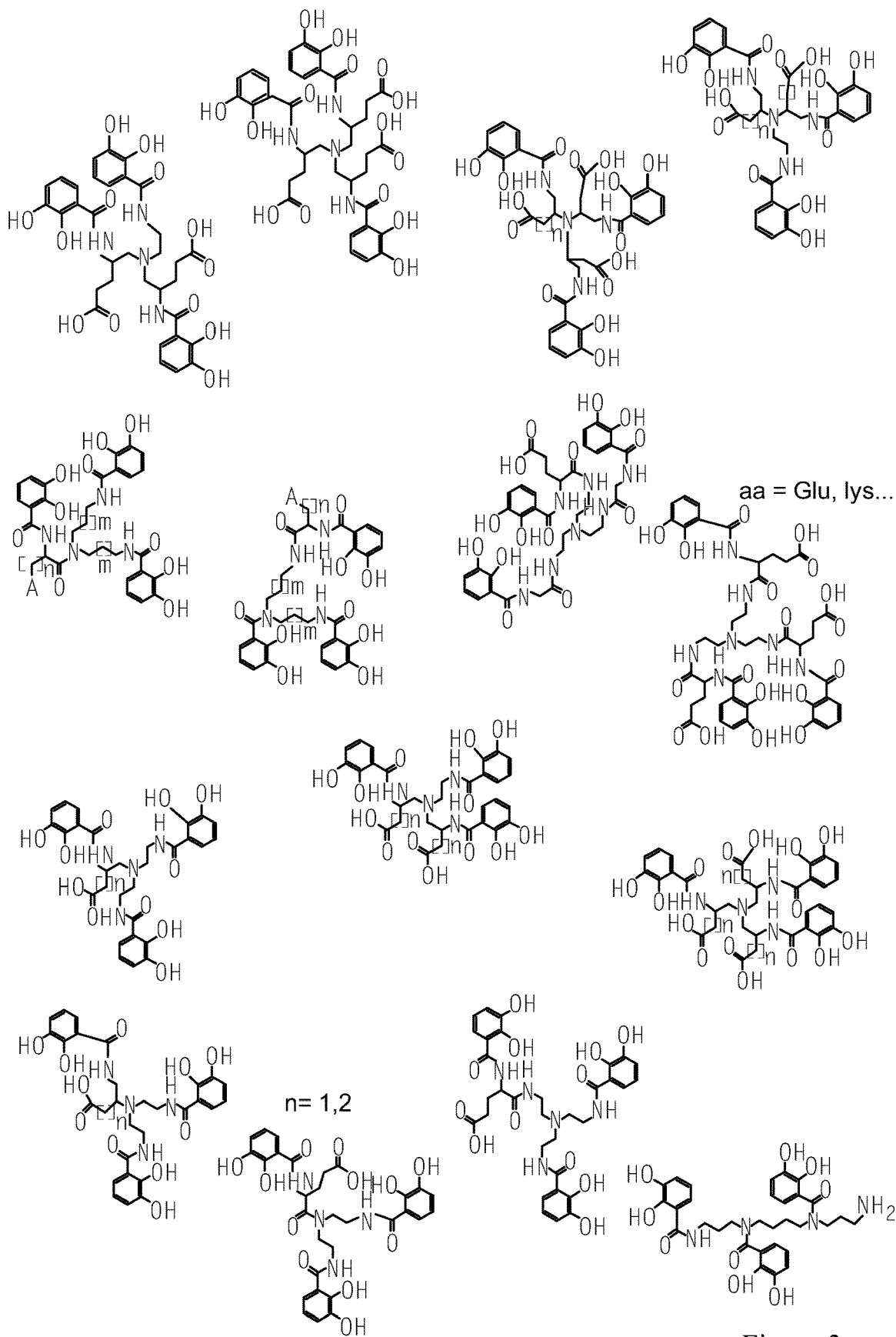

Exemplary species of Embodiment B include ligands and complexes of the formulas illustrated in FIG. 3.

The present disclosure is illustrated by the following examples. It is to be understood that the particular examples, materials, amounts, and procedures are to be interpreted broadly in accordance with the scope and spirit of the disclosure as set forth herein.

EXAMPLES

Results

General Consideration

Unless otherwise noted, starting materials were obtained from commercial suppliers and used without further purification. Water was distilled and further purified by a Millipore cartridge system (resistivity $18 \times 10^6 \Omega$). $^1H$ NMR spectra were recorded on a Varian 300 at 300 MHz or on a Bruker AX 400 at 400 MHz and $^{13}C$ NMR spectra were recorded on a Varian 300 at 75 MHz at the Le Claire-Dow Characterization Facility of the Department of Chemistry of the University of Minnesota; the solvent residual peak was used as an internal reference. $^1H$ NMR data are reported as follows: chemical shift (δ, ppm), multiplicity (s, singlet; d, doublet; t, triplet; m, multiplet), integration, coupling constant (Hz). Mass spectra (LR=low resolution; HR=high resolution; ESI MS=electrospray ionization mass spectrometry) were recorded on a Bruker BioTOF II at the Waters Center for Innovation for Mass Spectrometry Facility at the Department of Chemistry at the University of Minnesota, Twin-Cities. Analytical HPLC was performed on a Variant pro star instrument (Agilent, Santa Clara, Calif.) equipped with a diode array detector and thermostat set at 25° C., and a Zorbax Eclipse XDB-C18 column (9.4×250 mm, 5 μm, Agilent, Santa Clara, Calif.). The mobile phase of a binary gradient (Method 1: 2 minutes 2% B, 13 minutes 2 to 80% B, 2 minutes, 80% B, 3 minutes 80 to 100% B, 1 minute 100% B, Method 2: 2 minutes 5% B, 8 minutes 5 to 80% B, 3 minutes 80% B, 3 minutes 90 to 100% B, 1 minute 100%, 3 minutes 100 to 5% B 2 minutes 5% B or Method 2: 10-60% B, Method 4: 2 minutes 15% B, 20 minutes 15 to 100% B, 3 minutes, 100% B, 4 minutes 100 to 15% B, 1 minute) where A is water and B is acetonitrile at a flow rate of 1 mL/minutes was used for analytical and preparative HPLC Varian Cary Eclipse fluorescence spectrometer with temperature controlled cells, and plate reader. 384 black plate square wells, flat bottom microplates available under the trade designation CORNING 3577 from Corning.

Example 1: Ga-TREN-CAM-C2-OG

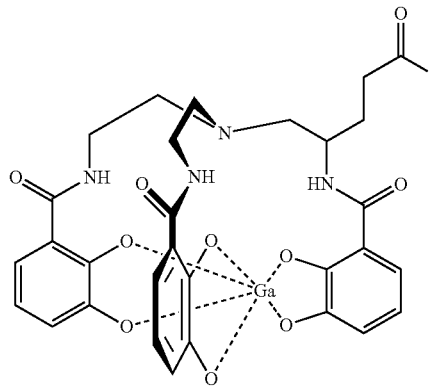
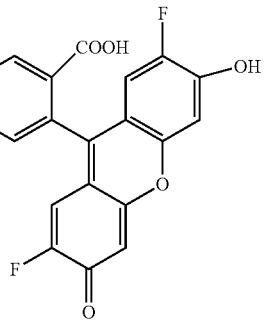

Figure 4:
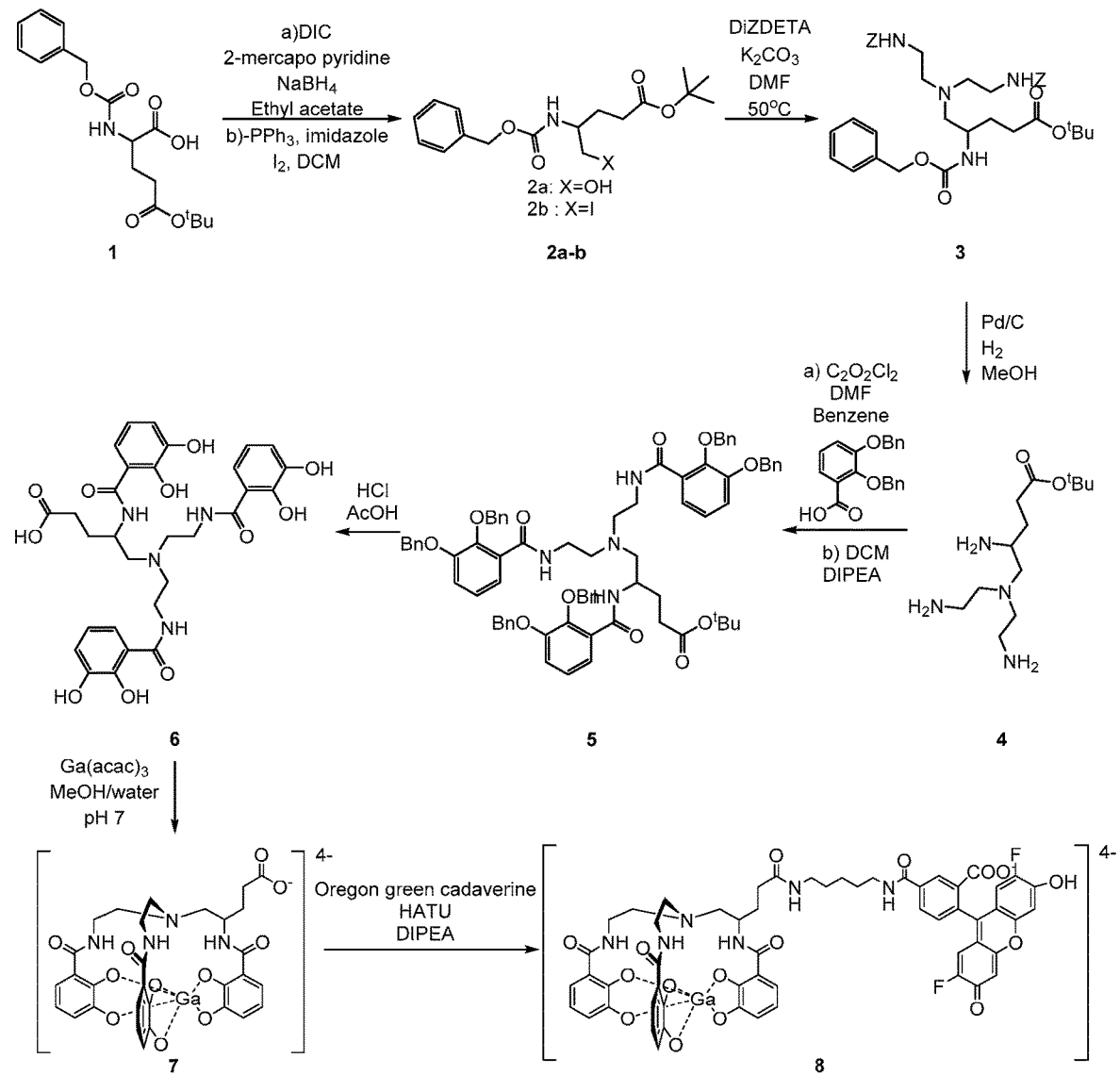
FIG. 4 is a schematic illustration of an exemplary embodiment of a synthesis of Ga-TREN-CAM-C2-OG (8).

The synthesis of TREN-CAM-C2-OG was performed in 8 steps as illustrated in FIG. 4. (Desjardins et al., *Bioorg Chem* 1998, 26 (1), 1-13). The reduction of Glu(O'Bu)COOH via a thiopyridinine ester yielded the alcohol Glu(O'Bu)OH (2a).

A Mitsunobu reaction converted the alcohol to an iodo derivative 2b (Mandal et al., *J Med Chem* 2009, 52 (19), 6126-6141). The tripodal protected cap amine (3) was then obtained by alkylation of the di-Z-protected diethylendiamine (DiZDETA) in DMF using potassium carbonate as a base. Note that the nature of the base affects the product distribution ratio, with potassium carbonate increasing the yield of the desired compound while reducing the cyclization of the iodo-derivative Glu(O'Bu)I on itself. Higher yields of the TREN cap were obtained using the iodo derivative of glutamic acid, as opposed to the bromo, chloro or triflate ones. The Z protective groups of the TREN cap were then removed by hydrogenation. The protected ligand (5) was obtained by acylation of the tripodal free amine (4) with CAM(Bn$_2$) acid.

The synthetic siderophore was deprotected in acid conditions and then complexed with gallium in neutral conditions. TREN-CAM-C2-OG (8) is obtained after coupling with OREGON GREEN dye.

2a: Z-Glu(O'Bu)OH

N,N'-diisopropylcarbodiimide (DIC, 1.38 g, 6.70 mmol, 1.13 eq.) was added to a solution of Z-Glu(O'Bu)COOH (1, 2.00 g, 5.93 mmol, 1.00 eq.) in ethyl acetate (20 mL), resulting in a precipitate. 2-Mercaptopyridine (0.720 g, 6.52 mmol, 1.10 eq.) was then added to the reaction mixture which turned yellow. After 4 hours of stirring at room temperature a precipitate was filtered out and the filtrate was concentrated under reduced pressure. The oily residue (0.300 g) was dissolved in 1,4-dioxane (10 mL) and cooled to 0° C. NaBH$_4$ (0.800 g, 21.0 mmol, 3.60 eq.) was added to the reaction mixture which was stirred for 30 minutes at 0° C. The reaction was monitored by thin layer chromatograph (TLC). The reaction mixture was then quenched with a 2% KHSO$_4$ (aq) solution and extracted with diethylether (3×100 mL). The organic phases were combined and washed with a 5% HCO$_3$ (aq) and dried with MgSO$_4$ (s). The solvent was removed under reduced pressure and the residual colorless oil was purified by flash chromatography over silica using a mixture of 30% ethyl acetate in hexanes as the eluent, yielding 2a as a white sticky solid (1.20 g, 62.8%). [M+Na]$^+$ 346 m/z, [2M+Na]$^+$ 669.3 m/z.

$^1$H NMR (300 MHz, CDCl$_3$): (δ, ppm): 1.43; (s, 9H), 1.87-1.78; (m, 2H), 2.35-2.30; (m, 2H), 3.69-3.54; (m, 3H), 5.08; (s, 2H), 5.25; (d, NH, J=9.0 Hz), 7.37-7.26; (m, 5H).

$^{13}$C NMR (75 MHz, CDCl$_3$): (δ, ppm): 26.55, 28.73, 32.66, 53.65, 65.39, 67.51, 81.59, 128.60, 128.82, 129.22, 137.05, 157.27, 174.00.

2b: Z-Glu(O'Bu)I

Iodine (2.82 g, 11.1 mmol, 3.00 eq) was added to a solution of triphenyl phosphine (2.92 g, 11.1 mmol, 3.00 eq.) and imidazole (1.26 g, 18.6 mmol, 5.00 eq.) in anhydrous dichloromethane (100 mL). The reaction mixture was stirred under N$_2$ (g) for 30 minutes after which Z-Glu(O'Bu)OH (2a, 1.20 g, 3.71 mmol, 1.00 eq.) was added. The reaction mixture was then stirred for 4 hours at room temperature.

The solvent was removed under reduced pressure and the residue was purified by flash chromatography over silica with 35% ethyl acetate in hexane as the eluent yielding 2b as a white sticky solid (1.17 g, 72.5%).

ESI-MS m/z=456.0 ([M+Na]$^+$) (Calcd. 456.0), 472.0 m/z ([M+K]$^+$) (Calcd. 472.1).

$^1$H NMR (300 MHz, CDCl$_3$) (δ, ppm)=1.40; (s, 9H), 1.82; (m, 2H), 2.28; (m, 2H), 3.28; (m, 1H), 3.36; (m, 1H), 3.50; (m, 1H), 5.06; (s, 2H), 5.17; (d, NH, J=9.0 Hz), 7.31; (m, 5H).

$^{13}$C NMR (75 MHz, CDCl$_3$) (δ, ppm)=14.87, 28.73, 30.37, 32.49, 51.13, 67.51, 81.46, 128.74, 128.84, 129.20, 136.97, 156.39, 173.01.

3: Z$_3$-TREN-C2 (O'Bu)

Di-Z-DETA (500 mg, 1.35 mmol, 1.00 eq.) and K$_2$CO$_3$ (279 mg, 2.02 mmol, 1.50 eq) were dissolved in DMF (2 mL) and heated to 80° C. for 30 minutes. Z-Glu(O'Bu)I (2b, 583 mg, 1.35 mmol, 1.00 eq) was diluted in DMF (2 mL) and added to the reaction mixture, which was heated at 80° C. for 15 hours. The solvent was removed under reduced pressure. The residue was diluted in dichloromethane (10 mL) and washed with water (2×10 mL). The organic phase was then dried with sodium sulfate. The residue was purified over reverse phase (C18) resin using a gradient of CH$_3$CN in water to yield the protected TREN cap 3 as an oil. The solvent was removed under reduced pressure. The residue was diluted in dichloromethane (10 mL) and washed with water (2×10 mL). The organic phase was then dried with sodium sulfate. The residue was purified by flash chromatography (silica) using a gradient of (0 to 4%) methanol in DCM (0.163 g, 18%).

ESI-MS m/z=[M+H]$^+$ 677.4 m/z (Calcd. 677.3), [M+K]$^+$ 715 m/z (Calcd. 715).

¹H NMR (400 MHz, CDCl₃) (δ, ppm)=1.40; (s, 9H), 1.43; (t, 2H, J=8.0), 2.28-2.26; (m, 2H), 2.35; (m, 1H) 2.48-2.45; (m, 3H), 2.60; (m, 2H), 3.22; (m, 4H), 5.11; (m, 1H), 5.30; (s, 6H), 7.26; (m, 15H).

¹³C NMR (400 MHz, CDCl₃) (δ, ppm)=172.9, 162.7, 157.1, 141.17, 136.7, 136.5, 128.7, 128.5, 128.4, 128.4, 128.1, 128.0, 127.9, 127.8, 127.4, 126.9, 80.6, 79.5, 77.3, 64.99, 53.4, 50.5, 36.5, 29.7, 28.5, 28.0.

4: TREN-C2-(O$^t$Bu)

A speck of Pd/C was added to a solution of Z₃-TREN-C2 (O$^t$Bu) (3, 0.250 g, 0.369 mmol) in methanol (1 mL). The reaction mixture was placed in a Parr hydrogenator which was charged with H₂ (g) to 50 psi. The Pd/C was filtered and the solvents removed under reduced pressure to yield the cap 4 as an oil (119 mg, quantitative).

ESI-MS m/z=275.2 m/z ([M+H]⁺) (Calcd. 275.4).

¹H NMR (400 MHz, CD₃OD) (δ, ppm)=1.45; (s, 9H), 1.86-1.93; (m, 4H), 2.17; (m, 1H), 2.55; (m, 3H), 2.74; (m, 4H), 2.97; (m, 2H).

¹³C NMR (100.62 MHz, CD₃OD) δ 172.12, 80.79, 56.75, 51.38, 50.84, 49.17, 36.98, 34.09, 30.79, 29.51, 27.01 ppm.

5: TREN-C2-CAM(Bn)

TREN C2 (4, 20.0 mg, 0.073 mmol, 1 eq) and CAM thiaz (95.0 mg, 0.218 mmol 3 eq), were dissolved in DCM (7 mL) and DIPEA (100 mg, 0.774 mmol, 10.6 eq) for 5 days. The solvent was removed and the residue purified by flash chromatography silica and a gradient of methanol in DCM (26.0 mg, 29.1%).

ESI-MS m/z=[M+H]⁺ 1223.5 m/z (Calcd. 1223.5) [M+Na]⁺ 1245.5 m/z (Calcd. 1245.5).

¹H NMR (CDCl₃, 400 MHz): δ 7.77-7.03; (m, 39H), 5.12; (m, 12H), 4.0; (m, 1H), 3.29-2.09; (m, 11H), 1.70; (m, 1H), 1.43; (m, 2H), 1.38; (s, 9H).

¹³C NMR (100.62 MHz, CD₃OD): δ 172.4, 165.5, 151.7, 151.5, 146.8, 146.7, 136.6, 136.6, 136.5, 136.4, 129.3, 128.9, 128.8, 128.8, 128.7, 128.7, 128.6, 128.6, 128.5, 128.4, 128.2, 128.1, 127.8, 127.6, 127.5, 125.0, 124.5, 124.2, 124.1, 123.2, 123.0, 119.0, 116.9, 116.7, 80.1, 77.2, 76.2, 76.1, 71.6, 71.3, 71.2, 58.2, 53.4, 50.9, 37.1, 32.2, 29.7, 28.0.

6: TREN-C2-CAM

TREN-C2-CAM(Bn) (5, 10.3 mg, 84.2 μmol) was diluted in AcOH (1 ml) and HCl (1 mL). The solution was stirred for 4 days. The solvent was removed using the schlenk line. DCM (2 mL) was added then removed with rotavap twice. Then methanol (2 mL) was added and removed with the rotavap (3.19 mg, 60%).

ESI-MS m/z=[M+H]⁺ 627.5 m/z (Calcd. 627.2) [M+(MeOH)₂]⁺ 691.5 m/z (Calcd. 691.3),) [M+Na]⁺ 649.5 m/z (Calcd. 649.2).

¹H NMR MeOD 400 MHz: δ 7.35; (3H, dd, 1.2 Hz, 8.0 Hz), 7.01; (3H, dd, 1.6 Hz, 8.0 Hz), 6.74; (3H, t, 8.0 Hz), 4.65; (1H, m), 3.85-3.55; (4H, m), 3.24-2.6; (4H, m), 2.46-2.1; (2H, m), 1.8-1.45; (2H, m). ¹³C NMR MeOD 400 MHz: δ 181.9, 172.5, 150.3, 145.5, 120.4, 120.1, 118.3, 112.7, 61.19, 59.96, 46.11, 23.96, 17.3.

Figure 5:
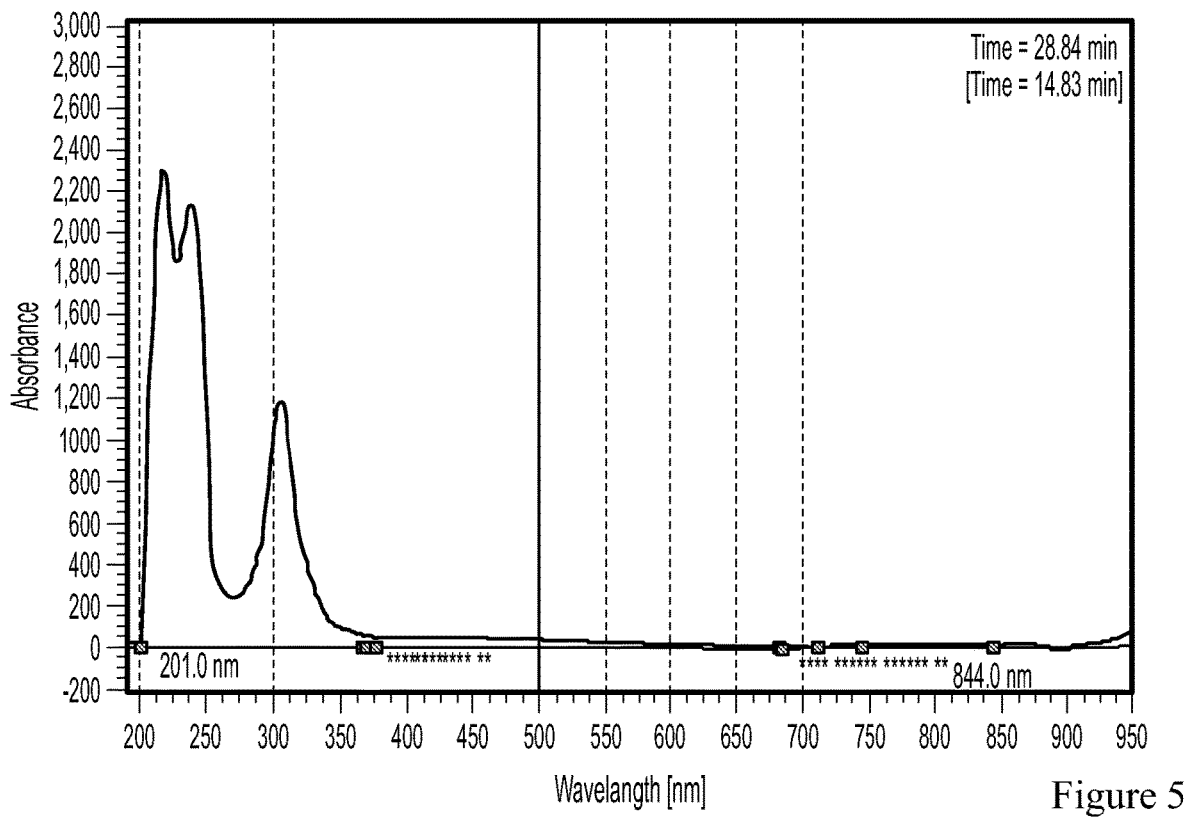
FIG. 5 is an illustration of a UV-Visible absorbance spectrum of TREN-C2-CAM.

A UV-Visible absorbance spectrum of TREN-C2-CAM is illustrated in FIG. 5.

7: Ga-TREN-C2-CAM

A solution of Ga(acac)₃ (6, 1.0 mg, 2.8 μmol 1 eq) in methanol (0.5 ml) was added to a solution of TREN-C2-CAM (1.7 mg, 2.8 μmol, 1 eq). pH was adjusted to 7 with a drop of KOH in methanol 0.5 M. (1.3 mg, 75%).

8: Ga-TREN-CAM-C2-OG

Ga-TREN-C2-CAM (7, 1.3 mg, 2.1 mmol, 1 eq), OREGON GREEN (OG) dye (1.0 mg, 2.1 mmol, 1 eq) 1-Ethyl-3-(3-dimethylaminopropyl)carbodiimide (EDC) (0.5 mg, 2.4 mmol, 1. Eq.) were dissolved in DMF (1 mL). Reaction was stirred at room temperature for two days. The solvent was speed vacuumed and the residue was purified by C18 using a gradient of CH₃CN in water. Fraction two led to a 30 μM solution (3.6 ml).

Figure 6:
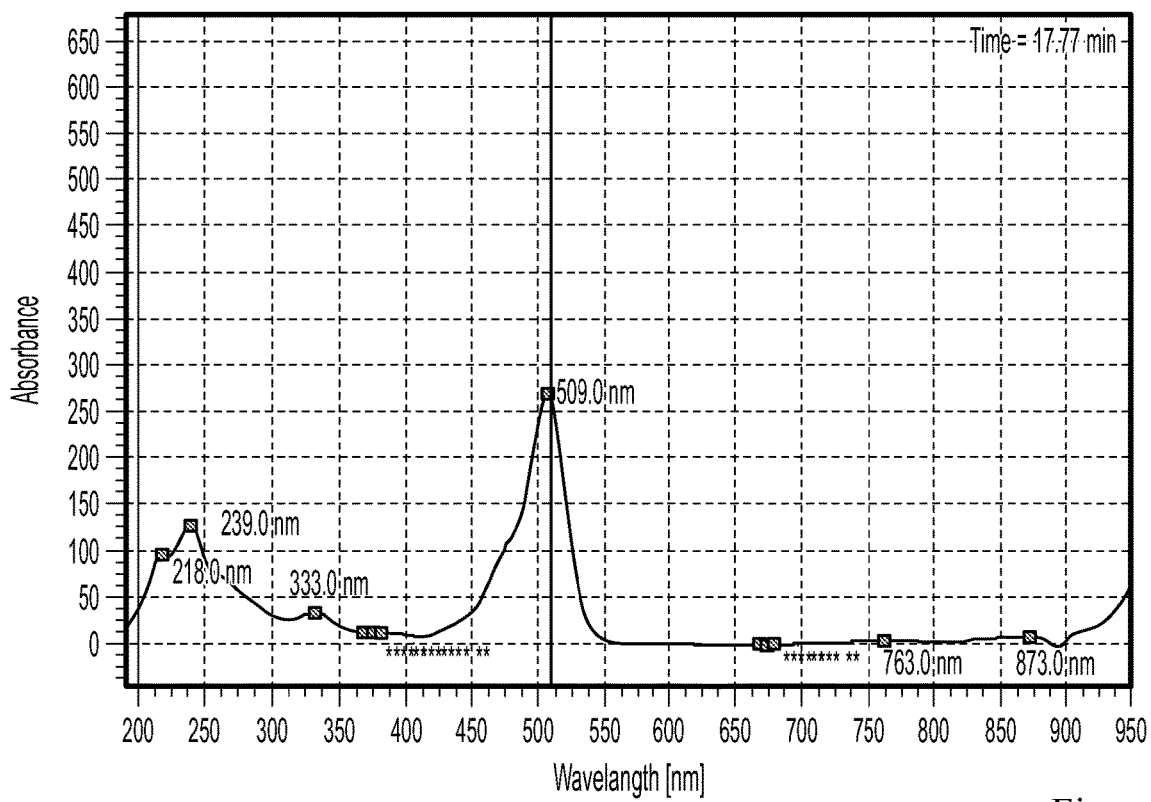
FIG. 6 is an illustration of a UV-visible spectrum of the final probe, Ga-TREN-C2-CAM-OG.

A UV-visible spectrum of the final probe, Ga-TREN-C2-CAM-OG is illustrated in FIG. 6.

Example 2: Ga-TREN-GlyCAM-GluCAM-OG

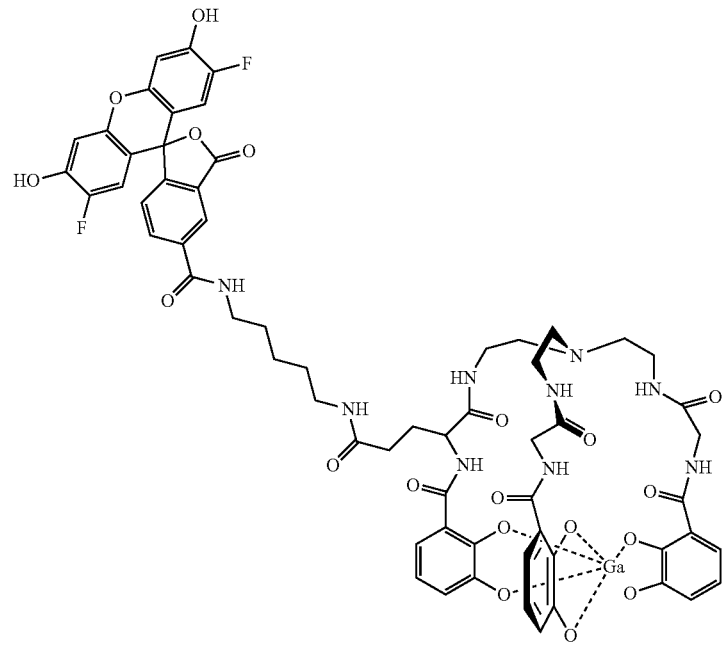

Figure 7:
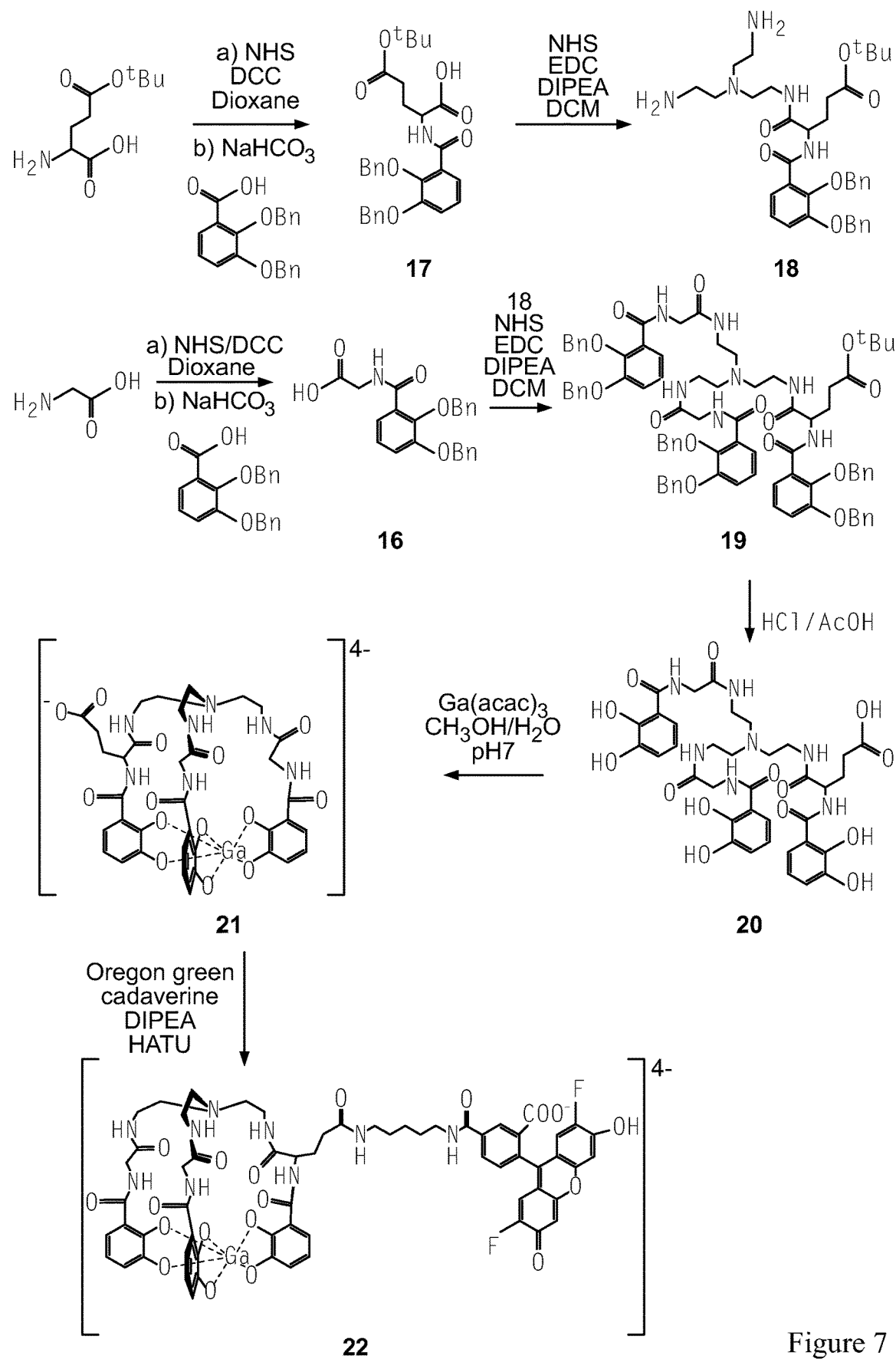
FIG. 7 is a schematic illustration of an exemplary embodiment of a synthesis of Ga-TREN-GlyCAM-GluCAM-OG (22).

The synthesis of Ga-TREN-GlyCAM-GluCAM-OG (22) is illustrated in FIG. 7. The intermediates 16 and 17 were synthesized as described in the literature (Bergeron et al., *Journal of Organic Chemistry* 1981, 46 (22), 4524-4529). The synthesis of Ga-TREN-GlyCAM-GluCAM-OG is performed in 6 overall steps as follows. The TREN cap was first mono substituted with Glu-CAM(Bn) (18), after which the other two Gly-CAM(Bn) arms were added. Removal of all protective groups was performed under acidic conditions. Subsequently the metal complex was formed and coupled to the OREGON GREEN dye.

16: Gly-CAM(Bn)

CAM(Bn) (502 mg, 1.50 mmol) and NHS (208 mg, 1.81 mmol) were disolved in 5 mL of 1,4-dioxane. The crude obtained was cooled down to 11° C., and then DIC (238.5 mg, 1.89 mmol) was added. The system was magnetically stirred at room temperature for 24 hours. Next, a mixture of $NaHCO_3$ (120 mg, 1.43 mmol) and Glycine (134 mg, 1.79 mmol) disolved in 2 mL of 1,4-dioxane were added to the crude. The suspension obtained was magnetically stirred at room temperature under $N_2$ gas. After 22 hours, 6 mL of water were added. 3 hours later, the solvent was reduced to ⅓ its original volume. Then, HCl 1 M was dropwise added until pH 2 was reached. The product was extracted form the crude via liquid-liquid extraction using DCM and water as solvents. The organic phase was collected and dried over $Na_2SO_4$, the solvent evaporated and the yellowish oil applied to a silica gel column and subsequently eluted with MeOH (1-8%) in DCM. (249.5 mg, 42%).

$^1$H-NMR (400 MHz, $CD_2Cl_2$) δ 4.05; (d, 2H, $CH_2$), 5.13; (s, 2H, $CH_2$), 5.16; (s, 2H, $CH_2$), 7.17; (m, 2H, ArH), 7.28; (m, 3H, ArH), 7.39; (m, 5H, ArH), 7.48; (m, 2H, ArH), 7.63; (dd, 1H, ArH), 8.48; (t, 1H, NH).

17: Glu-CAM(Bn)

A solution of 1-ethyl-3-(3-dimethylaminopropyl)carbodiimide (EDC, 343 mg, 7.63 mmol, 1.20 eq.) in 1,4-dioxane (2.2 mL) was added dropwise to a solution of $CAM(Bn_2)$ (500 mg, 1.49 mmol, 1.00 eq.) and N-hydroxysuccinimide (NHS, 206 mg, 1.79 mmol, 1.20 eq.) in 1,4-dioxane (2 mL) and cooled to 4° C. The solution was allowed to return to room temperature and stirred at room temperature for 16 hours. The crude reaction mixture was filtered. A solution of glutamic-γ-tertbutylester (395 mg, 1.94 mmol, 1.30 eq.) and sodium bicarbonate (163 mg, 1.94 mmol, 1.30 eq.) in water (8 mL) was added to the yellowish filtrate. The reaction mixture was stirred at room temperature for 47 hours. The reaction mixtue was then concentrated under reduced pressure and the pH was ajusted to 2 by addition of an aqueous solution of HCl (1 M). A white precipitate was formed and collected by filtration. The precipitate was purified by flash chormatography over silica using a gradient of 1% to 5% methanol in dichloromethane yielding the product 17 as a white sticky powder (363 mg, 46.7%).

$^1$H NMR (400 MHz, $CD_3OD$) (δ, ppm)=1.42 (s, 9H), 1.84; (m, 1H), 2.23; (m, 1H), 2.25; (m, 2H), 4.59; (m, 1H), 5.22; (s, 4H), 7.53-7.16; (m, 13H).

18: TREN-Glu-CAM(Bn)

Glu-CAM(Bn) (17, 311 mg, 0.600 mmol) was dissolved in 10 mL of 1,4-dioxane, followed by the addition of NHS (83.4 mg, 0.720 mmol). EDC.HCl (140 mg, 0.730 mmol) dissolved in 10 mL of 1,4-dioxane was then dropwise added under $N_2$ gas atmosphere to the mixture Glu-CAM(Bn)/NHS which had been previously cooled down to 9° C. The crude of the reaction was allowed to reach room temperature (25-27° C.) and then magnetically stirred under $N_2$ gas for 27 hours. Next, the crude obtained was slowly added via canula to a mixture of TREN (511 mg, 3.49 mmol) and DIPEA (1.36 g, 10.5 mmol) in 6 mL of 1,4-dioxane. The solution obtained was magnetically stirred at room temperature for 65 hours and after that time the solvent was evaporated. The yellowish oil obtained was dissolved in 70 mL of DCM and then washed three times with water (20 mL per wash). The organic phase was collected and dried over $Na_2SO_4$. The solvent was evaporated, and then the yellowish oil observed (mixed with a white solid) was isolated by extracting the oil in a minimum amount of DCM. Finally, the DCM is evaporated and the yellowish oil was recovered (0.3345 g, 86%).

$^1$H-NMR (400 MHz, MeOD): δ 1.44; (s, 9H, $CH_3$), 1.74; (m, 1H, $CH_2$), 2.06; (m, 1H, $CH_2$), 2.25; (m, 2H, $CH_2$), 2.50-2.82; (m, 12H, $CH_2$), 3.18-3.59; (m, 4H, $NH_2$), 4.62; (m, 1H, CH), 5.11-5.27; (m, 12H, $CH_2$), 7.13-7.50; (m, 13H, ArH), 7.67; (m, 1H, NH), 8.57; (dd, 1H, NH).

MS (ESI-): m/z ([M–H]$^-$ calcd 646.36 obsd 646.3, 647.3, 648.3.

19: TREN-Glu-CAM(Bn) Gly-CAM(Bn)

CAM(Bn)-Gly (16, 90.3 mg, 0.230 mmol) and NHS (34.9 mg, 0.300 mmol) were dissolved in 2 mL of 1,4-dioxane at room temperature. Once everything was dissolved, the solution obtained was cooled down until it reached 13° C. Next, EDC.HCl (58.9 mg, 0.310 mmol) dissolved in 2 mL of 1,4-dioxane, was added dropwise. Once all the EDC.HCl was added, the system was allowed to slowly warm up until it reached room temperature and then magnetically stirred for 96 hours under $N_2$ atmosphere. The dioxane was then evaporated and the yellowish oil obtained was mixed with DIPEA (149 mg, 1.15 mmol) and TREN-[Glu-O-t-Butyl-CAM(Bn)] (18, 53.8 mg, 0.0800 mmol) in 3 mL of dichloromethane. The resulting mixture was magnetically stirred at room temperature for 73 hours under nitrogen atmosphere. The crude obtained was diluted in a total of 30 mL of DCM and then washed with 10 mL of water (three times). The organic phase was collected and dried over $Na_2SO_4$, then the DCM was evaporated under reduced pressure and the yellowish oil obtained was applied to a silica gel column and eluted with MeOH (0-5%) in dichloromethane (19.0 mg, 17%).

$^1$H-NMR (400 MHz, $CD_2Cl_2$) δ 1.36; (m, 9H, $CH_3$), 1.69; (m, 1H, $CH_2$), 1.94; (m, 1H, $CH_2$), 2.16; (m, 2H, $CH_2$), 2.40-2.58; (m, 6H, $CH_2$), 2.97-3.40; (m, 6H, $CH_2$), 3.89; (m, 4H, $CH_2$), 4.49; (m, 1H, CH), 5.04-5.17; (m, 12H, $CH_2$), 7.05-7.60; (m, 39H, ArH), 8.49; (m, 3H, NH).

$^{13}$C-NMR (100 MHz, $CD_2Cl_2$) δ 27.78, 31.82, 38.22, 43.65, 54.43, 71.21, 76.00, 76.08, 80.09, 117.02, 122.63, 122.71, 124.27, 127.18, 127.80, 127.93, 128.16, 128.22, 128.40, 128.44, 128.47, 128.57, 128.59, 129.19, 136.37, 136.48, 136.50, 136.58, 146.87, 151.96, 165.38, 165.71, 169.24, 171.38, 171.84.

MS (ESI+): m/z [M+H]$^+$ calcd 1394.6 obsd 1394.7, [M+Na]$^+$ calcd 1416.6 obsd 1416.7.

20: TREN-[Glu-CAM][Gly-CAM]$_2$

TREN-[Glu-O-t-Butyl-CAM(Bn)][Gly-CAM(Bn)]2(19, 15.8 mg, 0.0110 mmol) was dissolved first in 1 mL of glacial acetic acid. Once everything was dissolved, 1 mL of HCl 37% was added. The reaction mixture obtained was magnetically stirred at room temperature for 27 hours under nitrogen atmosphere. After this time, the solvent was evaporated and the yellowish paste obtained was mixed with 2 mL of methanol that was subsequently rota-evaporated (this process was repeated three times) (8.1 mg, 90%).

$^1$H-NMR (400 MHz, MeOD) δ 2.08; (m, 1H, $CH_2$), 2.24; (m, 1H, $CH_2$), 2.45; (m, 2H, $CH_2$), 3.47-3.69; (m, 12H, $CH_2$), 4.06; (m, 4H, $CH_2$), 4.57; (m, 1H, CH), 6.73; (m, 3H, ArH), 6.94; (td, 3H, ArH), 7.28; (m, 3H, ArH).

MS (ESI-): m/z [M−H]⁻ calcd 796.28 obsd 796.3, 797.3.

21: Ga-TREN-[Glu-CAM][Gly-CAM]₂

TREN-[Glu-CAM] [[Gly-CAM]₂ (20, 6.3 mg, 79 μmol) was dissolved in 500 μL of MeOH yielding a yellowish solution. Next, the reaction flask was degassed and 500 μL of a methanolic solution of NaOH 15.5 mM (77.5 μmol) were added. The pinkish solution obtained was magnetically stirred at room temperature for a few minutes. Then, Ga(acac)₃ (3.1 mg, 85 μmol) dissolved in 500 μL of MeOH was added. The crude obtained from the reaction was degassed and magnetically stirred at room temperature for 18 hours. After this time, the volume of the crude obtained was reduced to 1/10 its original volume, and then 1 mL of ether was added. The precipitated metal complex was isolated by centrifugation; the supernatant obtained was discarded and the solid obtained was isolated and dried under reduced pressure at 40° C. (6.2 mg, 91%).

Figure 8:
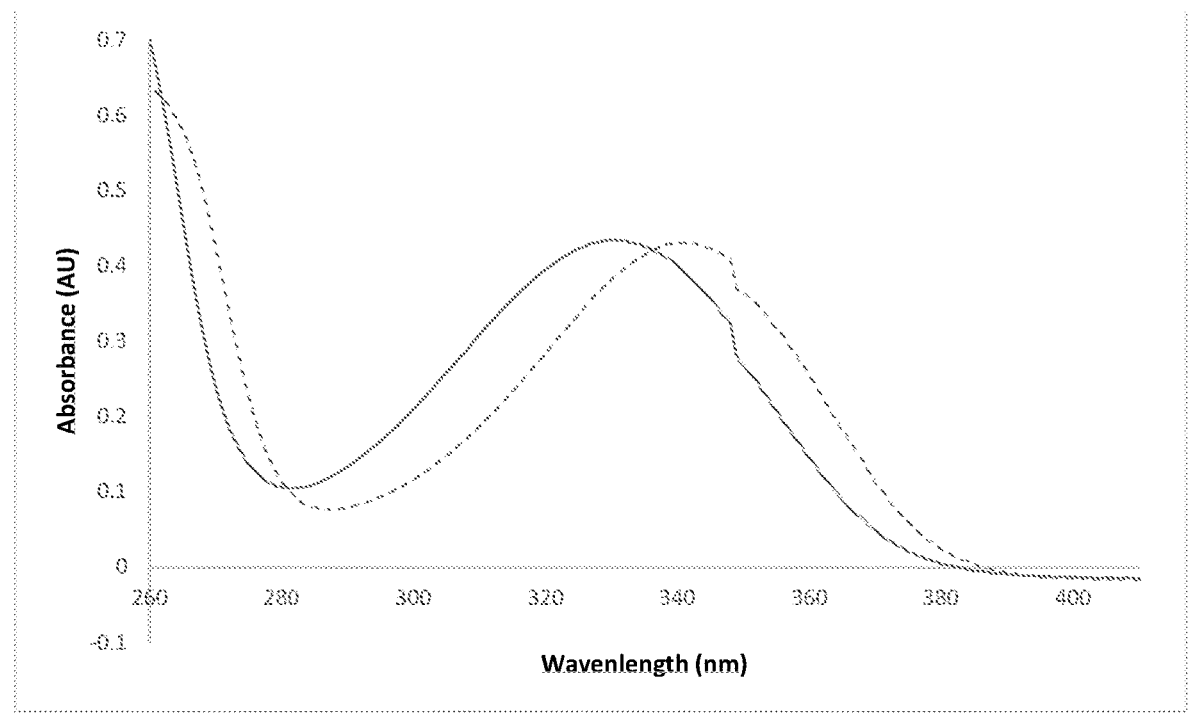
FIG. 8 is an illustration of a UV-visible spectra of TREN-[Glu-CAM]-[Gly-CAM]2 (-) and Ga-TREN-[Glu-O-t-Butyl-CAM]-[Gly-CAM]2 (---) in TRIS buffer pH 7.4 (94 mM and 90 mM respectively).

UV-visible spectra of TREN-[Glu-CAM]-[Gly-CAM]₂ (-) and Ga-TREN-[Glu-O-t-Butyl-CAM]-[Gly-CAM]₂ (---) in TRIS buffer pH 7.4 (94 mM and 90 mM respectively) are illustrated in FIG. 8.

22: Ga-TREN-GlyCAM-GluCAM-OG

Ga-TREN-[Glu-O-t-Butyl-CAM][Gly-CAM]₂ (21, 1.8 mg, 18 μmol), OREGON GREEN 488 Isomer 5 dye (1.1 mg, 22 μmol), EDC.HCl (0.5 mg, 26. μmol) and DMAP (catalytic amount) were dissolved in 1200 μL of anhydrous DMF. The reaction mixture obtained was shook at room temperature for 13 days. Next, the DMF was evaporated and the orange solid obtained was resuspended in a mixture of DMF 18% (v/v) and MeOH 7% (v/v) in water, then applied to a C-18 reversed phase silica gel column and eluted with acetonitrile (10-60%) in water. Yield: 1.3%

Figure 9:
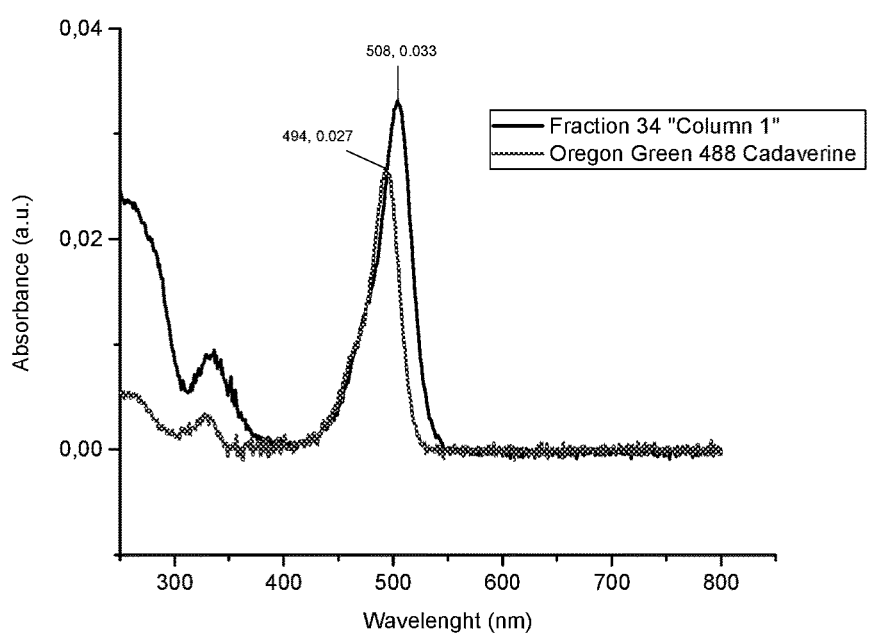
FIG. 9 is an illustration of a UV-visible spectra of Ga-TREN-GlyCAM-GluCAM-OG ($\lambda_{max}$508) and OREGON GREEN 488 CADAVERINE dye ($\lambda_{max}$ 494) in TRIS buffer pH 9.06.

UV-visible spectra of Ga-TREN-GlyCAM-GluCAM-OG ($\lambda_{max}$ 508) and OREGON GREEN 488 CADAVERINE dye ($\lambda_{max}$ 494) in TRIS buffer pH 9.06 are illustrated in FIG. 9.

Example 3: Ga-TREN-GluCAM-OG

Figure 10:
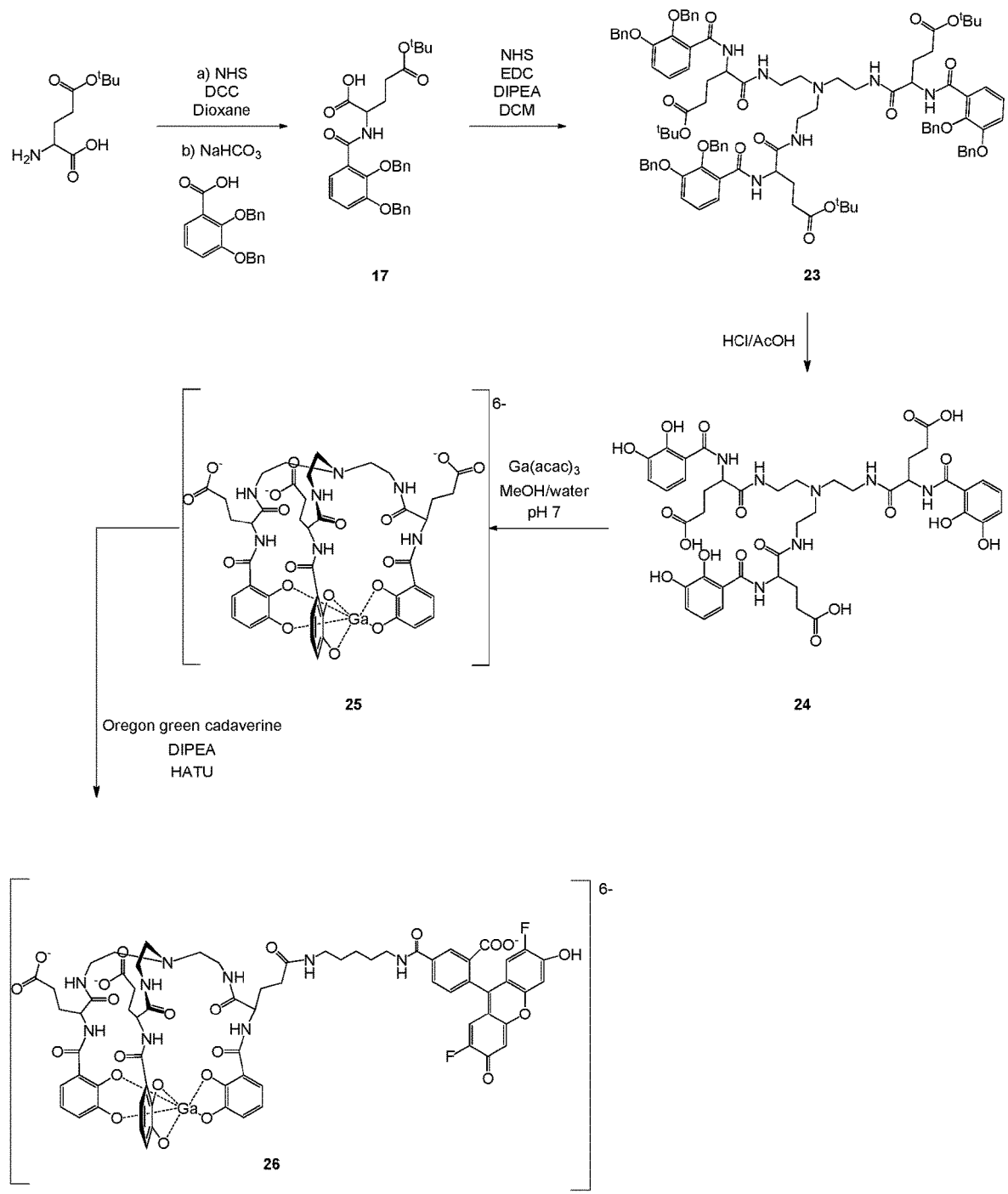
FIG. 10 is a schematic illustration of an exemplary embodiment of a synthesis of Ga-TREN-GluCAM-OG (26).

The synthesis of Ga-TREN-GluCAM-OG (26) is illustrated in FIG. 10.

23: TREN-tris-Glu-CAM(Bn)

Glu-CAM(Bn) (17, 287.4 mg, 0.550 mmol) and NHS (78.0 mg, 0.68 mmol) were dissolved in 7 mL of 1,4-dioxane under N₂ gas. Then, the reaction flask was cooled down to 12° C., and EDC.HCl (129 mg, 0.670 mmol) was added. The crude obtained from the reaction was magnetically stirred at room temperature under N₂ atmosphere for 19 hours. Next, DIPEA (338 mg, 2.62 mmol) and TREN (6.9 mg, 0.050 mmol) were mixed and added to the crude. The reaction was magnetically stirred at room temperature under N₂ gas for 19 hours and after this time, a second portion of TREN (9.4 mg, 0.060 mmol) was added. After 1 hour, the final portion of TREN (8.3 mg, 0.057 mmol) was added and the crude was magnetically stirred for 17 additional hours. The solvent of the crude was evaporated under reduced pressure, the yellowish oil obtained was dissolved in 40 mL of DCM and then washed with 30 mL of water (this process was carried out three times). The organic phase was collected and dried over Na₂SO₄ overnight. Then, the solvent was evaporated under reduced pressure yielding a yellowish sticky oil. The oil was applied to a column and then eluted with a gradient of MeOH (0-7%) in DCM (121.0 mg, 44%).

¹H-NMR (400 MHz, CD₂Cl₂): δ 1.39; (s, 27H, CH₃), 1.73; (m, 3H, CH₂), 1.99; (m, 3H, CH₂), 2.18; (m, 6H, CH₂), 2.38-3.44; (m, 12H, CH₂), 4.57; (m, 3H, CH), 5.10; (m, 12H, CH₂), 7.02-7.56; (m, 39H, ArH), 7.58-7.73; (m, 3H, NH), 8.51; (m, 3H, NH).

MS (ESI+): m/z [M+Na]⁺ calcd 1672.79 obsd 1673.1.

24: TREN-Glu-CAM

TREN-[Glu-CAM(Bn)]3 (23, 121 mg, 0.0732 mmol) was dissolved in 1 mL of glacial acetic acid. Once everything was dissolved, 1 mL of concentrated HCl was added to the crude of reaction. The crude was magnetically stirred under N₂ atmosphere for 16 hours. After this time, the solvent was removed under vacuum. The yellowish oil obtained was dried 4 hours under vacuum (72.0 mg, 100%).

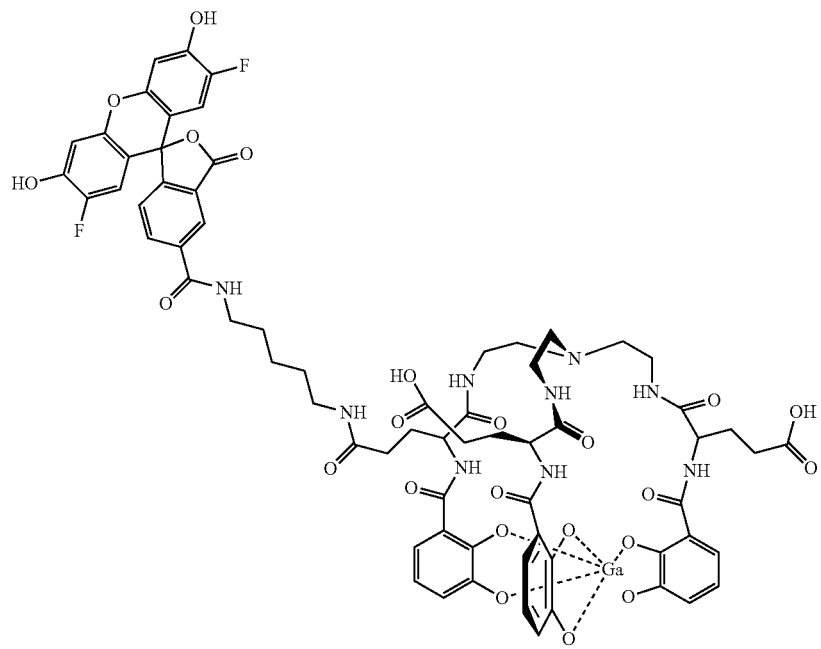

$^1$H-NMR (400 MHz, MeOD): δ 2.09; (s, 3H, CH$_2$), 2.24; (s, 3H, CH$_2$), 2.48; (m, 6H, CH$_2$), 3.48-3.65; (m, 12H, CH$_2$), 4.55; (s, 3H, CH), 6.74; (m, 3H, ArH), 6.95; (m, 3H, ArH), 7.31; (m, 3H, ArH).

25: Ga-TREN-tris-Glu-CAM

TREN-[Glu-CAM]3 (5.1 mg, 5.2 µmol) was dissolved in 500 µL MeOH and mixed with 31 µL of methanolic KOH 0.5M (15.5 µtmol). Next, Ga(acac)$_3$ (1.9 mg, 5.2 µmol) was added. After 24 hours shaking at room temperature, the solvent was evaporated and then the off-white solid was resuspeded in 0.2 mL of MeOH, Then, 1 mL of ether was added, the solution obtained was shaken and the suspension obtained was centrifuged for 5 minutes at 12000 rpm. The supernatant was removed and the off-white solid was collected. (3.8 mg, 64%).

Figure 11:
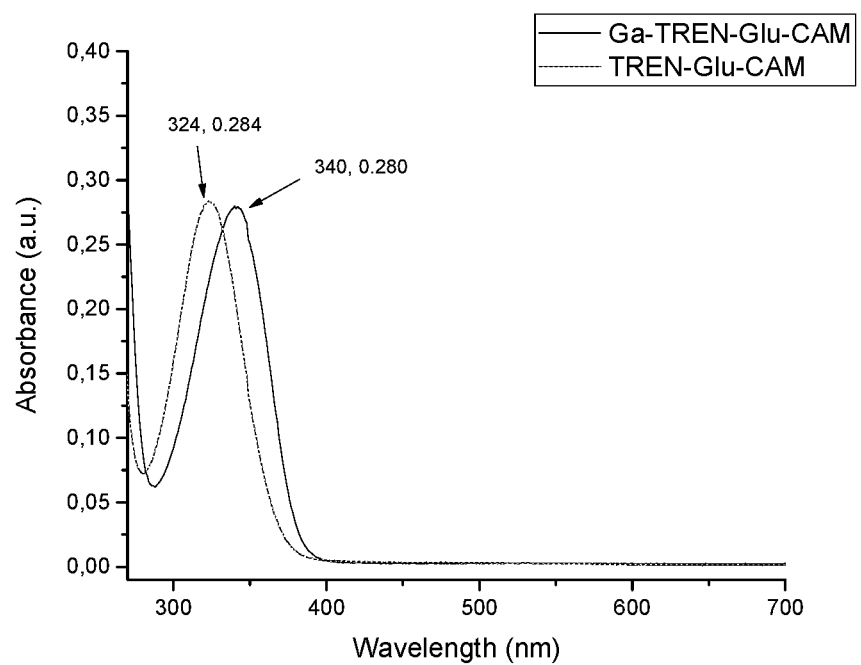
FIG. 11 is an illustration of a UV-visible spectra of fraction Ga-TREN-Glu-CAM ($\lambda_{max}$ 340) and TREN-Glu-CAM ($\lambda_{max}$ 324) in TRIS buffer 93 mM pH 7.45 are illustrated.

UV-visible spectra of fraction Ga-TREN-Glu-CAM ($\lambda_{max}$ 340) and TREN-Glu-CAM ($\lambda_{max}$ 324) in TRIS buffer 93 mM pH 7.45 are illustrated in FIG. 11.

26: Ga-TREN-GluCAM-OG

Ga-TREN-[Glu-CAM]3 (2.7 mg, 2.4 mol), OREGON GREEN CADAVERINE 488 dye (1.2 mg, 2.4 mol), EDC.HCl (0.6 mg, 3 mol) and DMAP (catalytic amount) were dissolved in 1 mL of anhydrous DMF. The orange crude obtained was shaken at room temperature for 5 days. After this time, the solvent was evaporated under reduced pressure. The orange solid obtained was dissolved in a mixture of 6.6% ACN and 3.3% of DMF, applied to a C-18 reversed-phase silica column and then eluted with 100 mL 6.6% ACN and 3.3% DMF in water, then 50 mL 20% ACN, 50 mL 50% ACN, 50 mL 60% ACN, 50 mL 80% ACN, 50 mL MeOH, 50 mL H$_2$O, 50 mL 20% ACN, 50 mL 20% ACN, 50 mL 50% ACN, 50 mL H$_2$O and 100 mL MeOH respectively. Yield: 2.2%

Figure 12:
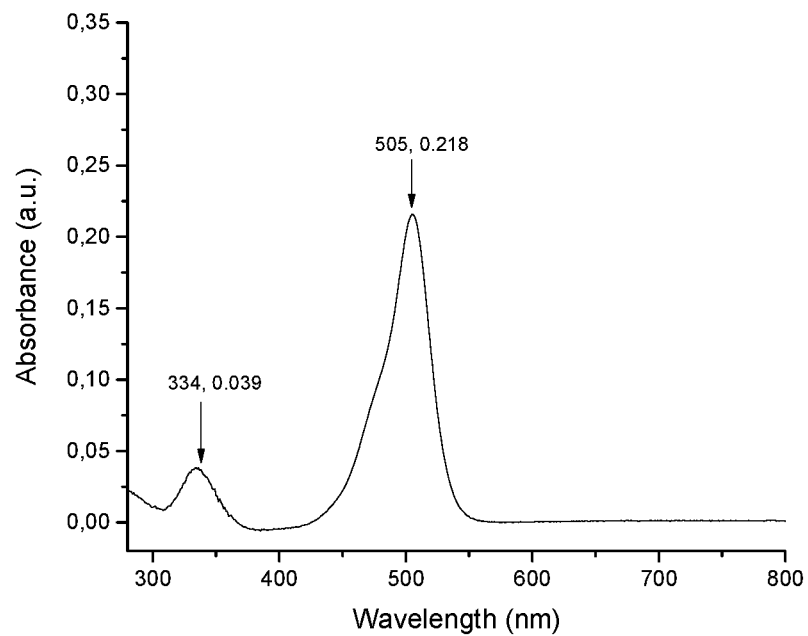
FIG. 12 is an illustration of a UV-visible absorbance spectrum of Ga-TREN-GluCAM-OG (36) in TRIS buffer pH 9.06.

A UV-visible absorbance spectrum of Ga-TREN-Glu-CAM-OG (36) in TRIS buffer pH 9.06 is illustrated in FIG. 12.

Example 4: Ga-3,3-LiCAM-GluCAM-OG romethane (100 mL) and extracted with water (3×100 mL). The organic phase was dried with sodium sulfate. Removal of the solvent under reduced pressure yielded the intermediate as an off white foam that was used immediately in the next step.

$^1$H NMR (400 MHz, CDCl$_3$) (δ, ppm)=7.95; (m, 2H), 7.39-7.19; (m, 20H), 7.05; (m, 4H), 5.06; (s, 4H), 4.98; (s, 4H), 3.24; (dt, 2H, J$_1$=6.8 Hz, J$_2$=5.6 Hz), 2.35; (td, 4H, J$_1$=7.0 Hz, J$_2$=5.6 Hz), 1.42; (tt, J$_1$=6.8 Hz, J$_2$=6.8 Hz).

33: Symmetric-3,3-Li-Glu-CAM(Bn)

Diisopropylethylamine (DIPEA, 35.0 mg, 0.275 mmol, 1.20 eq.) was added to a solution of the intermediate 32 (175 mg, 0.229 mmol, 1.00 eq.), Glu-CAM(Bn) (142 mg, 0.275 mmol, 1.00 eq.) and O-(Benzotriazol-1-yl)-N,N,N',N'-tetramethyluronium tetrafluoroborate (TBTU, 88.0 mg, 0.275 mmol, 1.20 eq.) in DCM (50 mL). The reaction mixture was stirred at room temperature for 48 hours. The solvent was removed under reduced pressure and the residue dissolved in dichloromethane (100 mL) and washed with mQ water (3×100 mL). The organic phase was dried with sodium sulfate, the solvent removed under reduced pressure and the residue purified by flash chromatography over silica using a gradient of 1-5% methanol in dichloromethane. The solvent were removed under reduced pressure yielding the protected ligand 33 as a white foamy solid (162 mg, 56.0% over the last two steps).

$^1$H NMR (400 MHz, CDCl$_3$) (δ, ppm)=8.51; (d, 1H, J=8), 8.00; (m, 2H), 7.66; (m, 3H), 7.48-7.08; (m, 36H), 5.23-5.02; (m, 13H), 3.43-3.18; (m, 8H), 2.24-1.56; (m, 8H), 1.41; (s, 9H).

$^{13}$C NMR(400 MHz, CDCl$_3$) (δ, ppm)=172.0, 171.7, 169.16, 165.5, 165.0, 151.8, 151.7, 151.6, 146.9, 146.8, 146.7, 136.5, 136.4, 136.2, 129.1, 128.8, 128.7, 128.6, 128.5, 128.4, 128.3, 128.2,1 128.1, 128.0, 127.9, 127.8, 127.6, 127.5, 127.3, 127.1, 124.3, 124.2, 124.1, 123.2, 123.1, 123.0, 80.5, 76.2, 76.0, 75.8, 71.4, 71.2, 70.7, 48.7, 46.1, 45.3, 43.4, 41.9, 31.1, 29.0, 28.2, 27.57, 27.34.

ESI-MS m/z=[M+Na]$^+$1287.7 m/z (Calcd. 1287.5)

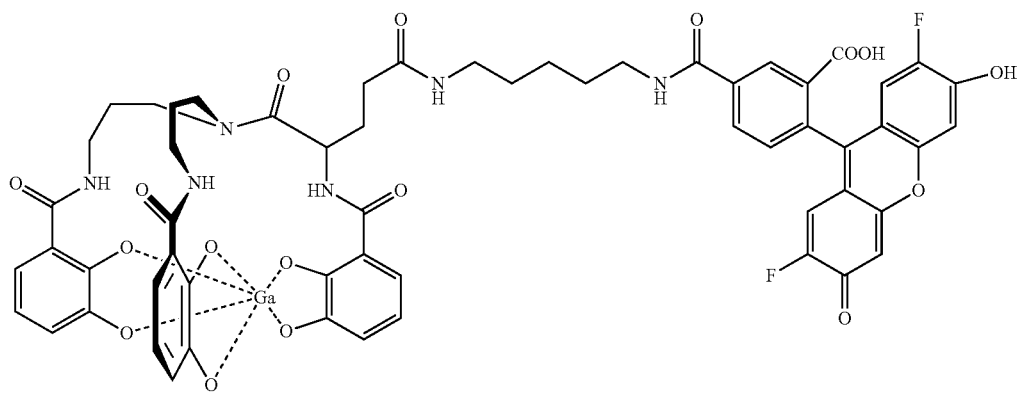

Figure 13:
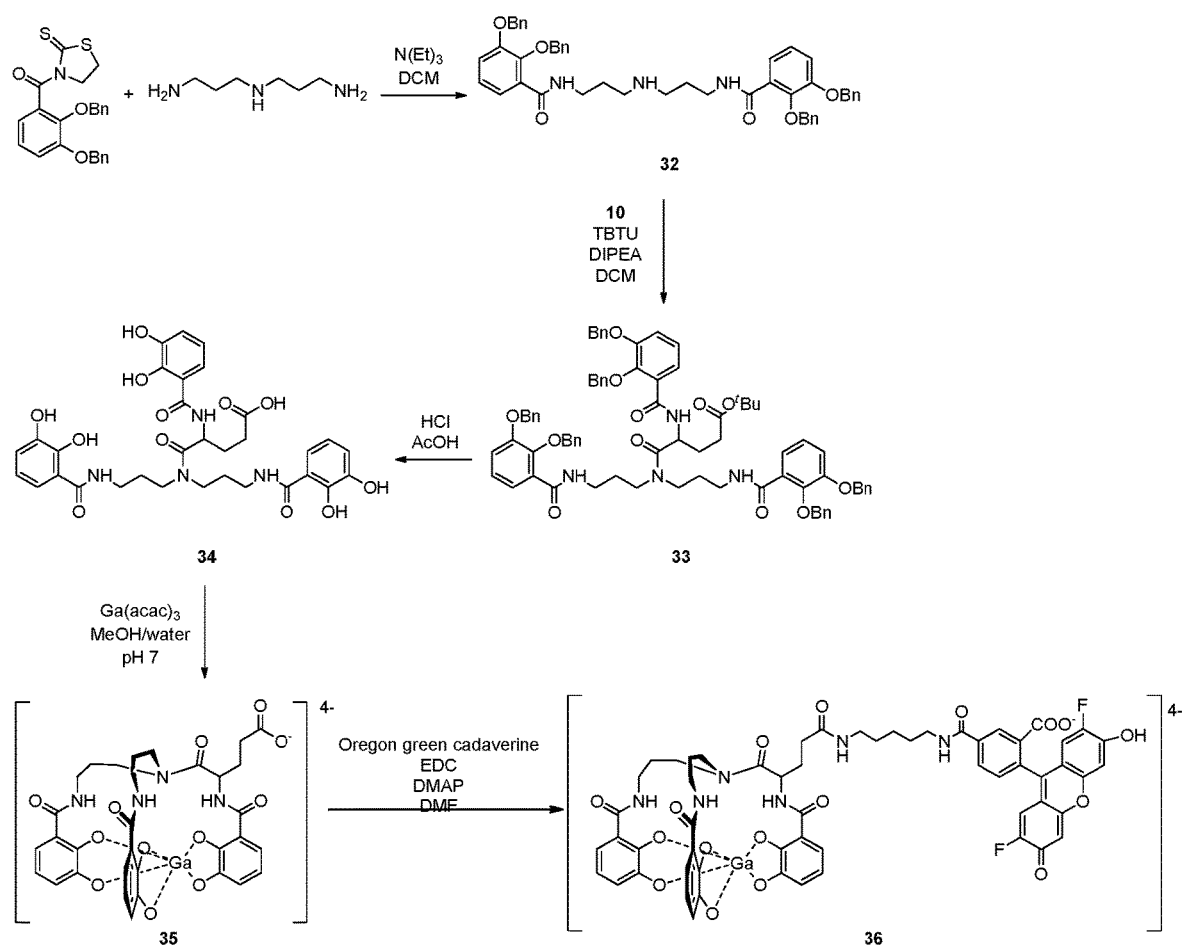
FIG. 13 is a schematic illustration of an exemplary embodiment of a synthesis of Ga-3,3-LiCAM-GluCAM-OG (36).

The synthesis of Ga-3,3-LiCAM-GluCAM-OG (36) is illustrated in FIG. 13.

32: 3,3-Li-bis-CAM(Bn)

CAM(Bn2)-thiaz was synthesized as previously reported (Allred et al., *ACS Chem Biol* 2013, 8 (9), 1882-1887). A solution of dipropylenetriamine (DPTA, 28.0 mg, 0.219 mmol, 1.00 eq) and triethylamine (5 drops) in dichloromethane (5 mL) was added to a solution of CAM(Bn2)-thiaz (200 mg, 0.450 mmol, 2.10 eq). The reaction mixture was stirred at room temperature for 26 hours. The solvent was removed under reduced pressure and the residue dissolved in dichlo- 34: Symmetric-3,3-Li-Glu-CAM The protected ligand symmetric-3,3-Li-Glu-CAM(Bn) (33, 90.0 mg, 71.0 µmol) was dissolved in 6 M HCl (aq) (1 mL) and acetic acid (1 mL). The reaction mixture was stirred for 18 h at room temperature after which the solvent was removed under reduced pressure. The residue was dissolved in CH$_3$OH/water and lyophilized to yield the deprotected ligand 34 as a white solid (4.70 mg, 9.88%).

$^1$H NMR (400 MHz, CDCl$_3$) (δ, ppm)=7.74-7.34; (m, 3H), 6.95; (m, 3H), 6.73; (m, 3H), 4.72; (m, 1H), 4.32; (t, 1H, J=8), 3.96; (t, 1H, J=8), 3.78-3.458; (m, 4H), 3.26-3.11; (m, 4H), 2.49; (m, 2H), 2.63; (m, 1H), 2.16; (m, 1H), 2.04; (m, 2H).

$^{13}$C NMR (400 MHz, MeOD) (δ, ppm)=173.6, 173.5, 170.7, 169.9, 148, 9, 148.6, 146.0, 145.9, 118.5, 118.2, 117.9, 117.5, 117.2, 115.8, 115.2, 51.8, 51.5, 50.8, 45.3, 35.7, 29.7, 26.3, 26.1.

35: Ga-Symmetric-3,3-Li-Glu-CAM

The deprotected ligand symmetric-3,3-Li-Glu-CAM (34, 4.7 mg, 7.3 μmol, 1.0 eq) was dissolved in CH$_3$OH (2 mL). Ga(acac)$_3$ (2.7 mg, 7.3 μmol, 1.0 eq) was added to the reaction mixture. A solution of 0.5 M KOH (aq) (0.1 mL) was added to the reaction mixture to adjust the pH to 7. The reaction mixture was stirred at room temperature for 2 hours. The reaction mixture was concentrated under reduced pressure. Addition of diethylether to the reaction mixture resulted in the formation of a precipitate that was isolated by centrifugation. The slightly pink solid was re-suspended in diethtylether and centrifuged and dried in vacuo (3.7 mg, 62.7%).

Figure 14:
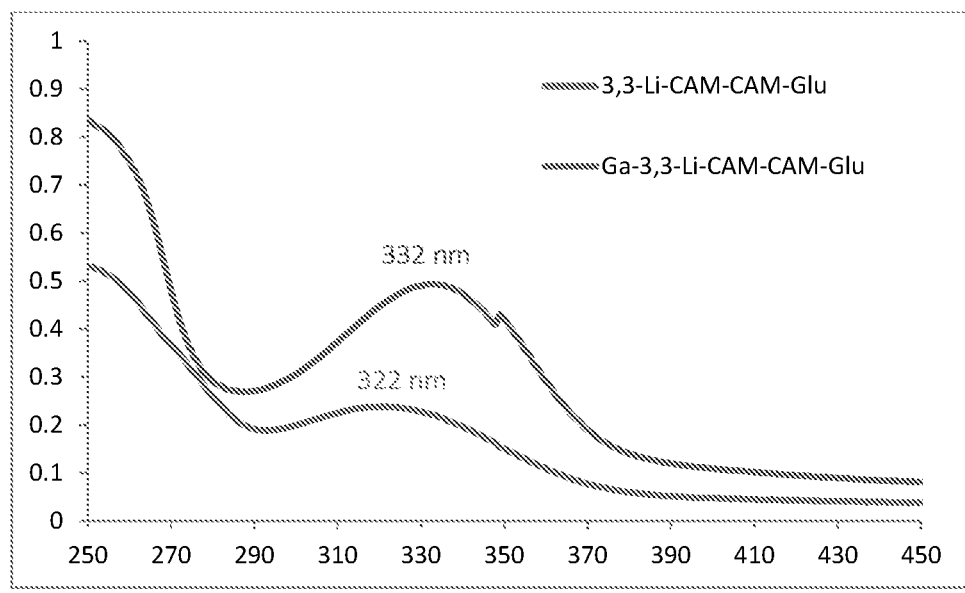
FIG. 14 is an illustration of a UV-visible absorbance spectra of symmetric-3,3-Li-Glu-CAM (34) ($\lambda_{max}$ 322) and Ga-3,3-LiCAM-GluCAM-OG (35) ($\lambda_{max}$332) in Tris buffer, pH 7.4.

UV-visible absorbance spectra of symmetric-3,3-Li-Glu-CAM (34) ($\lambda_{max}$ 322) and Ga-3,3-LiCAM-GluCAM-OG (35) ($\lambda_{max}$ 332) in Tris buffer, pH 7.4 are illustrated in FIG. 14.

36: Ga-3,3-LiCAM-GluCAM-OG

Ga-symmetric-3,3-Li-Glu-CAM (35, 1.47 mg, 1.36 μmol, 1.00 eq), and OREGON GREEN CADAVERINE dye (1.00 mg, 2.01 μmol, 1.00 eq) were dissolved in DMF (2 mL). Dimethylaminopyridine (DMAP, one crystal) and 1-ethyl-3-(3-dimethylaminopropyl)carbodiimide (EDC, 0.462 mg, 2.41 μmol, 1.20 eq.) were added to the reaction mixture that was further stirred at room temperature for 15 hours. The solvent was removed under reduced pressure and the red residue purified by HPLC using method 4.

Figure 15:
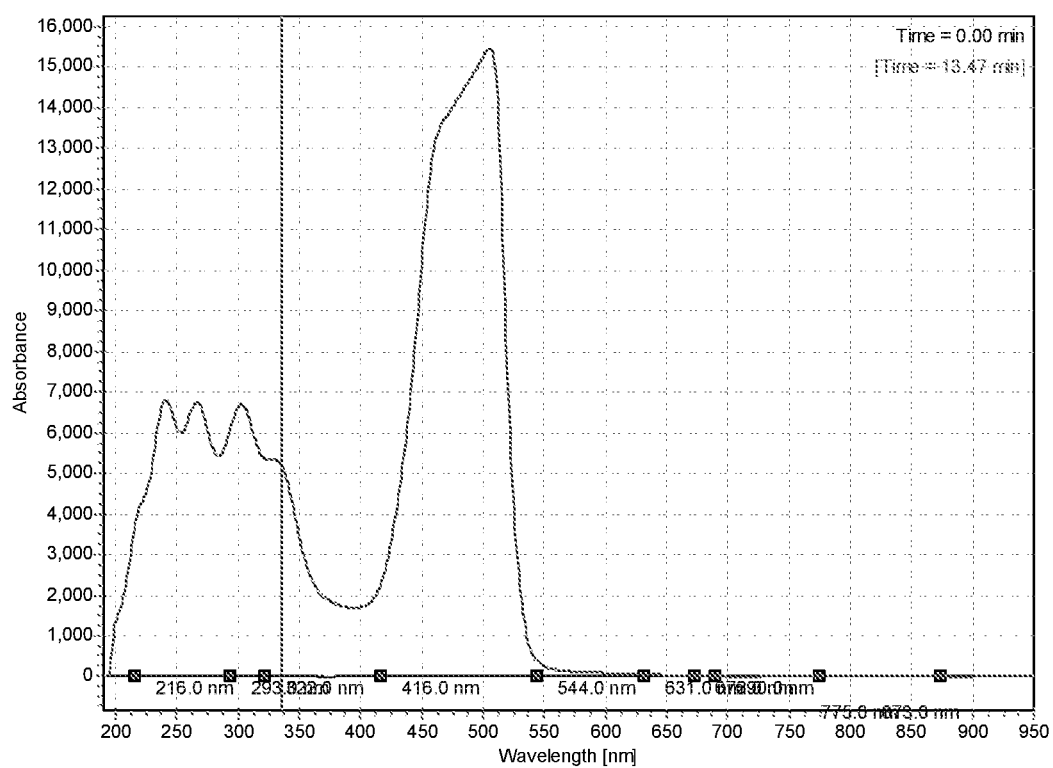
FIG. 15 is an illustration of a UV-visible absorbance spectra of Ga-3,3-LiCAM-GluCAM-OG (36).

A UV-visible absorbance spectra of Ga-3,3-LiCAM-Glu-CAM-OG (36) in illustrated in FIG. 15.

Example 5: Ga-2,2-LiCAM-GluCAM-OG

38: 2,2-Li-[CAM(Bn)]$_2$-[Glu-CAM(Bn)]

2,2-Li-CAM(Bn) (37, 241 mg, 0.330 mmol), Glu-CAM (Bn) (17, 235 mg, 0.452 mmol) and TBTU (154 mg, 0.480 mmol) were disolved in 5 mL of dichloromethane. DIPEA (98 mg, 0.76 mmol) was added to the crude. The yellowish solution obtained was magnetically stirred under N$_2$ atmosphere for 96 hours. The crude was diluted in 30 mL of DCM and then washed with NaHCO$_3$ 4.6% three times. The organic phase was collected, dried over Na$_2$SO$_4$ and the solvent evaporated under reduced pressure. The yellowish oil obtained was purified using the combiflash system using a gradient of MeOH in DCM. 46.4 mg recovered (yield: 7%)

$^1$H-NMR (400 MHz, CDCl$_3$) δ 1.41; (d, 9H), 1.66; (m, 1H), 1.95; (m, 1H), 2.24; (m, 2H), 3.25-3.70; (m, 8H), 5.04-5-24; (m, 13H) 7.06-7.74; (m, 39H), 8.05-8-16; (m, 2H8.58-8.68; (m, 1H).

$^{13}$C-NMR (100 MHz, CDCl$_3$) δ 17.47, 28.11, 29.78, 31.15, 37.74, 38.46, 45.83, 46.96, 48.92, 71.32, 80.42, 116.93, 117.14, 123.14, 123.40, 124.28, 127.02, 127.65, 127.94, 128.41, 128.70, 128.95, 129.27, 136.55, 146.78, 147.05, 151.79, 164.90, 165.69, 165.96, 171.98, 172.48.

39: 2,2-Li-[CAM]$_2$-[Glu-CAM]

2,2-Li-[CAM(Bn)]2-[Glu-CAM(Bn)] (42.7 mg, 34.5 μmol) was dissolved in 1 mL of HCl 37% and 1 mL of glacial acetic acid and magnetically stirred at room temperature under N$_2$ gas for 17 hours. The solvent was evaporated and then fresh HCl 37% and glacial AcOH were added. The reaction was allowed to run for 24 hours under the same conditions described above. Next, the solvent was evaporated and the solid obtained was dissolved in MeOH and then shook off for 5 days under H$_2$ gas in presence of Pd/C catalyst (Degussa Type). The crude obtained was filtrated through Celite 545 powder. The volume of the crude obtained was condensed to 0.4 mL and then 1 mL of ether was added. The suspension observed was centrifuged, the supernatant was removed and the solid recovered (process carried out three times). Next, the purple solid obtained was dissolved in 10 mL of a mixture (50/50) of MeOH and HCl

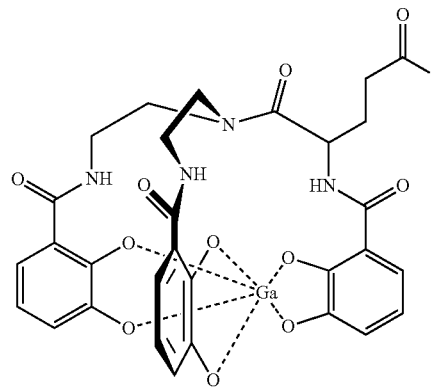
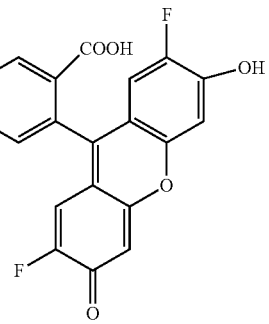

Figure 16:
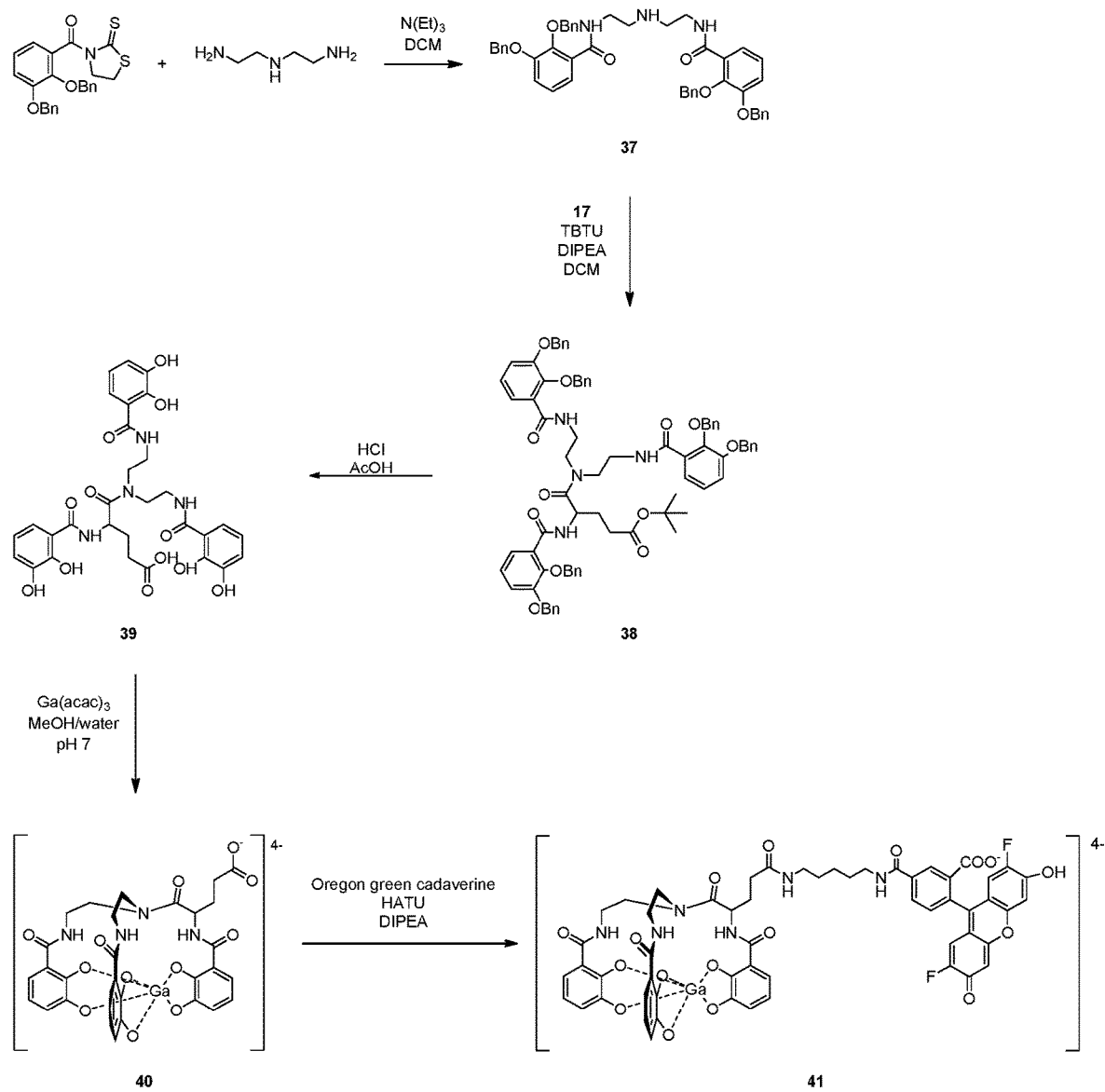
FIG. 16 is a schematic illustration of an exemplary embodiment of a synthesis of Ga-2,2-LiCAM-GluCAM-OG.

The synthesis of Ga-2,2-LiCAM-GluCAM-OG is illustrated in FIG. 16. The protected synthetic siderophore 38 was obtained after condensation of Glu-CAM 17 and 2,2-Li-CAM 37 (Joshua et al., Tetrahedron Letters 1984, 25 (50), 5725-5728). The cathecholate was deprotected in acid conditions to allow the formation of the gallium complex 40. The final linear ento-light 41 was obtained after conjugation of 40 and OREGON GREEN CADAVERINE dye.

0.1 M, and then washed three times with hexanes. The aqueous phase was recovered and the solvent evaporated to yield 8.3 mg (yield: 36%) of a yellowish/brownish compound $^1$H-NMR (400 MHz, MeOD) δ 2.13; (m, 1H), 2.32; (m, 1H), 2.49; (m, 2H), 3.49-3.89; (m, 9H), 4.70; (dd, 1H), 6.46-7.32; (m, 9H).

40: Ga-2,2-Li-[CAM]$_2$-[Glu-CAM]

2,2-Li-CAM-Glu-CAM (4.6 mg, 7.1 μmol) was dissolved in MeOH and mixed with 43 μL of methanolic KOH 0.5M (22 μmol). Next, Ga(acac)$_3$ (2.6 mg, 7.0 μmol) was added and the crude obtained was rotated at room temperature for 15 hours. After this time, the volume of the crude was reduced to 1/10 of its original volume. Then, 1 mL of ether was added, the solution obtained was shaken and the suspension obtained was centrifuged for 5 minutes at 12000 rpm. The supernatant was removed and the brownish solid was collected. This process was carried out three times and at the end 6 mg of a brownish solid were recovered (yield: 102%).

Figure 17:
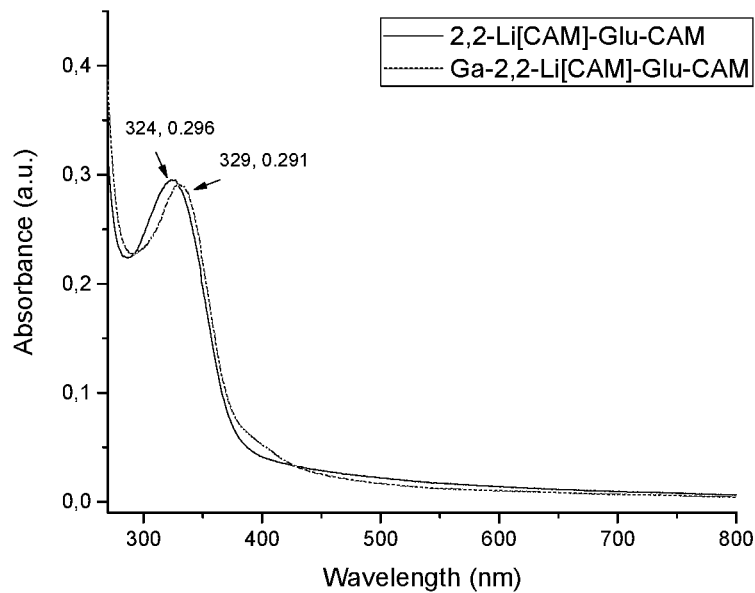
FIG. 17 is an illustration of a UV-visible spectra of 2,2-Li-[CAM]-[Glu-CAM] ($\lambda_{max}$ 324) and Ga-2,2-Li-[CAM]-[Glu-CAM] ($\lambda_{max}$ 329) in TRIS buffer pH 7.45 and DMF 2% (v/v).

UV-visible spectra of 2,2-Li-[CAM]-[Glu-CAM] ($\lambda_{max}$ 324) and Ga-2,2-Li-[CAM]-[Glu-CAM] ($\lambda_{max}$ 329) in TRIS buffer pH 7.45 and DMF 2% (v/v) are illustrated in FIG. 17.

41 Ga-2,2-LiCAM-GluCAM-OG

Ga-2,2-Li-CAM-Glu-CAM (1.9 mg, 2.3 μmol), OREGON GREEN 488 CADAVERINE dye (1.1 mg, 2.2 μmol), ED.HCl (0.7 mg, 4 μmol) and DMAP (catalytic amount) were dissolved in 1 mL of anhydrous DMF. The solution obtained was rotated at room temperature for 65 hours. After this time, the DMF was evaporated and the solid obtained re-suspended in a mixture of ACN 20% and DMF 7% in water. Next, the sample was applied to a C-18 reversed phase silica column and eluted with 100 mL of ACN 20%-DMF 7% in water, 50 mL of ACN 50%-DMF 7% in water, 50 mL of ACN 60%-DMF 5% in water and 50 mL of ACN 80%-DMF 7% in water. Yield: 2.3%.

Figure 18:
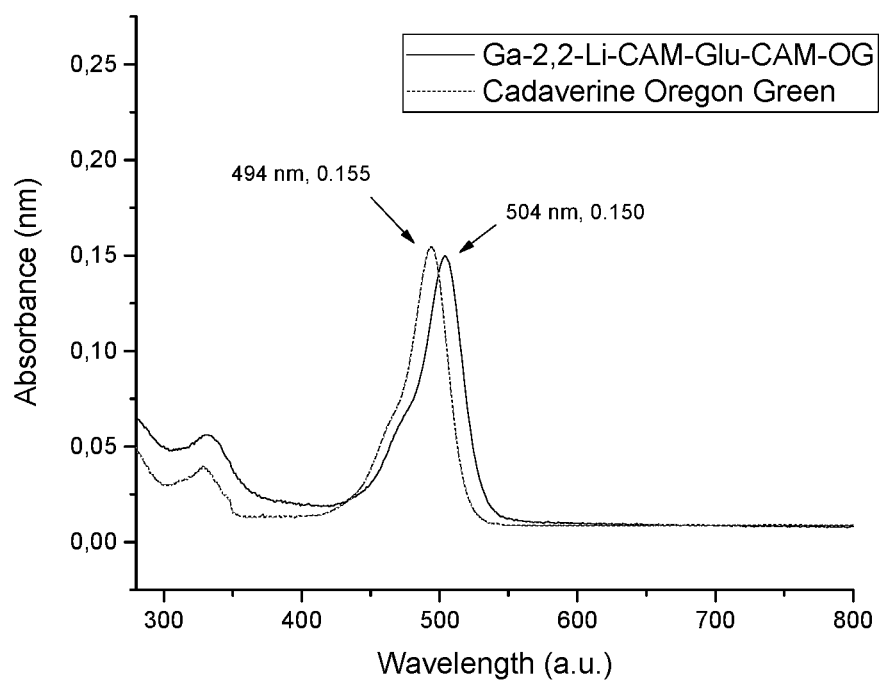
FIG. 18 is an illustration of a UV-visible spectra of Ga-2,2-LiCAM-GluCAM-OG ($\lambda_{max}$ 504) and OREGON GREEN 488 dye ($\lambda_{max}$ 494) in TRIS buffer, pH 9.06.

UV-visible spectra of Ga-2,2-LiCAM-GluCAM-OG ($\lambda_{max}$ 504) and OREGON GREEN 488 dye ($\lambda_{max}$ 494) in TRIS buffer, pH 9.06 are illustrated in FIG. 18.

Example 6: Ga-3,3-LiCAM-GluCAM-Light-Switch

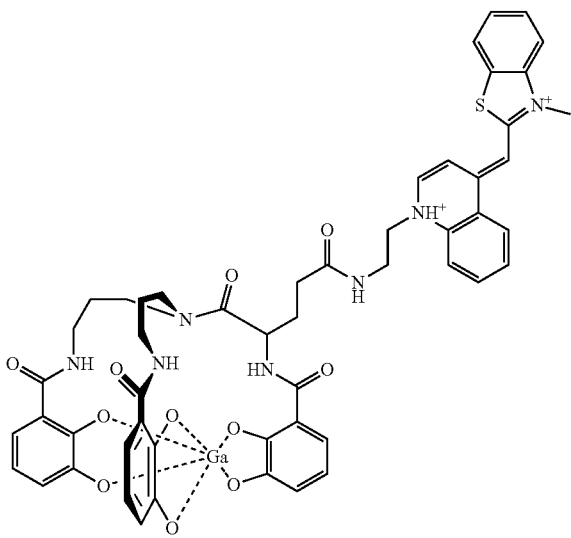

Figure 19:
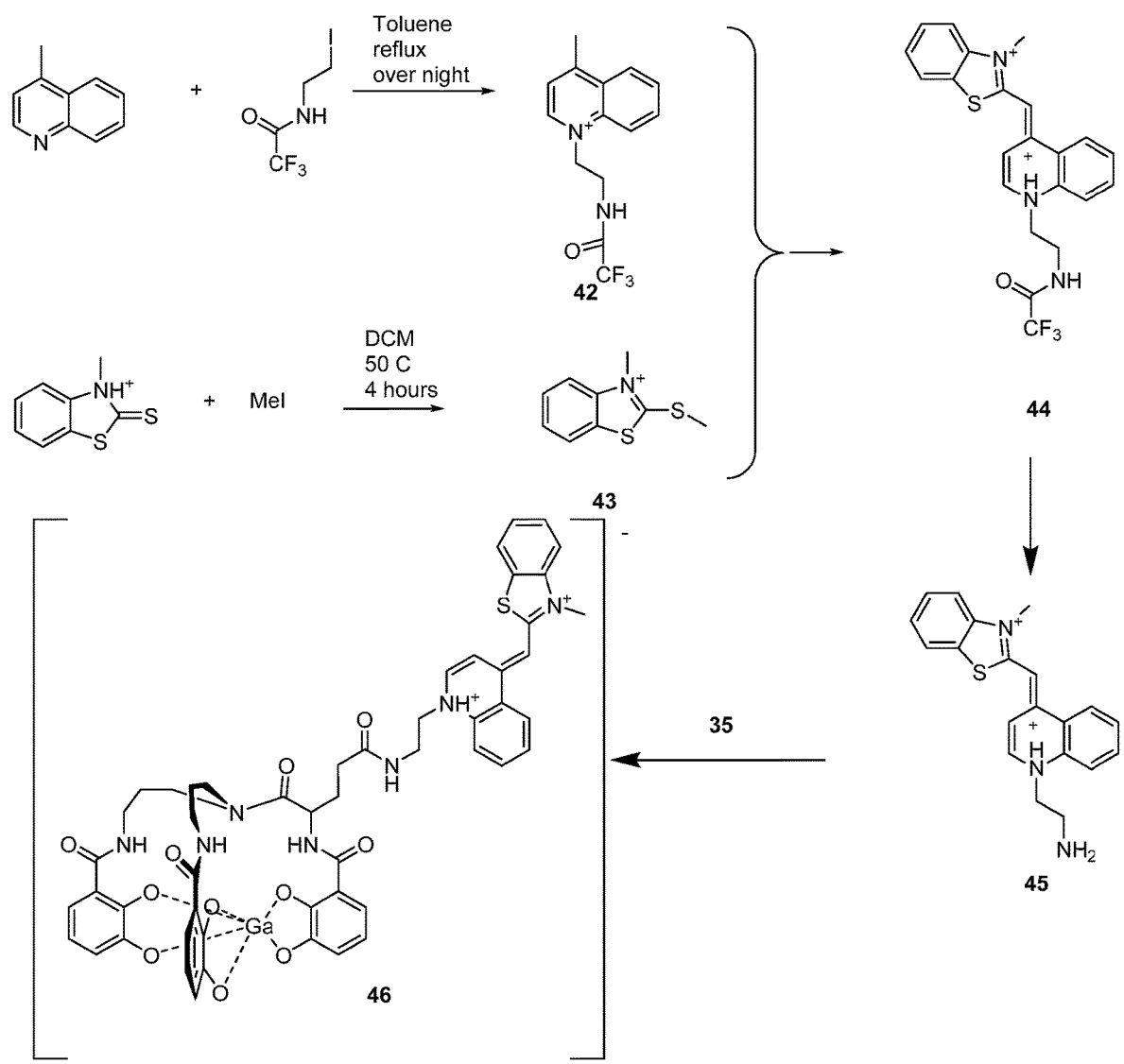
FIG. 19 is a schematic illustration of an exemplary embodiment of a synthesis of Ga-3,3-LiCAM-GluCAM-light-switch.

The synthesis of Ga-3,3-LiCAM-GluCAM-light-switch is illustrated in FIG. 19.

42: Lepidine (0.100 g, 0.698 mmol, 1.00 eq) and N-(b-iodoethyl)trifluoror acetamide (0.540 g, 2.00 mmol, 2.90 eq) were diluted in dry toluene (1 ml) and refluxed overnight under N$_2$. All compounds were soluble and without color. After 2 hours the mixture turned orange and heterogeneous. The reaction mixture was refluxed overnight. The yellow precipitate was rinsed with toluene (2×5 mL) then ether (5 mL). The yield obtained was over 100 percent (0.290 mg). Toluene was observed in $^1$H NMR.

$^1$H NMR 400 MHz, (MeOD δ ppm): 9.20; (1H, d, 6.0 Hz), 8.63; (2H, m), 8.32; (1H, m), 8.11; (1H, m), 8.01; (1H, d, 5.6 Hz), 5.24; (2H, t, 4.8 Hz), 4.39; (2H, t, 4.8 Hz), 3.11; (3H, s).

43: 3-methylbenzothiazole-2-thione (0.107 g, 0.590 mmol, 1.00 eq.) was diluted in MeI (0.100 g, 0.704 mmol, 1.20 eq) and DCM (1 mL). The reaction mixture was stirred at 50° C. for 4 hours. The precipitate was filtered and washed with acetone (52.0 mg, 48.1%).

$^1$H NMR 400 MHz, (MeOD δ ppm): 8.27; (1H, d, 8.0 Hz), 8.12; (1H, d, 8.3 Hz), 7.88; (1H, t, 8.8 Hz), 7.75; (1H, t, 7.6 Hz), 4.19; (3H, s).

44: 42 (86.0 mg, 0.303 mmol, 1.00 eq) and 43 (60 mg, 0.303 mmol, 1.00 eq) was diluted under N$_2$ in anhydrous ethanol (2 ml). The solution turned yellow and was heterogeneous. The reaction mixture was stirred at 65° C. for 5 minutes to allow full solubilization of both solids. Trimethyl amine (61.4 mg, 0.607 mmol, 2.00 eq) was added and the solution turned blood red immediately. The reaction was left to return to room temperature then ether (5 mL) was added to the solution to precipitate the red solid. The dye was filtered out, and then recrystallized with acetone and ether leading to 76 mg (58.4%).

$^1$H NMR 400 MHz (MeOD δ ppm): 8.70; (1H, d, 8.0 Hz), 8.29; (1H, d, 7.2 Hz), 8.15; (1H, d, 8.8 Hz), 8.00, (1H, t, 7.2 Hz), 7.94; (1H, d, 8.0 Hz), 7.79; (1H, t, 8.0 Hz), 7.72; (1H, d, 8.0 Hz), 7.65; (1H, t, 7.6 Hz), 7.48; (2H, m), 6.99; (1H, s), 4.77; (2H, t, 6.0 Hz), 4.06; (3H, s), 3.86; (2H, t, 6.0 Hz).

45: Protected turn on dye (30 mg) was diluted in 0.6 ml of concentrated HCl and heated for 1 hour at 65° C. KOH was added until a red precipitate formed. The red solid was filtered and washed with ether. Proton NMR was busy and $^{19}$F still showed a signal. The reaction was run again using the same conditions of equivalency but this time for longer and for 3 hours. After the same work up $^{19}$F NMR showed no signal and the $^1$H NMR was less busy even though not an ideal spectrum.

46: Ga-3,3-LiCAM-GluCAM-light-switch. Ga-3,3-Li-CAM-Glu-CAM (35, 17.5 mg, 0.025 mmol, 1.00 eq), dye (45, 8.28 mg, 0.024 mmol, 1.00 eq) and EDC (5.66 mg, 0.029 mmol, 1.20 eq.) were solubilized in DMF (1.5 mL). A catalytic amount of DMAP was added. The reaction was stirred overnight. The product was obtained after removal of the solvents under reduced pressure.

Example 7: Fe-3,3-LiCAM-GluCAM-Tb

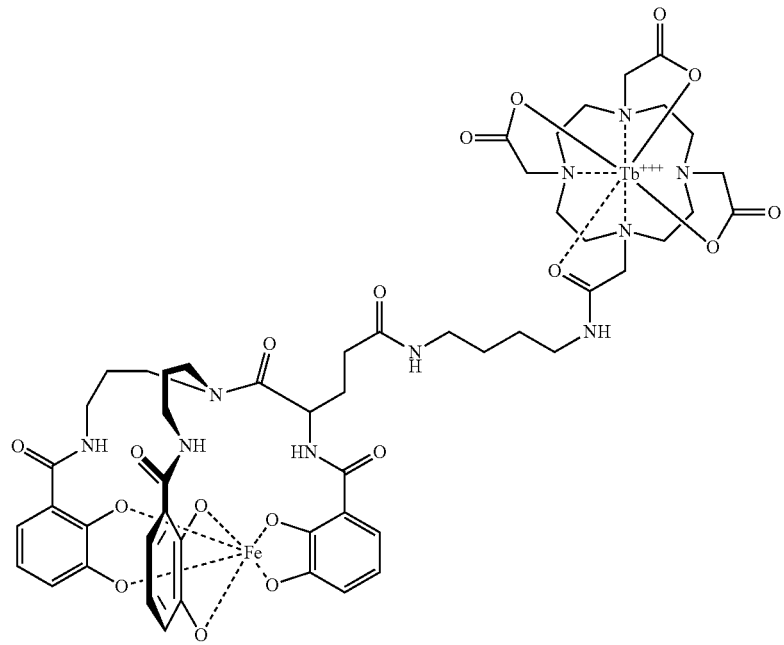

Figure 20:
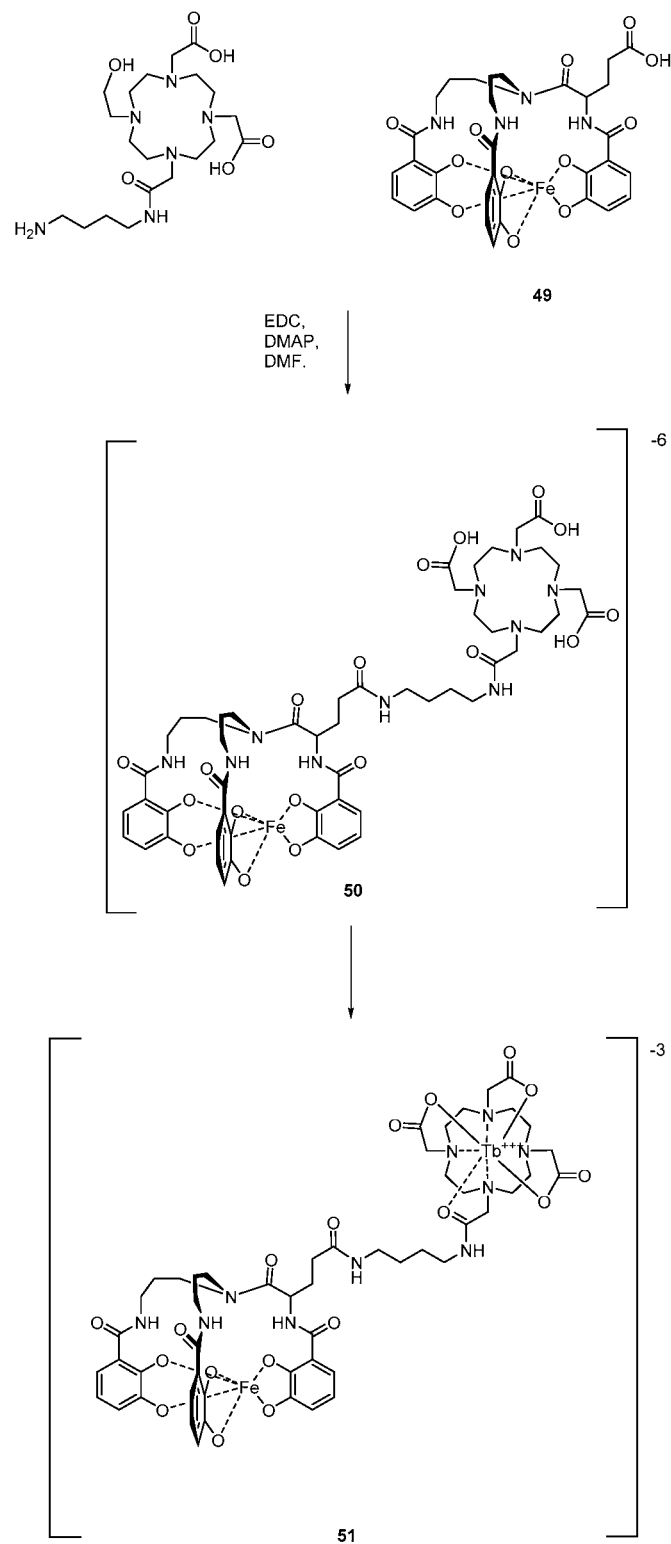
FIG. 20 is a schematic illustration of an exemplary embodiment of a synthesis of Fe-3,3-LiCAM-GluCAM-Tb.

The synthesis of Fe-3,3-LiCAM-GluCAM-Tb is illustrated in FIG. 20.

50: Fe-3,3-Li-CAM-Glu-CAM-DO3A

Fe-3,3-Li-CAM-Glu-Cam (0.9 mg, 0.00125 mmol, 1 eq) was diluted in DMF (0.2 mL) and EDC (0.286 mg, 0.0015 mmol, 1.2 eq). Aminobutyl-DOTA, 4HCl, HPF$_4$ (Macrocyclic, 0.96 mg, 0.0125 mmol, 1 eq) was diluted in DIPEA (0.8 mg, 0.00625 mmol, 5 eq) and DMF (0.2 mL) and added to the red iron complex solution. The reaction mixture turns purple and was stirred for 2 hours. Solvent were removed and water was added to the residue which was purified by HPLC.

51: Fe-3,3-LiCAM-GluCAM-Tb

Fe-3,3-Li-CAM-Glu-CAM-Do3A was solubilized in methanol and terbium was added. Then a drop of pyridine was added. The reaction mixture was stirred at reflux for 3 days, with regular addition of NaOH (aq) to maintain the pH around 8. Removal of the solvents under reduced pressure yielded the Tb probe 51.

Example 8: AuNP @ Fe-3,3-LiCAM-GluCAM

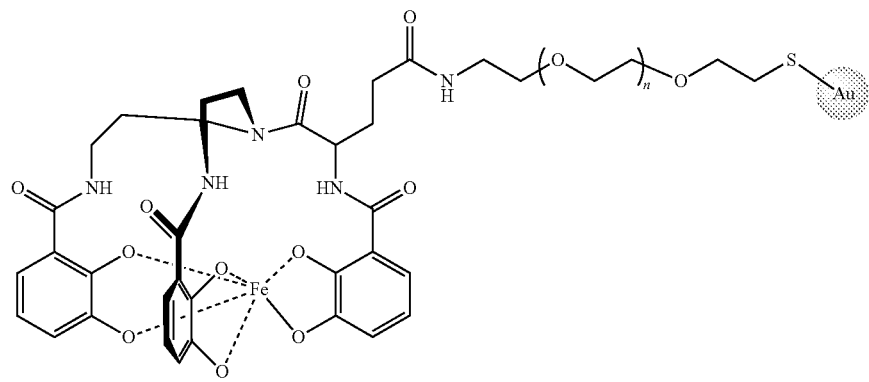

Figure 21:
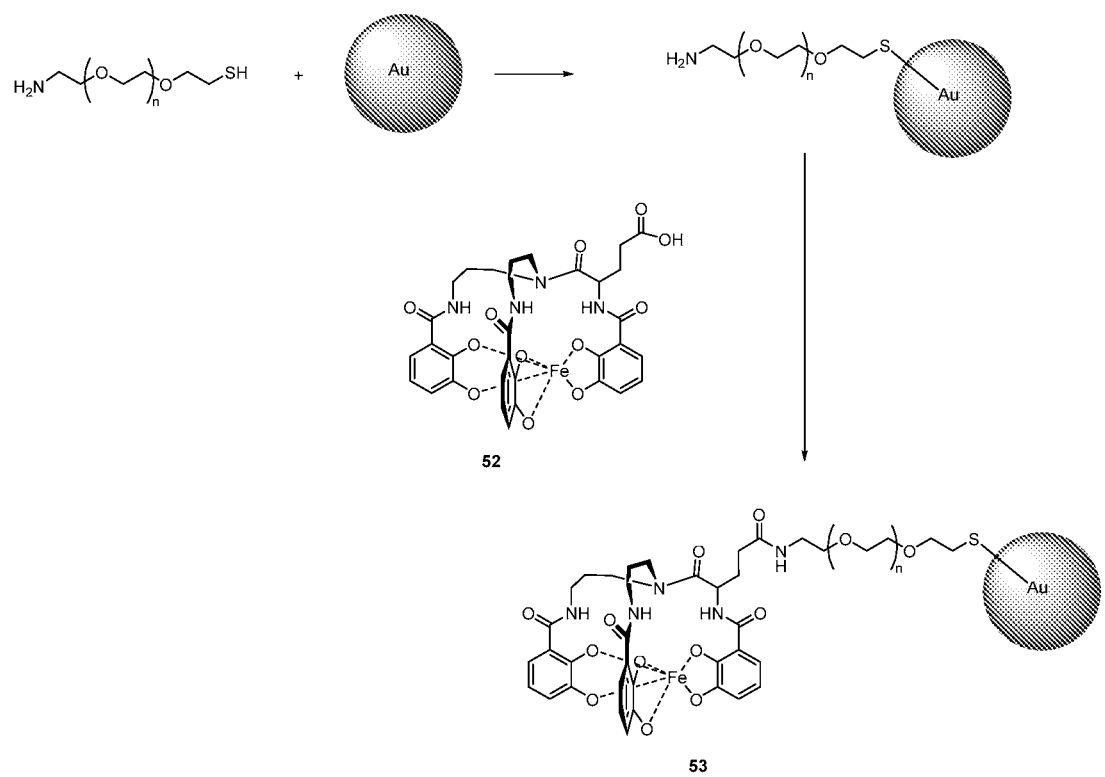
FIG. 21 is a schematic illustration of an exemplary embodiment of a synthesis of AuNP @ Fe-3,3-LiCAM-GluCAM.

The synthesis of AuNP@Fe-3,3-LiCAM-GluCAM is illustrated in FIG. 21.

52: Fe-3,3-Li-CAM-Glu-CAM

A drop of methanolic KOH (0.5M) was added to a solution of 3,3-Li CAM 4 (3.30 mg, 4.90 mmol, 1 eq) and Fe(acac)$_3$ (1.74 mg, 4.90 mmol, 1 eq.) in methanol (0.5 mL). After 3 hours the complex was precipitated by addition of ether. A red solid was recovered after centrifugation. The red solid was washed twice with ether.

Figure 22:
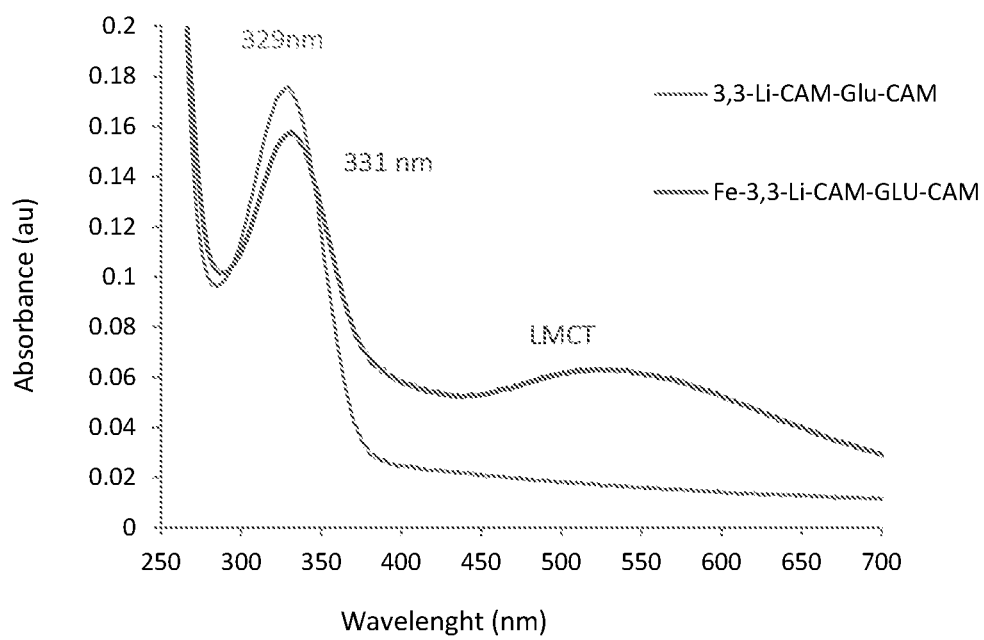
FIG. 22 is an illustration of a UV-visible spectra of 3,3-Li-CAM-GLu CAM ($\lambda_{max}$ 329) and Fe-3,3-Li-CAM-GluCAM ($\lambda_{max}$ 331) in Tris buffer, pH 7.

UV-visible spectra of 3,3-Li-CAM-GLu CAM ($\lambda_{max}$ 329) and Fe-3,3-Li-CAM-GluCAM ($\lambda_{max}$ 331) in Tris buffer, pH 7 are illustrated in FIG. 22.

Synthesis of Citrate Capped AuNP

A 1.00 w/w % solution of sodium citrate (stock 1) was made by dissolving 1.14 g of Na$_3$-citrate dehydrate into 99.9 g of deionized water available under the trade designation MILLI-Q water from Millipore Corporation. A 0.01 w/w % solution of gold chloride (stock 2) was made by dissolving 0.100 g of a 30 w/w % HAuCl$_4$ into 300 g of MILLI-Q water. AuNP were made by boiling and stirring 50 mL of stock 2 and pipetting in 1 mL of stock 2. This solution was kept at a boil for 10 minutes to ensure the reaction went to completion. DLS indicates that the average diameter of these particles is 16.0 nm with an average zeta potential of −55.5 mV.

Figure 23:
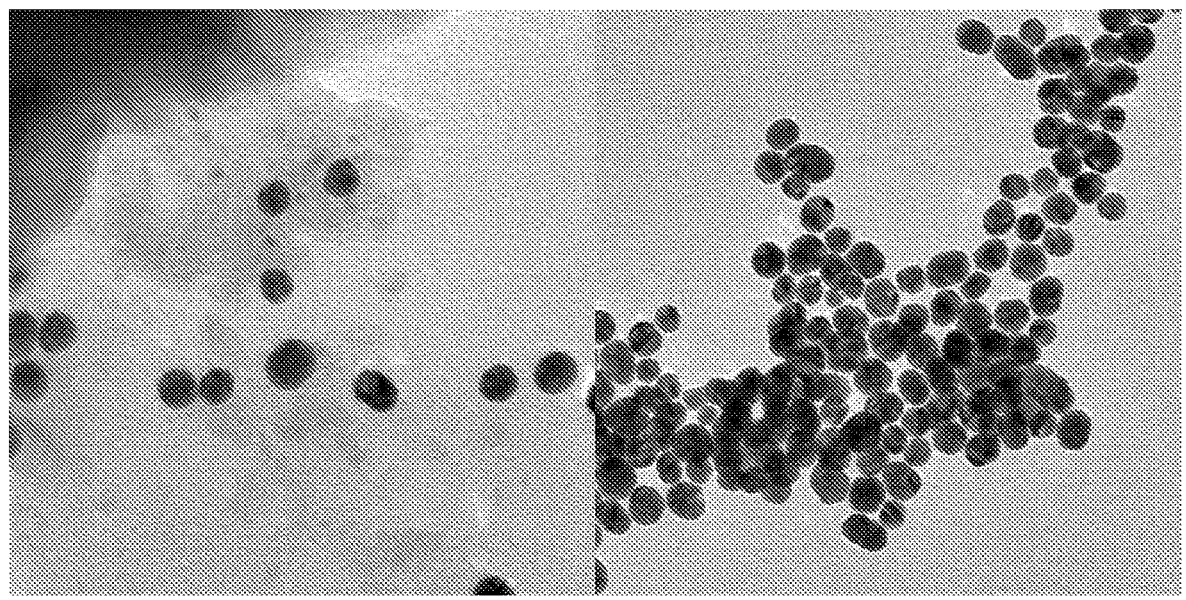
FIG. 23 is an illustration of a transmission electron micrograph (TEM) of Citrate-caped AuNP frame.

TEM of Citrate-caped AuNP frame are illustrated in FIG. 23.

AuN @ PEG: 25 mL of the 21/24 nm AuNP solution was mixed with NH$_3$Cl-PEG-SH (2000 mw, 5.0 mg, 2.5 µmol) for 2 hours. The crude reaction mixture was then filtered on 10 kDa centrifugal filters and washed with MILLI-Q water three times. The remaining AuNPs were then re-suspended in MILLI-Q water.

Figure 24:
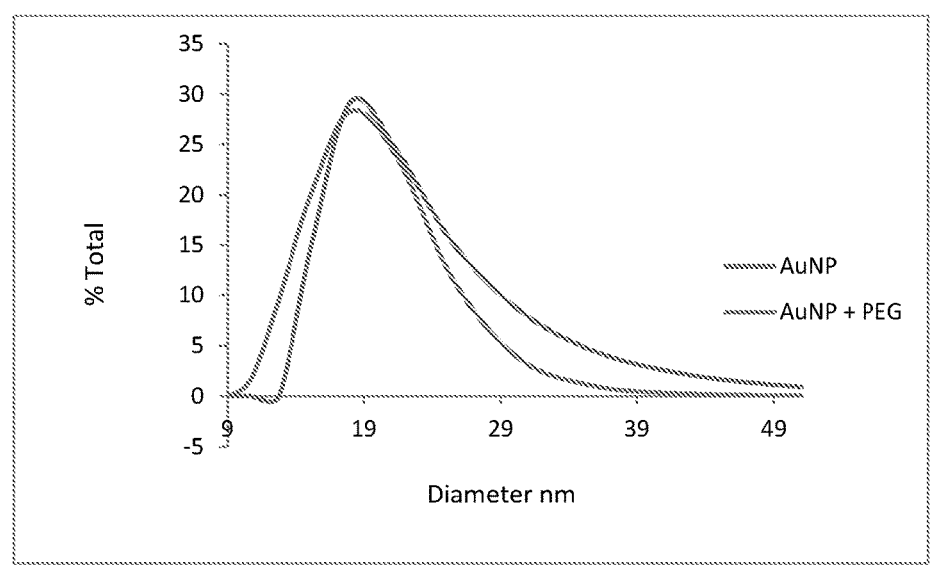
FIG. 24 is an illustration of the size distribution of Au NP and AuNP @ PEG.

Size distribution of Au NP and Au NP @ PEG obtained from dynamic light scattering are illustrated in FIG. 24.

AuNP @ Fe-3,3-LiCAM-GluCAM: 53

The PEGylated AuNPs(b) were mixed with Fe$^{III}$-5-(Bis(3-(2,3-dihydroxybenzamido)propyl)amino)-4-(2,3-dihydroxybenzamido)-5-oxopentanoic acid (1 mg, 1.31 µmol) dissolved in DMF (0.25 mL), DMAP (0.03 mg, 0.25 µmol), TBTU (1 mg, 3 µmol), and DIPEA (0.3 mg, 3 µmol). This reaction as allowed to run overnight, the solution was centrifuged through 10 kDa filters and washed with MILLI-Q water three times. The resulting solution was re-suspended in MILLI-Q water for analysis by TEM and DLS.

Figure 25:
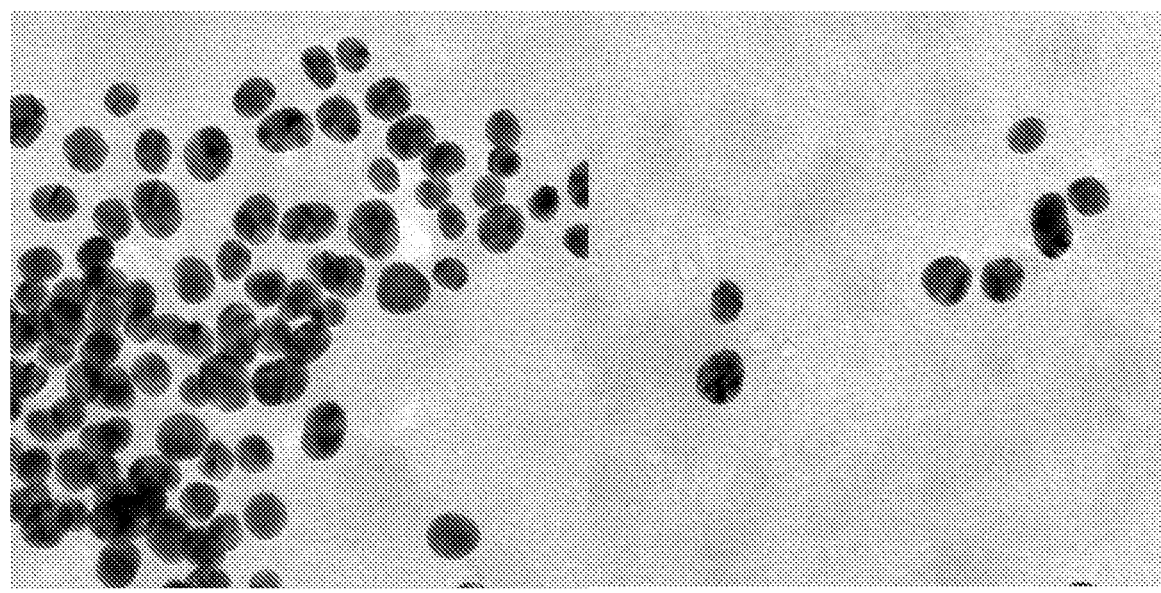
FIG. 25 is an illustration of a transmission electron micrograph (TEM) of AuNP @ Fe-3,3-LiCAM-GluCAM.

A TEM of AuNP @ Fe-3,3-LiCAM-GluCAM is illustrated in FIG. 25.

Figure 26:
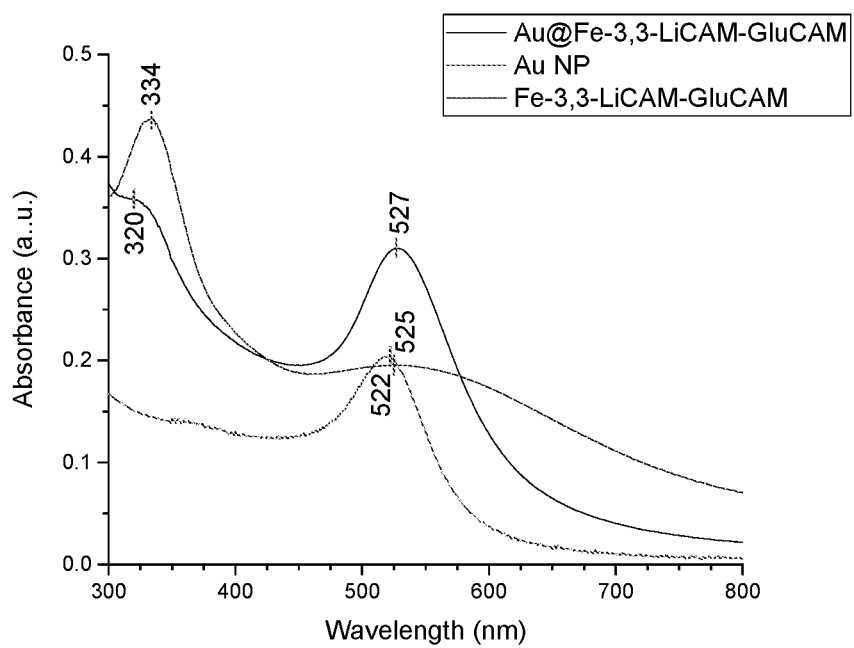
FIG. 26 is an illustration of a UV-visible spectra of AuNP @ Fe-3,3-LiCAM-GluCAM ($\lambda_{mac}$ 320, 527), Fe-3,3-LiCAM-GluCAM ($\lambda_{max}$ 334, 525), and the citrate capped Au nanoparticles ($\lambda_{max}$ 522).

UV-visible spectra of AuNP @ Fe-3,3-LiCAM-GluCAM ($\lambda_{max}$ 320, 527), Fe-3,3-LiCAM-GluCAM ($\lambda_{max}$ 334, 525), and the citrate capped Au nanoparticles ($\lambda_{max}$ 522) are illustrated in FIG. 26.

Preparation of T-Media

The reagents described in Table 1 were dissolved in 1 L of mQ water. The pH of the solution is fixed at 7.4 by using HCl 1N.

TABLE 1

Biological media, inorganic salts and aminoacids used for the preparation of T-media solution.

| Compound | Amount | Compound | Amount |
| --- | --- | --- | --- |
| NaCl | 6.0714 g | Leucine | 58.2 mg |
| KCl | 3.7034 g | Proline | 60.0 mg |
| CaCl$_2$ | 141.3 mg | Tryptophan | 51.0 mg |
| MgCl$_2$·6H$_2$O | 112.1 mg | Thiamine hydrochloride | 7.5 mg |
| NH$_4$Cl | 122.5 mg | Glucose | 2.0128 g |
| TRIS | 12.0313 g | Casoaminoacids | 55.1 mg |
| Na$_2$SO$_4$ | 157.2 mg | KH$_2$PO$_4$ | 32.7 mg |

The resulting solution is filtered through a 20 µm Nalgene filter.

Preparation of LB-Broth Media 5.0416 g of LB-Broth powder reagent were dissolved in 250 mL of mQ water. The resulting solution was autoclavated for 20 minutes.

Agar Plates 2.5365 g of LB Broth powder and 0.9055 g of nutrient agar were dissolved in 64 mL mQ water. The solution obtained was autoclavated for 20 minutes. The liquid recovered was poured into the agar plates. The agar plates prepared were allowed to dry and solidify at room temperature.

Sample Processing for Bacteria Detection by Fluorescence in T Media Experiments with Bacteria Genus Four Days are Needed to do a Run Day 1: Sub bacteria onto agar Day 2 pm: Sub bacteria into LB broth Day 3: Testing Day 4: Quantitative culture results Bacteria Information 1. *Klebsiella pneumoniae* ATCC 10031 (IDRL 4078)
2. *Acinetobacter baumanii* (IDRL 9919)
3. *Salmonella* species non typhi (IDRL 4247)
4. *Staphylococcus aureus* ATCC 29213 (IDRL 4307)
5. *Bacillus subtilis* ATCC 6633 (IDRL 3766)

Procedure

Figure 27:
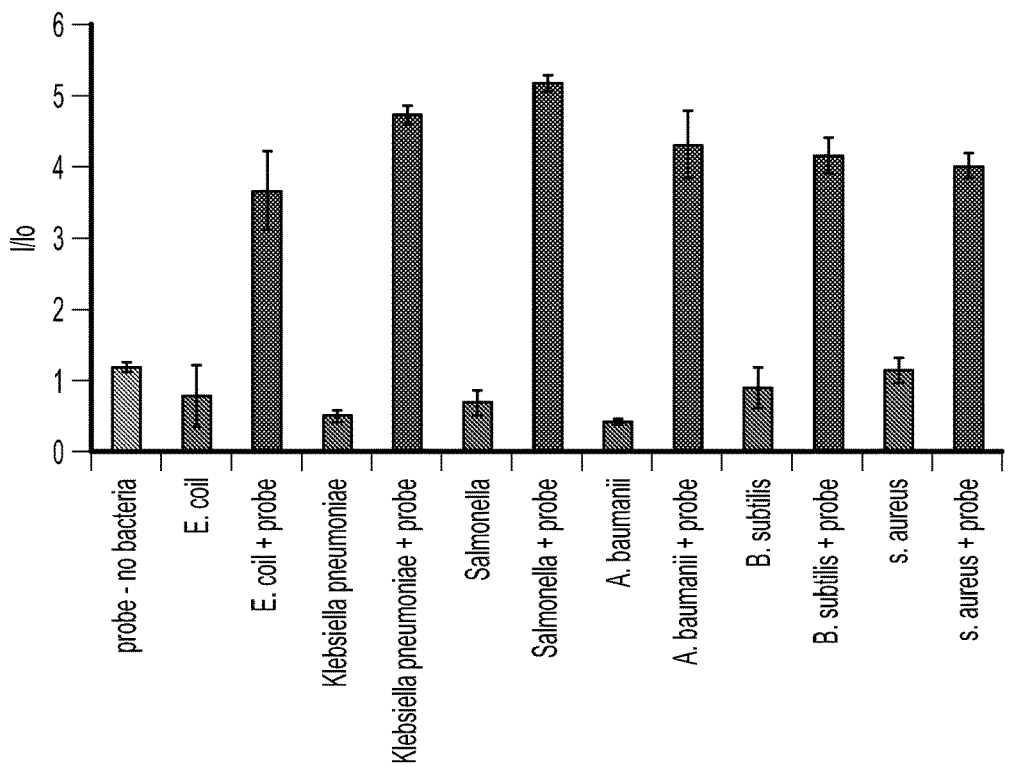
FIG. 27 is a graphical plot illustrating inclusivity with an increase in fluorescence intensity after incubation of different genus of bacteria with Ga-3,3-LiCAM-GluCAM-OG. Experimental detail: incubation time: 20 minutes, incubation media: T-media, concentration of bacterial: $10^8$ CFU/mL.

1. Bacteria is prepared
    a. Sub bacteria onto blood agar and incubate overnight
    b. Select several colonies and grow overnight in LB media at 37° C. in room air on orbital shaker
    c. 100 µl of overnight culture is placed into 100 ml T media, incubated for 5 hours (*E. coli, Salmonella, A. baumannii, Klebsiella pneumoniae*) or 10 hours (*B. subtillus, S. aureus*)
    d. Quantitate using 1:10 dilution and plating 100 µl of dilutions onto blood agar
2. Prepare the samples in 1.5 microcentrifuge tubes, vortex, in triplicate
    a. For each bacteria
        i. 1 ml bacteria+25 µl Tris
        ii. 1 ml bacteria+25 µl Probe
    b. For each run include controls
        i. 1 ml T media+25 µl Tris
        ii. 1 ml T media+25 µl Probe
3. Incubate for 20 minutes on orbital shaker at 37° C. room air
4. Centrifuge at room temperature at 15,000 rpm for 5 minutes
5. Remove supernatant by pipet (pellet may not be visible, remove all fluid carefully)
6. Resuspend pellet in 125 µl T media and vortex
7. Centrifuge at room temperature at 15,000 rpm for 5 min
8. Remove supernatant by pipet (pellet may not be visible, remove all fluid carefully)
9. Resuspend pellet in 125 µl T media and vortex 10. Pipet 100 µl of each sample into 384 black deep well plate (make sure no bubbles)
11. Let sit for 5 minutes
12. Measure in fluorometer at 485 nm (swipe 20 nm) emission at 510-540 nm (swipe 10 nm) and using 800 volt
13. Save results into an excel file.
14. Wash plate and sonicate in ethanol
15. 24+ hours count colonies on quantitative cultures Inclusivity and an increase in fluorescence intensity after incubation of different genus of bacteria with Ga-3,3-LiCAM-GluCAM-OG is illustrated in FIG. 27. Experimental detail: incubation time: 20 minutes, incubation media: T-media, concentration of bacterial: $10^8$ CFU/mL.

Figure 28:
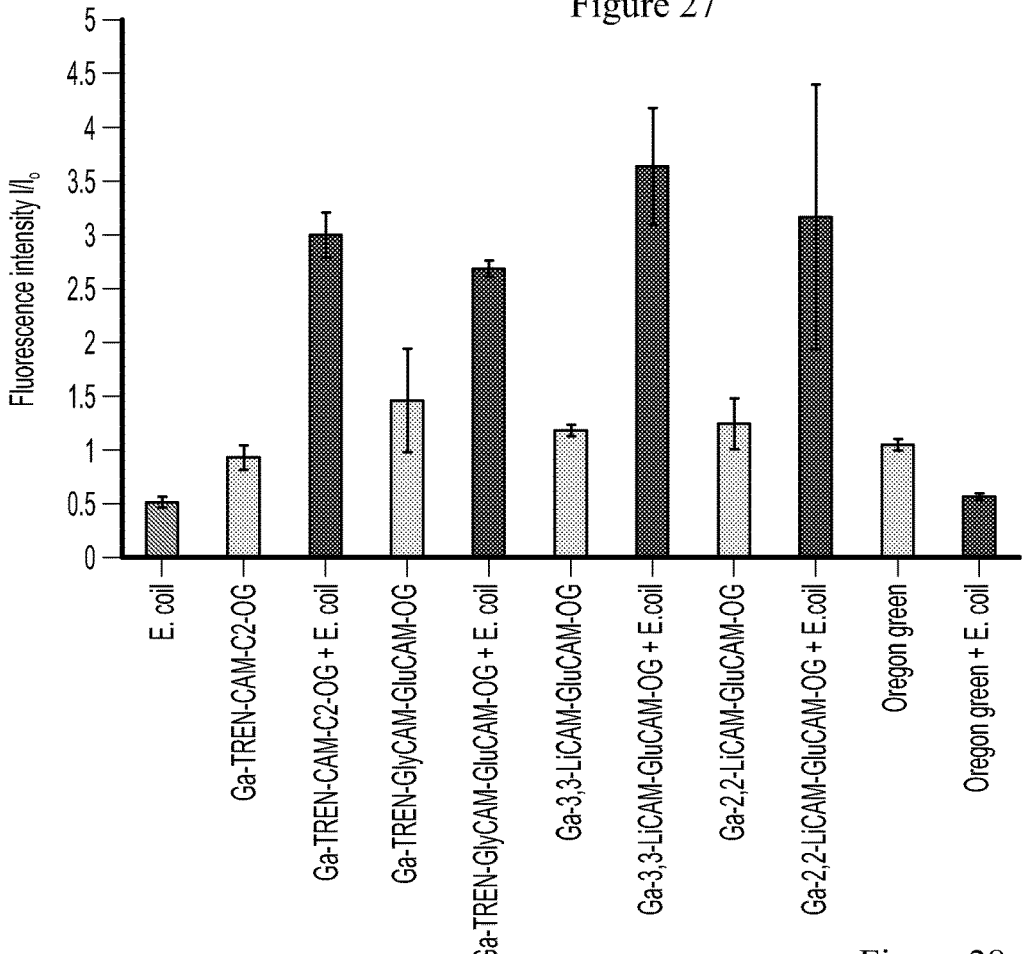
FIG. 28: is a graphical plot illustrating the effect of probe chemical structure on response. Increase in fluorescence intensity after incubation of E. coli with Ga-TREN-CAM-C2-OG (example 1), Ga-TREN-GlyCAM-GluCAM-OG (example 2), Ga-3,3-LiCAM-GluCAM-OG (example 4), Ga-2,2-LiCAM-GluCAM (example 5), and the non-targeted dye OREGON GREEN dye. Experimental detail: incubation time: 20 minutes, incubation media: T-media, concentration of bacterial: $10^8$ CFU/mL.

The effect of probe chemical structure on response can be seen in FIG. 28 in an increase in fluorescence intensity after incubation of E. coli with Ga-TREN-CAM-C2-OG (example 1), Ga-TREN-GlyCAM-GluCAM-OG (example 2), Ga-3,3-LiCAM-GluCAM-OG (example 4), Ga-2,2-LiCAM-GluCAM (example 5), and the non-targeted dye OREGON GREEN dye. Experimental detail: incubation time: 20 minutes, incubation media: T-media, concentration of bacterial: $10^8$ CFU/mL.

Figure 29:
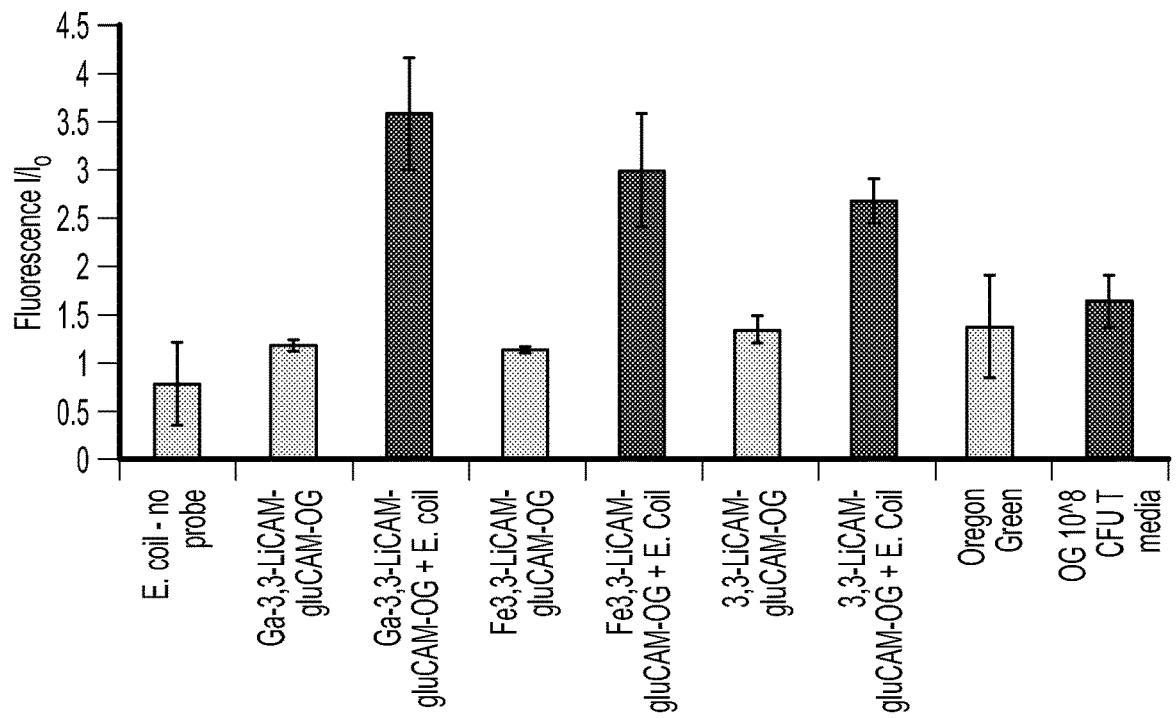
FIG. 29 is a graphical plot illustrating the effect of metal ion on probe uptake. Increase in fluorescence intensity after incubation of E. coli with Ga-3,3-LiCAM-GluCAM-OG, Fe-3,3-LiCAM-GluCAM, the apo probe, 3,3-LiCAM-GluCAM-OG, and the non-target OREGON GREEN dye. Experimental detail: incubation time: 20 minutes, incubation media: T-media, concentration of bacterial: $10^8$ CFU/mL.

The effect of metal ion on probe uptake can be seen in FIG. 29 in an increase in fluorescence intensity after incubation of E. coli with Ga-3,3-LiCAM-GluCAM-OG, Fe-3,3-LiCAM-GluCAM, the apo probe, 3,3-LiCAM-GluCAM-OG, and the non-target OREGON GREEN dye. Experimental detail: incubation time: 20 minutes, incubation media: T-media, concentration of bacterial: $10^8$ CFU/mL.

Figure 30:
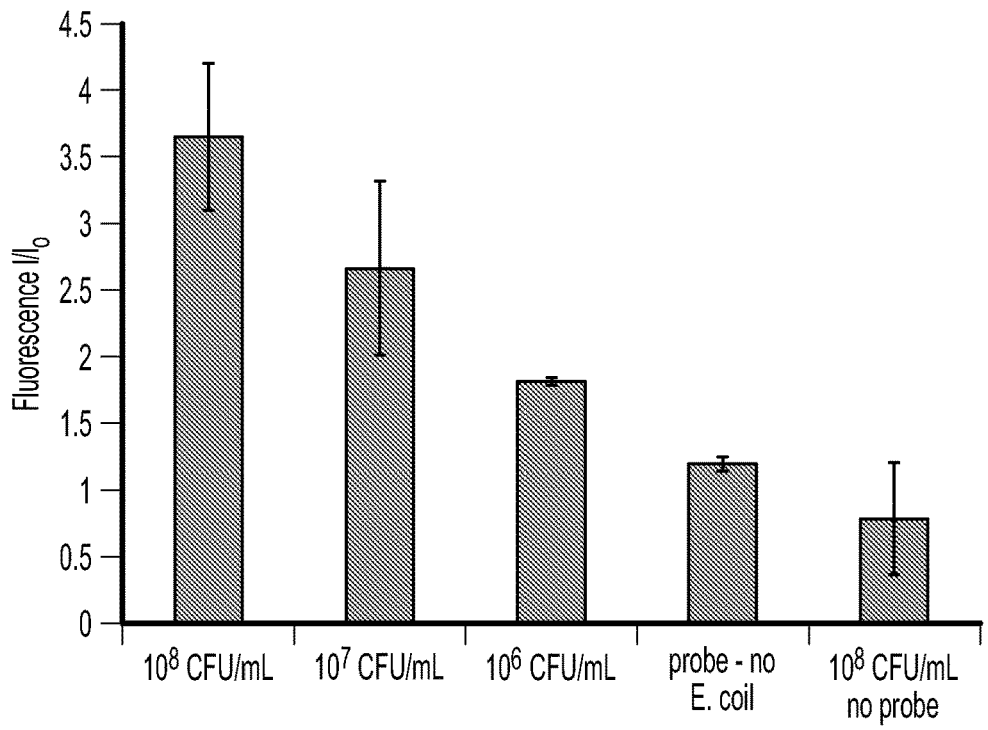
FIG. 30 is a graphical plot illustrating the effect of bacteria concentration, showing an increase in fluorescence intensity after incubation of E. coli with Ga-3,3-LiCAM-GluCAM-OG as a function of bacteria concentration. Experimental detail: incubation time: 20 minutes, incubation media: T-media.

The effect of bacteria concentration can be seen as an increase in fluorescence intensity in FIG. 30 after incubation of E. coli with Ga-3,3-LiCAM-GluCAM-OG as a function of bacteria concentration. Experimental detail: incubation time: 20 minutes, incubation media: T-media.

Figure 31:
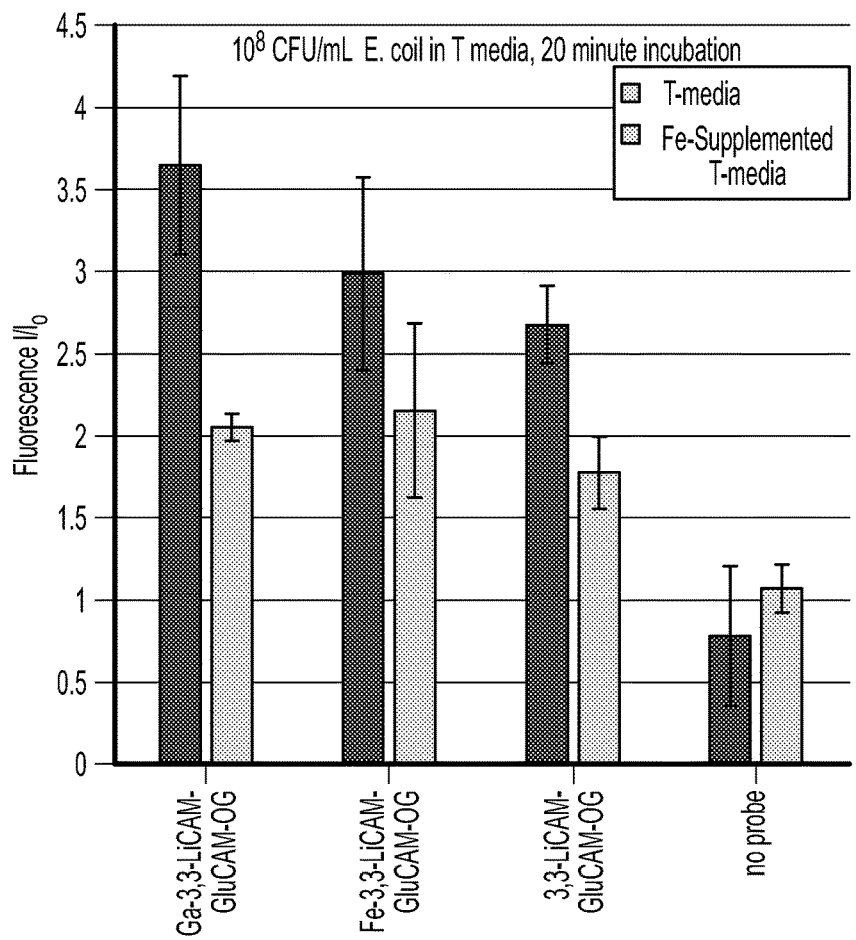
FIG. 31 is a graphical plot illustrating the effect of the concentration of iron in the media on probe uptake showing an increase in fluorescence intensity after incubation of E. coli with Ga-3,3-LiCAM-GluCAM-OG, Fe-3,3-LiCAM-GluCAM, and the apo probe, 3,3-LiCAM-GluCAM-OG in iron-deprived T-media and iron supplemented T-media. The iron supplemented T-media contains an additional 1 µM $FeCl_3$. Experimental detail: incubation time: 20 minutes, concentration of bacterial: $10^8$ CFU/mL.

The effect of the concentration of iron in the media on probe uptake can be seen in an increase in fluorescence intensity in FIG. 31 after incubation of E. coli with Ga-3,3-LiCAM-GluCAM-OG, Fe-3,3-LiCAM-GluCAM, and the apo probe, 3,3-LiCAM-GluCAM-OG in iron-deprived T-media and iron supplemented T-media. The iron supplemented T-media contains an additional 1 µM $FeCl_3$. Experimental detail: incubation time: 20 minutes, concentration of bacterial: $10^8$ CFU/mL.

Figure 32:
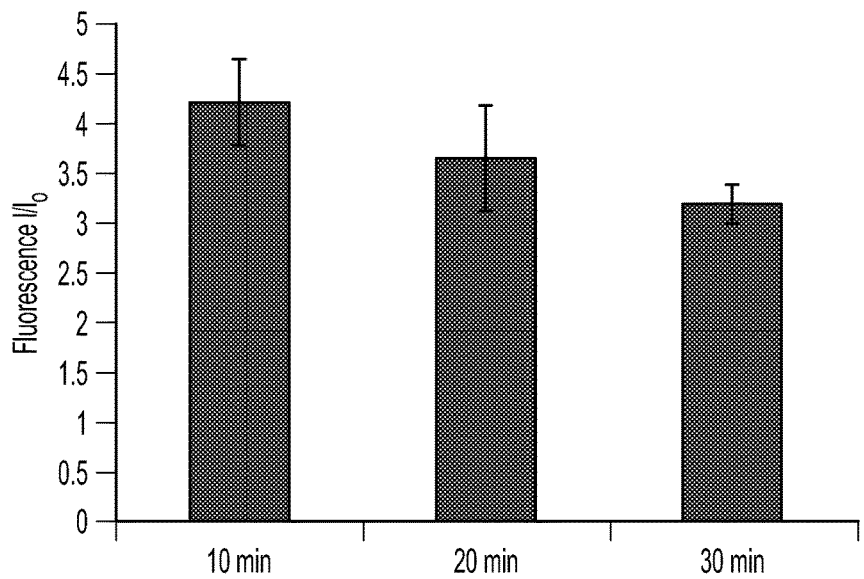
FIG. 32 is a graphical plot illustrating the effect of incubation time showing an increase in fluorescence intensity after incubation of E. coli with Ga-3,3-LiCAM-GluCAM-OG for 10 minutes, 20 minutes, and 30 minutes. Experimental detail: incubation media: T-media, concentration of bacterial: $10^8$ CFU/mL.

The effect of incubation time can be seen in an increase in fluorescence intensity in FIG. 32 after incubation of E. coli with Ga-3,3-LiCAM-GluCAM-OG for 10 minutes, 20 minutes, and 30 minutes. Experimental detail: incubation media: T-media, concentration of bacterial: $10^8$ CFU/mL.

Figure 33:
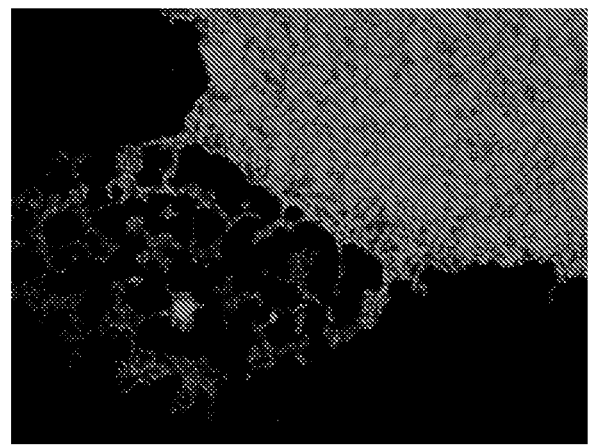
FIG. 33 is an illustration of an epifluorescence image of 0.5 mL of E. coli (ATCC 25922) at $10^7$ cfu/mL incubated with 1 µM Ga-TREN-CAM-C2-6FAM for 5 minutes and filtered on an isopore membrane filter (0.2 µm pore size). Microscopy was done directly on the filter.

An epifluorescence image of 0.5 mL of E. coli (ATCC 25922) at $10^7$ cfu/mL incubated with 1 µM Ga-TREN-CAM-C2-6FAM for 5 minutes and filtered on an isopore membrane filter (0.2 µm pore size) is illustrated in FIG. 33. Microscopy was done directly on the filter.

Sample Processing for Bacteria Detection by Cytomass in T Media Experiments with Bacteria Genus
1. Bacteria is prepared
    a. Sub bacteria onto blood agar and incubate overnight
    b. Select several colonies and grow overnight in LB media at 37° C. in room air on orbital shaker
    c. 100 µl of overnight culture is placed into 100 ml T media, incubated for 5 hours (E. coli, Salmonella, A. baumannii, Klebsiella pneumoniae) or 10 hours (B. subtillus, S. aureus)
    d. Quantitate using 1:10 dilution and plating 100 µl of dilutions onto blood agar
2. Prepare the samples in 1.5 microcentrifuge tubes, vortex, in triplicate
    a. For each bacteria
        i. 1 ml bacteria+25 µl Tris
        ii. 1 ml bacteria+25 µl Probe
    b. For each run include controls
        i. 1 ml T media+25 µl Tris
        ii. 1 ml T media+25 µl Probe
3. Incubate for 20 minutes on orbital shaker at 37° C. room air
4. Centrifuge at room temperature at 15,000 rpm for 5 minutes
5. Remove supernatant by pipet (pellet may not be visible, remove all fluid carefully)
6. Resuspend pellet in 125 µl T media and vortex
7. Centrifuge at room temperature at 15,000 rpm for 5 min
8. Remove supernatant by pipet (pellet may not be visible, remove all fluid carefully)
9. Re-suspend pellet in 125 µl T media and vortex
10. The palettes were spin down (1000 RCF, 4° C., 5 minutes).
11. The supernatant was removed and the palettes were suspended in 4% formaldehyde in PBS.
12. The palettes were incubated 15 minutes at 37° C. and then centrifuged (1000 RCF, 4° C., 5 minutes).
13. The filtrate was removed and the palettes were re-suspended in PBS and spin down (1000 RCF, 4° C., 5 minutes). This later action was repeated twice.
14. After the last wash the palettes was suspended in MQ water and the data were acquire in CytOF Cytomas data is illustrated in FIG. 34. Left: biaxial dot plot where each dot is an individually detected event. The number of mass spectra integrated to give a single "event" on the y-axis of the probe intensity in each event, on the x-axis. Right: histogram of the gated most intense part of the dot cloud indicating the number of terbium ion per event counted (bacteria). For reference, the events shown on the right hand side represent approximately 100,000 "bacterial events".

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. This disclosure is not limited to the exact details shown and described, for variations obvious to one skilled in the art will be included within the disclosure defined by the claims.

What is claimed is:
1. A compound of formula I, II or III:

Formula I

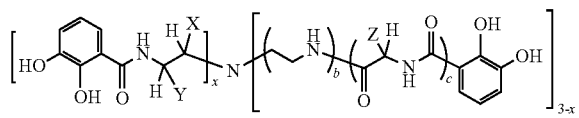

wherein:
each X independently represents H and the vicinal Y represents H or -L-B; or each Y independently represents H and the vicinal X represents H or -L-B;
each Z independently represents H or -L-B;
each L independently represents an organic linking group;

each B independently represents —OR, —NR$_2$, —SR, —C(O)OR, —C(O)NR$_2$, —S(O)R, or —SO$_2$R;
each R independently represents H or an organic group;
each b is independently 0 or 1;
each c is independently 0 or 1; and
x=0 to 3;
with the proviso that at least one of X, Y, or Z is present and represents -L-B; and
wherein at least one R is an organic group, said organic group comprising a group selected from the group consisting of a dye, a Lanthanide complex, a magnetic resonance imaging (MM) contrast agent, a positron emission tomography (PET) agent, a gold nanoparticle, a silver nanoparticle, a quantum dot, an antibiotic or an antibacterial drug, an antimicrobial peptide, a polymer, a dendrimer, an ionophore, and combinations thereof.

2. The compound of claim 1, wherein each organic linking group L independently represents a straight-chain group of the formula —(CH$_2$)$_n$— or —(CH$_2$—CH$_2$—O)$_n$—, wherein n is 1 to 8.

3. The compound of claim 1, wherein each organic linking group L independently represents a branched chain dendrimer that contains one or more of C, N, S, and O.

4. A compound of formula II,

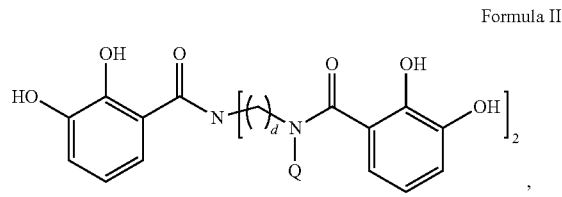

Formula II wherein:
each Q independently represents H or —(CH$_2$)$_n$-D, wherein n is 1 to 8;
each D independently represents —OR, —NR$_2$, —SR, or —C(O)OR;
each R independently represents H or an organic group; and
each d is independently 2 to 5;
with the proviso that at least one Q represents —(CH$_2$)$_n$-D; and
wherein at least one R is an organic group, said organic group comprising a group selected from the group consisting of a dye, a Lanthanide complex, a magnetic resonance imaging (MRI) contrast agent, a positron emission tomography (PET) agent, a gold nanoparticle, a silver nanoparticle, a quantum dot, an antibiotic or an antibacterial drug, an antimicrobial peptide, a polymer, a dendrimer, and ionophore, and combinations thereof.

5. A compound of formula III:

wherein:
each A independently represents —OR, —NR$_2$, —SR, or —C(O)OR;
each R independently represents H or an organic group;
each n is independently 2 to 5;
each e is independently 0 or 1;
each f is independently 2 or 3;
each g is independently 0 or 1; and
x=0 to 3;
with the proviso that at least one A is present and
wherein at least one R is an organic group comprising a group selected from the group consisting of a dye, a Lanthanide complex, a magnetic resonance imaging (MM) contrast agent, a positron emission tomography (PET) agent, a gold nanoparticle, a silver nanoparticle, a quantum dot, an antibiotic or an antibacterial drug, an antimicrobial peptide, a polymer, a dendrimer, an ionophore, and combinations thereof.

6. A complex of a compound of claim 1 selected from the group consisting of a Ga(III) complex, an Fe(III) complex, an Al(III) complex, a V(IV) complex, a Zn(II) complex, an Y(III) complex, a Zr(VI) complex, a Cu(II) complex, and combinations thereof.

7. A complex of a compound of claim 4 selected from the group consisting of a Ga(III) complex, an Fe(III) complex, an Al(III) complex, a V(IV) complex, a Zn(II) complex, an Y(III) complex, a Zr(VI) complex, a Cu(II) complex, and combinations thereof.

8. A complex of a compound of claim 5 selected from the group consisting of a Ga(III) complex, an Fe(III) complex, an Al(III) complex, a V(IV) complex, a Zn(II) complex, an Y(III) complex, a Zr(VI) complex, a Cu(II) complex, and combinations thereof.

9. A method of detecting bacteria comprising:
contacting a probe comprising a compound of formula I, II or III:

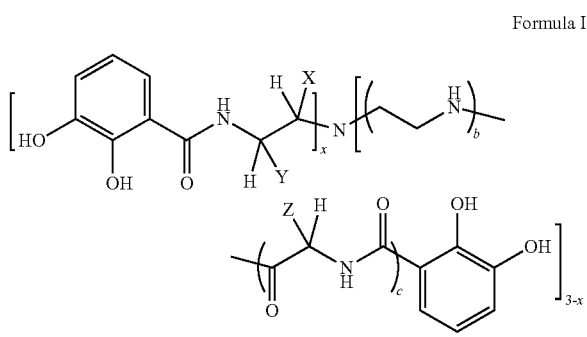

Formula I

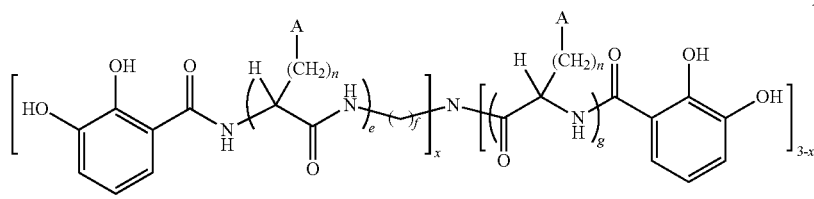

Formula III wherein:
each X independently represents H and the vicinal Y represents H or -L-B; or each Y independently represents H and the vicinal X represents H or -L-B;
each Z independently represents H or -L-B;
each L independently represents an organic linking group;
each B independently represents —OR, —NR$_2$, —SR, —C(O)OR, —C(O)NR$_2$, —S(O)R, or —SO$_2$R;
each R independently represents H or an organic group;
each b is independently 0 or 1;
each c is independently 0 or 1; and
x=0 to 3;
with the proviso that at least one of X, Y, or Z is present and represents -L-B;

Formula II

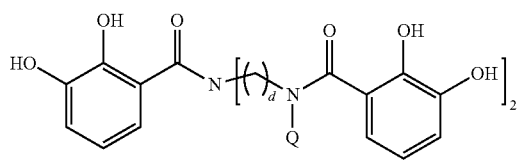

wherein:
each Q independently represents H or —(CH$_2$)$_n$-D, wherein n is 1 to 8;
each D independently represents —OR, —NR$_2$, —SR, or —C(O)OR;
each R independently represents H or an organic group; and
each d is independently 2 to 5;
with the proviso that at least one Q represents —(CH$_2$)$_n$-D; or Formula III

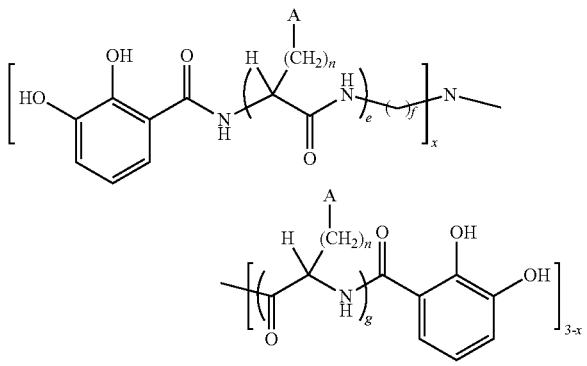

wherein:
each A independently represents —OR, —NR$_2$, —SR, or —C(O)OR;
each R independently represents H or an organic group;
each n is independently 2 to 5;
each e is independently 0 or 1;
each f is independently 2 or 3;
each g is independently 0 or 1; and
x=0 to 3;
with the proviso that at least one A is present,
with a sample comprising a component selected from the group consisting of a bodily fluid, an isolated colony, a culture, and combinations thereof, under conditions effective for the probe to complex Fe(III), Al(III), V(IV), Zn(II), Y(III), Zr(IV), and/or Cu(II) present in the bodily fluid, the isolated colony, and/or the culture; and
detecting the presence of Fe(III), Al(III), V(IV), Zn(II), Y(III), Zr(IV), and/or Cu(II)-probe complex to indicate the presence of bacteria in the bodily fluid, the isolated colony, and/or the culture;
wherein for each of a compound of formula I, II or III, at least one R is an organic group, said organic group comprises a group selected from the group consisting of a dye, a Lanthanide complex, a magnetic resonance imaging (MRI) contrast agent, a positron emission tomography (PET) agent, a gold nanoparticle, a silver nanoparticle, a quantum dot, an antibiotic or an antibacterial drug, an antimicrobial peptide, a polymer, a dendrimer, an ionophore, and combinations thereof.

10. The method of claim 9 further comprising determining the concentration of the Fe(III), ARM), V(IV), Zn(II), Y(III), Zr(IV), and/or Cu(II)-probe complex to indicate the concentration of bacteria in the bodily fluid, the isolated colony, and/or the culture, wherein the concentration of the Fe(III), ARM), V(IV), Zn(II), Y(III), Zr(IV), and/or Cu(II)-probe complex is determined by a technique selected from the group consisting of fluorescence, positron emission tomography (PET), magnetic resonance imaging (MM), field microscopy, colorimetry, electrochemistry, mass spectrometry (MS), fluorescence spectroscopy, and combinations thereof.

11. The method of claim 9, wherein conditions effective for the probes and/or metal-probe complexes to be recognized by bacteria comprise contacting the probe and the sample for 1 minute to 1 hour at 10° C. to 40° C.

12. A method of detecting bacteria comprising:
contacting a probe comprising a compound of formula I, II or III:

Formula I

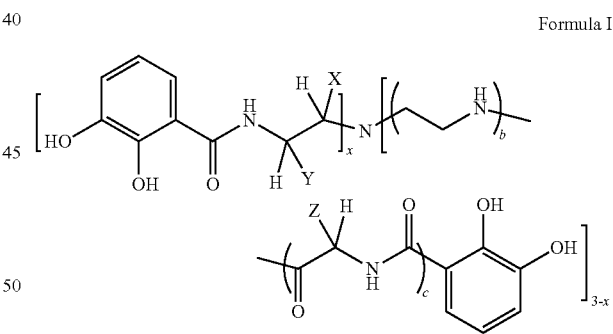

wherein:
each X independently represents H and the vicinal Y represents H or -L-B; or each Y independently represents H and the vicinal X represents H or -L-B;
each Z independently represents H or -L-B;
each L independently represents an organic linking group;
each B independently represents —OR, —NR$_2$, —SR, —C(O)OR, —C(O)NR$_2$, —S(O)R, or —SO$_2$R;
each R independently represents H or an organic group;
each b is independently 0 or 1;
each c is independently 0 or 1; and
x=0 to 3;

with the proviso that at least one of X, Y, or Z is present and represents -L-B;

Formula II

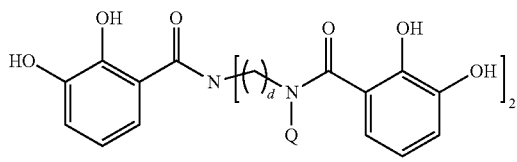

wherein:
each Q independently represents H or —(CH$_2$)$_n$-D, wherein n is 1 to 8;
each D independently represents —OR, —NR$_2$, —SR, or —C(O)OR;
each R independently represents H or an organic group; and
each d is independently 2 to 5;
with the proviso that at least one Q represents —(CH$_2$)$_n$-D; or Formula III

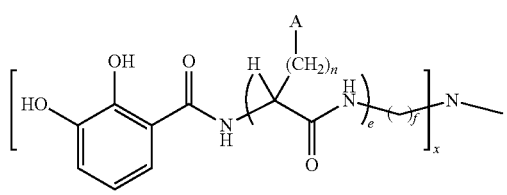

wherein:
each A independently represents —OR, —NR$_2$, —SR, or —C(O)OR;
each R independently represents H or an organic group;
each n is independently 2 to 5;
each e is independently 0 or 1;
each f is independently 2 or 3;
each g is independently 0 or 1; and
x=0 to 3;
with the proviso that at least one A is present,
wherein for each of a compound of formula I, II or III, at least one R is an organic group, said organic group comprising a group selected from the group consisting of a dye, a Lanthanide complex, a magnetic resonance imaging (MRI) contrast agent, a positron emission tomography (PET) agent, a gold nanoparticle, a silver nanoparticle, a quantum dot, an antibiotic or an antibacterial drug, an antimicrobial peptide, a polymer, a dendrimer, an ionophore, and combinations thereof;

with a sample comprising a bodily fluid, under conditions effective for the probe to complex Fe(III), Al(III), V(IV), Zn(II), Y(III), Zr(IV), and/or Cu(II) present in the bodily fluid; and detecting the presence of Fe(III), Al(III), V(IV), Zn(II), Y(III), Zr(IV), and/or Cu(II)-probe complex to indicate the presence of bacteria in the bodily fluid, wherein the sample comprising the bodily fluid is selected from the group consisting of urine, blood, cerebrospinal fluid (CSF), pleural fluid, a bacteria culture, an isolated colony reconstituted in media, and combinations thereof.

13. The method of claim 9, wherein the detected bacteria is Gram-negative or Gram-positive.

14. A method of determining susceptibility of bacteria to an antibiotic comprising:

treating a sample comprising a component selected from the group consisting of a bodily fluid, a bacteria culture, a single colony reconstituted in media with an antibiotic, and combinations thereof;

contacting a probe comprising a compound of formula I, II or III:

Formula I

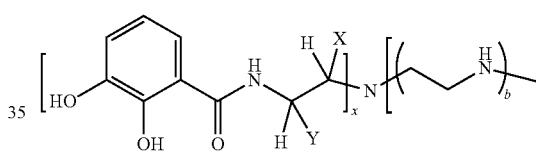

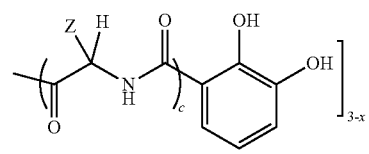

wherein:
each X independently represents H and the vicinal Y represents H or -L-B; or each Y
independently represents H and the vicinal X represents H or -L-B;
each Z independently represents H or -L-B;
each L independently represents an organic linking group;
each B independently represents —OR, —NR$_2$, —SR, —C(O)OR, —C(O)NR$_2$, —S(O)R, or —SO$_2$R;
each R independently represents H or an organic group;
each b is independently 0 or 1;
each c is independently 0 or 1; and
x=0 to 3;

with the proviso that at least one of X, Y, or Z is present and represents -L-B;

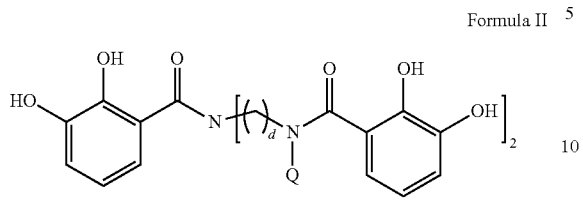

Formula II wherein:
each Q independently represents H or —(CH$_2$)$_n$-D, wherein n is 1 to 8;
each D independently represents —OR, —NR$_2$, —SR, or —C(O)OR;
each R independently represents H or an organic group; and
each d is independently 2 to 5;
with the proviso that at least one Q represents —(CH$_2$)$_n$-D;
or

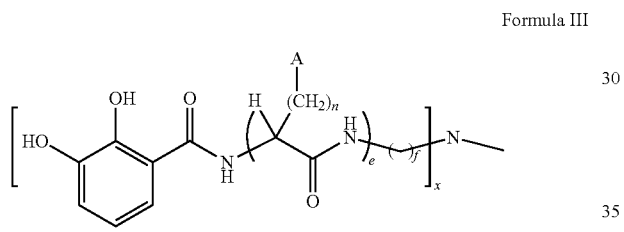

Formula III wherein:
each A independently represents —OR, —NR$_2$, —SR, or —C(O)OR;
each R independently represents H or an organic group;
each n is independently 2 to 5;
each e is independently 0 or 1;
each f is independently 2 or 3;
each g is independently 0 or 1; and
x=0 to 3;
with the proviso that at least one A is present,
wherein for each of a compound of formula I, II or III, at least one R is an organic group, said organic group comprising a group selected from the group consisting of a dye, a Lanthanide complex, a magnetic resonance imaging (MRI) contrast agent, a positron emission tomography (PET) agent, a gold nanoparticle, a silver nanoparticle, a quantum dot, an antibiotic or an antibacterial drug, an antimicrobial peptide, a polymer, a dendrimer, an ionophore, and combinations thereof;
with the sample comprising the bodily fluid, the isolated colony, and/or the culture under conditions effective for the probe to complex Fe(III); and
determining the change in concentration of the compound or complex to indicate the concentration of bacteria in the bodily fluid, the bacteria culture, or the isolated colony after treatment with the antibiotic,
wherein the difference between the initial concentration of bacteria and the concentration of bacteria in the bodily fluid, the bacteria culture, or the isolated colony after treatment with the antibiotic is an indication of the susceptibility of the bacteria to the antibiotic.

15. The method of claim 14, wherein the concentration of the Fe(III), Al(III), V(IV), Zn(II), Y(III), Zr(IV), and/or Cu(II)-probe complex is determined by a technique selected from the group consisting of fluorescence, positron emission tomography (PET), magnetic resonance imaging (MRI), field microscopy, colorimetry, electrochemistry, mass spectrometry (MS), fluorescence spectroscopy, and combinations thereof.

16. A compound selected from the group consisting of:

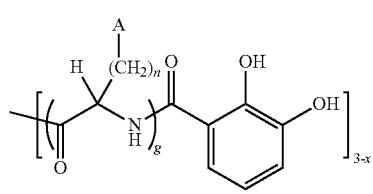

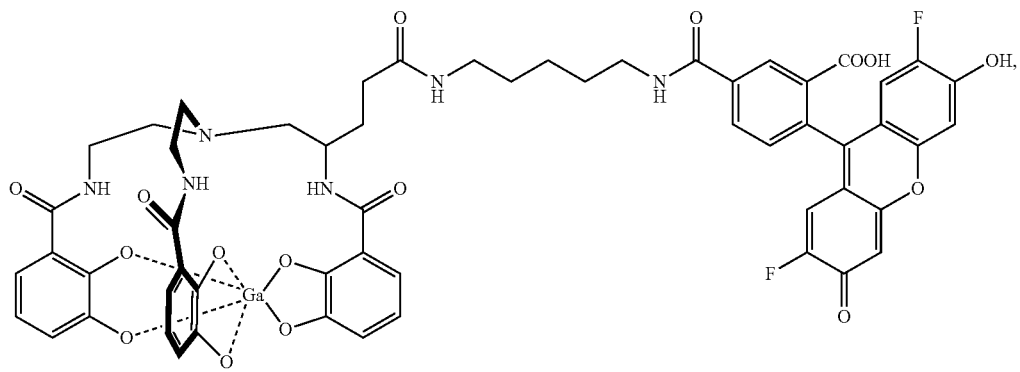

-continued
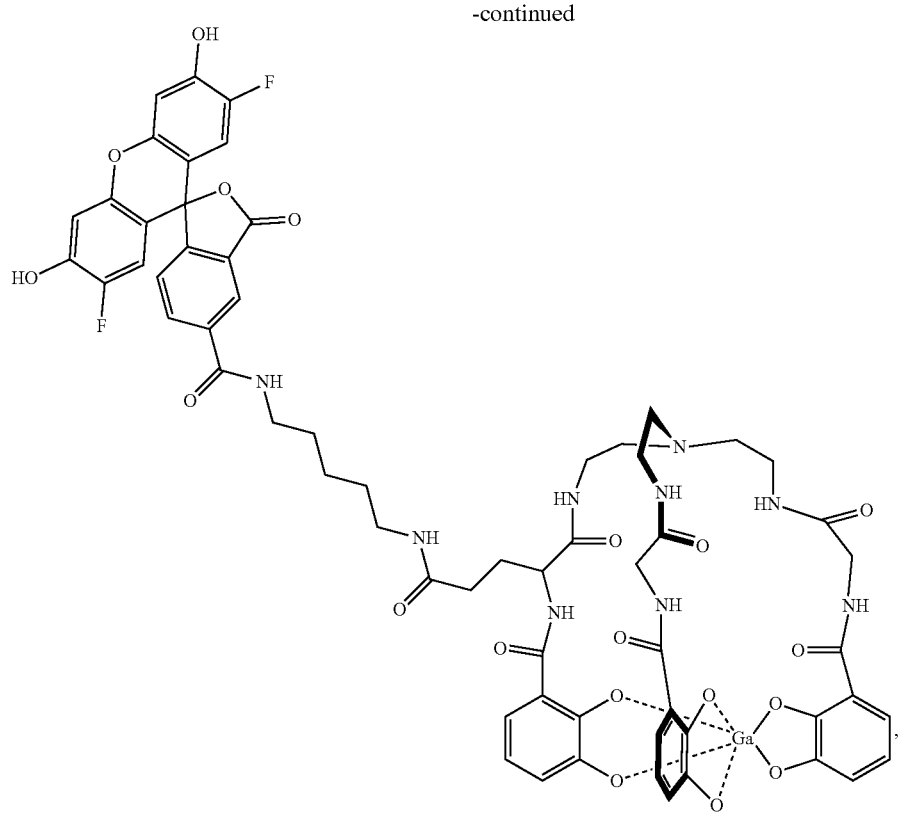
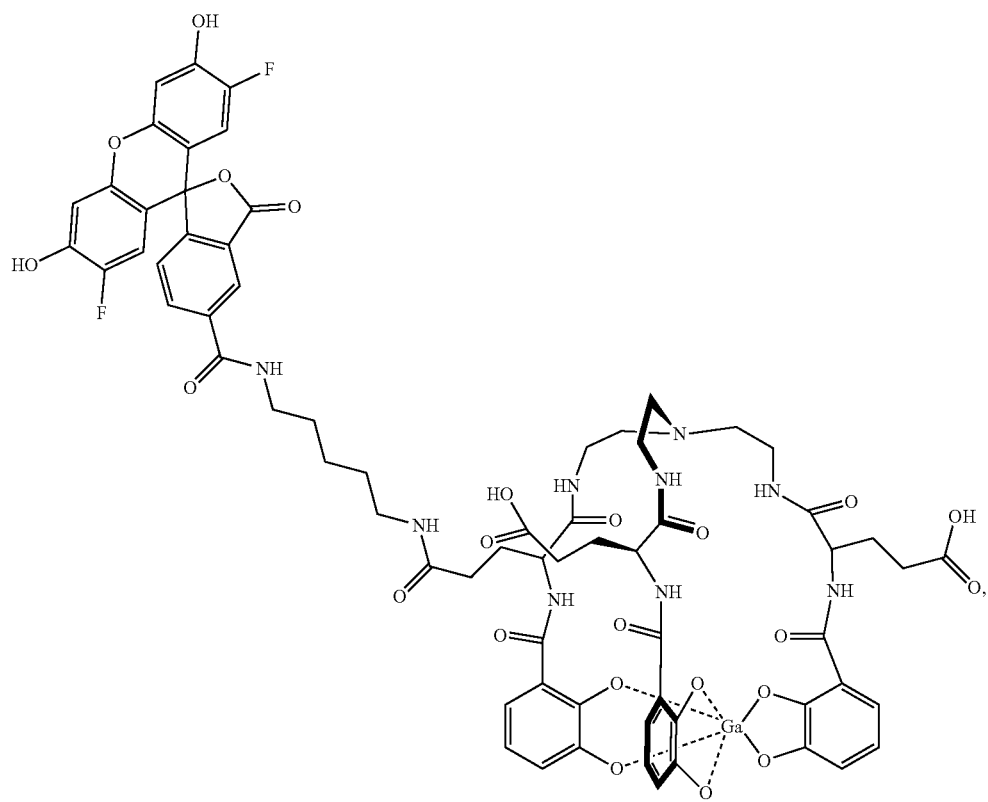

-continued
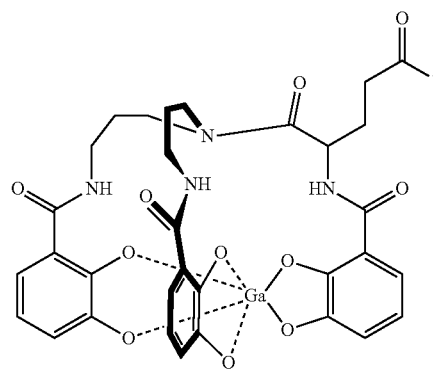 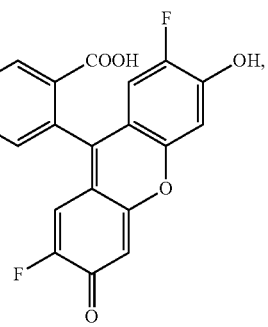
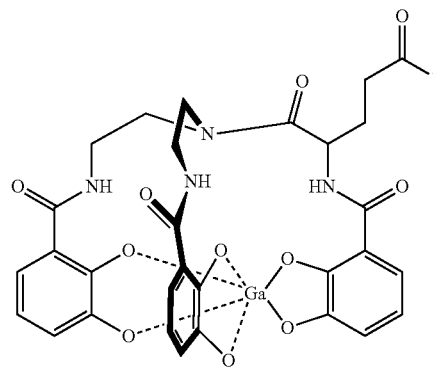 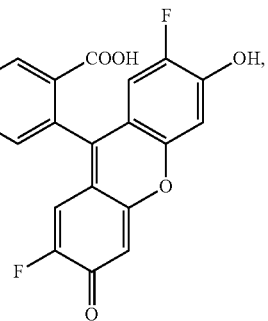
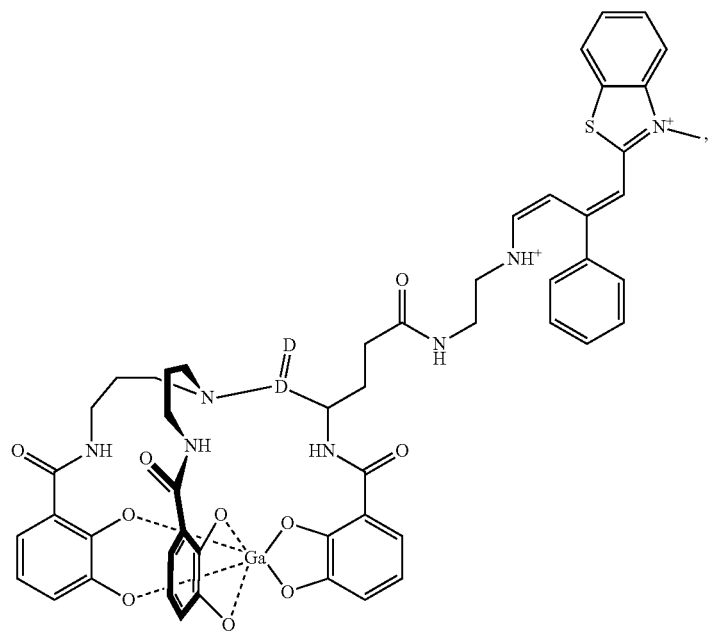

-continued

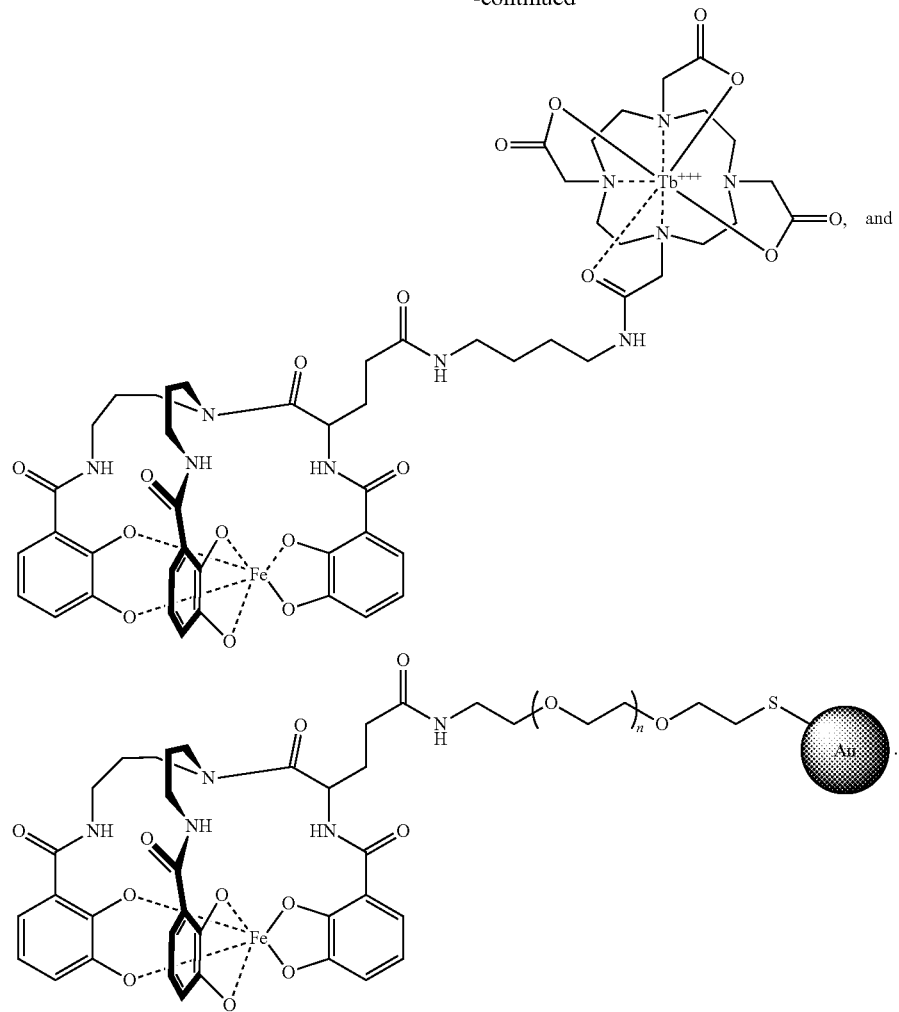

17. The method of claim 9, wherein the presence of the Fe(III), V(IV), Zn(II), Y(III), Zr(IV), and/or Cu(II)-probe complex is detected by a technique selected from the group consisting of fluorescence, positron emission tomography (PET), magnetic resonance imaging (MRI), field microscopy, colorimetry, electrochemistry, mass spectrometry (MS), fluorescence spectroscopy, and combinations thereof.

* * * * *

UNITED STATES PATENT AND TRADEMARK OFFICE
CERTIFICATE OF CORRECTION

PATENT NO. : 10,969,387 B2  
APPLICATION NO. : 16/062806  
DATED : April 6, 2021  
INVENTOR(S) : Valerie Christine Pierre and Sylvie Pailloux Page 1 of 1

It is certified that error appears in the above-identified patent and that said Letters Patent is hereby corrected as shown below:

On the Title Page

Item (57), Line 2 of ABSTRACT, "probes not necessary are" should read -- probes are --.

In the Claims

Claim 1, Column 36, Line 51, "of formula I, II, III:" should read -- of formula I: --.

Claim 1, Column 37, Line 12, "imaging (MM) contrast" should read -- imaging (MRI) contrast --.

Claim 5, Column 38, Lines 15 and 16, "imaging (MM) contrast" should read -- imaging (MRI) contrast --.

Claim 10, Column 40, Line 19, "Fe(III), ARM), V(IV)" should read -- FE(III), Al(III), V(IV) --.

Claim 10, Column 40, Lines 23 and 24, "Fe(III), ARM), V(IV)" should read -- Fe(III), Al(III), V(IV) --.

Claim 10, Column 40, Line 26, "imaging (MM) field" should read -- imaging (MRI) field --.

Signed and Sealed this  
Twenty-second Day of June, 2021

Drew Hirshfeld  
*Performing the Functions and Duties of the*  
*Under Secretary of Commerce for Intellectual Property and*  
*Director of the United States Patent and Trademark Office*